(12) United States Patent
Lemischka

(10) Patent No.: US 6,960,446 B2
(45) Date of Patent: Nov. 1, 2005

(54) METHOD FOR ISOLATING CELLS EXPRESSING FLK-2

(75) Inventor: Ihor R. Lemischka, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/919,408

(22) Filed: Jul. 31, 2001

(65) Prior Publication Data

US 2002/0072077 A1 Jun. 13, 2002

Related U.S. Application Data

(63) Continuation of application No. 09/208,786, filed on Dec. 10, 1998, now abandoned, which is a continuation of application No. 09/021,324, filed on Feb. 10, 1998, now Pat. No. 5,912,133, which is a continuation of application No. 08/601,891, filed on Feb. 15, 1996, now Pat. No. 5,747,651, which is a division of application No. 08/252,498, filed on Oct. 31, 1994, now abandoned, which is a division of application No. 08/055,269, filed on Apr. 30, 1993, now Pat. No. 5,367,057, which is a division of application No. 07/977,451, filed on Nov. 19, 1992, now Pat. No. 5,270,458, which is a continuation-in-part of application No. 07/975,049, filed on Nov. 12, 1992, now abandoned, which is a continuation-in-part of application No. 07/906,397, filed on Jun. 26, 1992, now Pat. No. 5,621,090, which is a continuation-in-part of application No. 07/813,593, filed on Dec. 24, 1991, now Pat. No. 5,185,438, which is a continuation-in-part of application No. 07/793,065, filed on Nov. 15, 1991, now abandoned, which is a continuation-in-part of application No. 07/728,913, filed on Jun. 28, 1991, now abandoned, which is a continuation-in-part of application No. 07/679,666, filed on Apr. 2, 1991, now abandoned.

(51) Int. Cl.$^7$ ............................................. G01N 33/567

(52) U.S. Cl. ........................... 435/7.21; 435/2; 435/7.1; 435/7.24; 435/375; 435/377

(58) Field of Search ........................... 424/140.1, 130.1, 424/153.1; 435/2; 530/387.1, 388.22

(56) References Cited

U.S. PATENT DOCUMENTS

| 4,714,680 A | 12/1987 | Civin |
| 4,965,204 A | 10/1990 | Civin |
| 5,061,620 A | 10/1991 | Tsukamoto et al. |
| 5,130,144 A | 7/1992 | Civin |

(Continued)

FOREIGN PATENT DOCUMENTS

| EP | 0 317 156 | 5/1989 |
| EP | 0 330 191 | 8/1989 |
| EP | 0 395 355 | 10/1990 |
| WO | WO 92/14748 | 9/1992 |

OTHER PUBLICATIONS

Lederman et al. Mol. Immunol. 11: 1171–1181 (1991).*
Li et al. PNAS 77: 3211–3214 (1980).*

(Continued)

Primary Examiner—Phillip Gambel
(74) Attorney, Agent, or Firm—Kenyon & Kenyon

(57) ABSTRACT

Isolated mammalian nucleic acid molecules encoding receptor protein tyrosine kinases expressed in primitive hematopoietic cells and not expressed in mature hematopoietic cells are provided. Also included are the receptors encoded by such nucleic acid molecules; the nucleic acid molecules encoding receptor protein tyrosine kinases having the sequences shown in FIG. 1a (murine flk-2), FIG. 1b (human flk-2) and FIG. 2 (murine flk-1); the receptor protein tyrosine kinases having the amino acid sequences shown in FIG. 1a, FIG. 1b and FIG. 2; ligands for the receptors; nucleic acid sequences that encode the ligands; and methods of stimulating the proliferation and/or differentiation of primitive mammalian hematopoietic stem cells comprising contacting the stem cells with a ligand that binds to a receptor protein tyrosine kinase expressed in primitive mammalian hematopoietic cells and not expressed in mature hematopoietic cells.

1 Claim, 23 Drawing Sheets

U.S. PATENT DOCUMENTS

| | | |
|---|---|---|
| 5,185,438 A | 2/1993 | Lemischka |
| 5,270,458 A | 12/1993 | Lemischka |
| 5,283,354 A | 2/1994 | Lemischka |
| 5,367,057 A | 11/1994 | Lemischka |
| 5,621,090 A | 4/1997 | Lemischka et al. |
| 5,912,133 A | 6/1999 | Lemischka |

OTHER PUBLICATIONS

Skolnick et al. Tibtech 18: 34–38 (2000).*
Ngo et al. In the Protein Folding Problem and Tertiary Structure Prediction Edited by Merz and Le Grand, Birkhauser, Boston 1994, pages.*
Dexter & Spooncer, Annual Review of Cell Biology 3, (1987), pp. 423–441.
Copeland et al., Cell 63 (1990), pp. 175–183.
Hanks et al., Science 241 (1988), pp. 42–52.
Wilks, Proc. Natl. Acad. Sci. USA 86 (1989), pp. 1603–1607.
Hopp et al., Proc. Natl. Acad. Sci. USA 78, (1981), pp. 3824–3828.
Jordan et al., Cell 61 (1990), pp. 953–963.
Ikuta et al., Cell 62 (1990), pp. 863–864.
Spangrude et al., Science 241 (1988), pp. 58–62.
Szilvassy et al., Blood 74 (1989), pp. 930–939.
Andrews et al., Journal of Experimental Medicine 169 (1989), pp. 1721–1731.
Flanagan et al., Cell 63 (1990), pp. 185–194.
Hammerschmidt et al., Nature 340 (1989), pp. 393–397.
Abcouwer et al., Biotechnology 7 (1989), pp. 939–946.
Matthews et al., Cell 65 (1991), pp. 1143–1152.
Civin, Exp. Hematol. 15 (1987), pp. 10–17.
Rosnet et al., Oncogene 6 (1991), pp. 1641–1650.
Rosnet et al., Genomics 9 (1991) pp. 380–385.
Terman et al., Oncogene 6 (1991) pp. 1676–1683.
Lemischka et al., Cell 45 (1986), pp. 917–927.
Williams et al., Cell 63 (1990), pp. 163–174.
Zsebo et al., Cell 63 (1990), pp. 195–201.
Martin et al., Cell 63 (1990), pp. 203–211.
Zsebo et al., Cell 63 (1990), pp. 213–224.
Orr, Genetic Engineering News, (Feb. 1991), p. 8.
Batuman et al., Journal of Immunology 130 (1983), pp. 1051–1055.
Streeten et al., Proc. Nat'l. Acad. Sci. 86 (1989), pp. 916–920.
Zipori, Int'l. Journal of Cell Cloning 7 (1989), pp. 281–291.
Kabrun et al., Development 124 (1997), pp. 2039–2048.
Loken et al., Blood 69 (Jan. 1987), pp. 255–263.
Suda et al., Int'l Journal of Hematology 71 (2000), pp. 99–107.
Bolen et al., FASEB 6, (1992), pp. 3403–3409.
Jones et al., Proc. Nat'l Acad. Sci, USA 85 (1988), pp. 3377–3381.
Matthews et al., PNAS 88:9026–9030, Oct. 1991.
Millauer et al., Cell 72:835–846, 1993.
Nakamura, et al, "Ex Vivo Generation of CD34+ cells from CD34– Hematopoietic cells" Blood, Dec. 15, 1999, vol. 94, No. 12, pp. 4053–4059.
Nocka et al., "Candidate ligand for the C–kit transmembrane Kinase receptor: KL, a fibroblast derived growth factor stimulates mast cells and erythroid progenitors" vol. 9, No. 10, pp. 3287–3294, 1990.
Nocka, K. et al., "Expression of C–Kit gene products in known cellular targets of W mutations in normal and W mutant mice–evidence for an impaired C–Kit Kinase in mutant mice, Genes and Development" vol. 3, No. 6, pp. 739–920, 1989.
Peichev, et al., "Expression of VEGFR–3 and AC133 by circulating human CD34 Cells identifies a population of functional endothelial precursors" Blood, Feb. 1, 2000, vol. 95, No. 3, 953–958.
Sarzani et al., Biochem Biophys Res Comm. 186(2) 706–714 Jul. 31, 1992.
Terman et al., Biochem Biophys Res Comm. 187(3) 1579, 1992.
Wek et al., Proc. Nat'l Acad. Sci, USA 86, (1989), pp. 4579–4583.
Wilks PNAS 86:1603–1607 Mar. 1989.
Yamaguchi, et al., "flk–1, an flt–related receptor tyrosine kinase is an early marker for endothelial cell precursors" Development 118, 489–498, 1993.
Yang et al., J. Neuroscience 16:6089–6099, 1996.

* cited by examiner

Fig. 1a.1

```
GCGGCCTGGC TACCGCGCGC TCCGGAGGCC ATG CGG GCG TTG GCG CAG CGC AGC
                                   Met Arg Ala Leu Ala Gln Arg Ser
                                   -27     -25                 -20

GAC CGG CGG CTG CTG CTG CTT GTT GTT TTG TCA GTA ATG ATT CTT GAG
Asp Arg Arg Leu Leu Leu Leu Val Val Leu Ser Val Met Ile Leu Glu
            -15                 -10                         -5

ACC GTT ACA AAC CAA GAC CTG CCT GTG ATC AAG TGT GTT TTA ATC AGT
Thr Val Thr Asn Gln Asp Leu Pro Val Ile Lys Cys Val Leu Ile Ser
            1               5                   10

CAT GAG AAC AAT GGC TCA TCA GCG GGA AAG CCA TCA TCG TAC CGA ATG
His Glu Asn Asn Gly Ser Ser Ala Gly Lys Pro Ser Ser Tyr Arg Met
    15              20                  25

GTG CGA GGA TCC CCA GAA GAC CTC CAG TGT ACC CCG AGG CGC CAG AGT
Val Arg Gly Ser Pro Glu Asp Leu Gln Cys Thr Pro Arg Arg Gln Ser
30                  35                  40                  45

GAA GGG ACG GTA TAT GAA GCG GCC ACC GTG GAG GTG GCC GAG TCT GGG
Glu Gly Thr Val Tyr Glu Ala Ala Thr Val Glu Val Ala Glu Ser Gly
                50                  55                      60

TCC ATC ACC CTG CAA GTG CAG CTC GCC ACC CCA GGG GAC CTT TCC TGC
Ser Ile Thr Leu Gln Val Gln Leu Ala Thr Pro Gly Asp Leu Ser Cys
            65                  70                  75

CTC TGG GTC TTT AAG CAC AGC TCC CTG GGC TGC CAG CCG CAC TTT GAT
Leu Trp Val Phe Lys His Ser Ser Leu Gly Cys Gln Pro His Phe Asp
        80                  85                  90

TTA CAA AAC AGA GGA ATC GTT TCC ATG GCC ATC TTG AAC GTG ACA GAG
Leu Gln Asn Arg Gly Ile Val Ser Met Ala Ile Leu Asn Val Thr Glu
        95              100             105

ACC CAG GCA GGA GAA TAC CTA CTC CAT ATT CAG AGC GAA CGC GCC AAC
Thr Gln Ala Gly Glu Tyr Leu Leu His Ile Gln Ser Glu Arg Ala Asn
110             115             120                         125

TAC ACA GTA CTG TTC ACA GTG AAT GTA AGA GAT ACA CAG CTG TAT GTG
Tyr Thr Val Leu Phe Thr Val Asn Val Arg Asp Thr Gln Leu Tyr Val
                130             135                     140

CTA AGG AGA CCT TAC TTT AGG AAG ATG GAA AAC CAG GAT GCA CTG CTC
Leu Arg Arg Pro Tyr Phe Arg Lys Met Glu Asn Gln Asp Ala Leu Leu
            145             150                 155
```

Fig. 1a.2

```
TGC ATC TCC GAG GGT GTT CCG GAG CCC ACT GTG GAG TGG GTG CTC TGC
Cys Ile Ser Glu Gly Val Pro Glu Pro Thr Val Glu Trp Val Leu Cys
        160                 165                 170

AGC TCC CAC AGG GAA AGC TGT AAA GAA GAA GGC CCT GCT GTT GTC AGA
Ser Ser His Arg Glu Ser Cys Lys Glu Glu Gly Pro Ala Val Val Arg
    175                 180                 185

AAG GAG GAA AAG GTA CTT CAT GAG TTG TTC GGA ACA GAC ATC AGA TGC
Lys Glu Glu Lys Val Leu His Glu Leu Phe Gly Thr Asp Ile Arg Cys
190             195                 200                 205

TGT GCT AGA AAT GCA CTG GGC CGC GAA TGC ACC AAG CTG TTC ACC ATA
Cys Ala Arg Asn Ala Leu Gly Arg Glu Cys Thr Lys Leu Phe Thr Ile
                210                 215                 220

GAT CTA AAC CAG GCT CCT CAG AGC ACA CTG CCC CAG TTA TTC CTG AAA
Asp Leu Asn Gln Ala Pro Gln Ser Thr Leu Pro Gln Leu Phe Leu Lys
            225                 230                 235

GTG GGG GAA CCC TTG TGG ATC AGG TGT AAG GCC ATC CAT GTG AAC CAT
Val Gly Glu Pro Leu Trp Ile Arg Cys Lys Ala Ile His Val Asn His
        240                 245                 250

GGA TTC GGG CTC ACC TGG GAG CTG GAA GAC AAA GCC CTG GAG GAG GGC
Gly Phe Gly Leu Thr Trp Glu Leu Glu Asp Lys Ala Leu Glu Glu Gly
    255                 260                 265

AGC TAC TTT GAG ATG AGT ACC TAC TCC ACA AAC AGG ACC ATG ATT CGG
Ser Tyr Phe Glu Met Ser Thr Tyr Ser Thr Asn Arg Thr Met Ile Arg
270             275                 280                 285

ATT CTC TTG GCC TTT GTG TCT TCC GTG GGA AGG AAC GAC ACC GGA TAT
Ile Leu Leu Ala Phe Val Ser Ser Val Gly Arg Asn Asp Thr Gly Tyr
                290                 295                 300

TAC ACC TGC TCT TCC TCA AAG CAC CCC AGC CAG TCA GCG TTG GTG ACC
Tyr Thr Cys Ser Ser Ser Lys His Pro Ser Gln Ser Ala Leu Val Thr
            305                 310                 315

ATC CTA GAA AAA GGG TTT ATA AAC GCT ACC AGC TCG CAA GAA GAG TAT
Ile Leu Glu Lys Gly Phe Ile Asn Ala Thr Ser Ser Gln Glu Glu Tyr
        320                 325                 330

GAA ATT GAC CCG TAC GAA AAG TTC TGC TTC TCA GTC AGG TTT AAA GCG
Glu Ile Asp Pro Tyr Glu Lys Phe Cys Phe Ser Val Arg Phe Lys Ala
335                 340                 345
```

Fig. 1a.3

```
TAC CCA CGA ATC CGA TGC ACG TGG ATC TTC TCT CAA GCC TCA TTT CCT
Tyr Pro Arg Ile Arg Cys Thr Trp Ile Phe Ser Gln Ala Ser Phe Pro
350             355             360             365

TGT GAA CAG AGA GGC CTG GAG GAT GGG TAC AGC ATA TCT AAA TTT TGC
Cys Glu Gln Arg Gly Leu Glu Asp Gly Tyr Ser Ile Ser Lys Phe Cys
            370             375             380

GAT CAT AAG AAC AAG CCA GGA GAG TAC ATA TTC TAT GCA GAA AAT GAT
Asp His Lys Asn Lys Pro Gly Glu Tyr Ile Phe Tyr Ala Glu Asn Asp
        385             390             395

GAC GCC CAG TTC ACC AAA ATG TTC ACG CTG AAT ATA AGA AAG AAA CCT
Asp Ala Gln Phe Thr Lys Met Phe Thr Leu Asn Ile Arg Lys Lys Pro
    400             405             410

CAA GTG CTA GCA AAT GCC TCA GCC AGC CAG GCG TCC TGT TCC TCT GAT
Gln Val Leu Ala Asn Ala Ser Ala Ser Gln Ala Ser Cys Ser Ser Asp
415             420             425

GGC TAC CCG CTA CCC TCT TGG ACC TGG AAG AAG TGT TCG GAC AAA TCT
Gly Tyr Pro Leu Pro Ser Trp Thr Trp Lys Lys Cys Ser Asp Lys Ser
430             435             440             445

CCC AAT TGC ACG GAG GAA ATC CCA GAA GGA GTT TGG AAT AAA AAG GCT
Pro Asn Cys Thr Glu Glu Ile Pro Glu Gly Val Trp Asn Lys Lys Ala
            450             455             460

AAC AGA AAA GTG TTT GGC CAG TGG GTG TCG AGC AGT ACT CTA AAT ATG
Asn Arg Lys Val Phe Gly Gln Trp Val Ser Ser Ser Thr Leu Asn Met
        465             470             475

AGT GAG GCC GGG AAA GGG CTT CTG GTC AAA TGC TGT GCG TAC AAT TCT
Ser Glu Ala Gly Lys Gly Leu Leu Val Lys Cys Cys Ala Tyr Asn Ser
    480             485             490

ATG GGC ACG TCT TGC GAA ACC ATC TTT TTA AAC TCA CCA GGC CCC TTC
Met Gly Thr Ser Cys Glu Thr Ile Phe Leu Asn Ser Pro Gly Pro Phe
495             500             505

CCT TTC ATC CAA GAC AAC ATC TCC TTC TAT GCG ACC ATT GGG CTC TGT
Pro Phe Ile Gln Asp Asn Ile Ser Phe Tyr Ala Thr Ile Gly Leu Cys
510             515             520             525

CTC CCC TTC ATT GTT GTT CTC ATT GTG TTG ATC TGC CAC AAA TAC AAA
Leu Pro Phe Ile Val Val Leu Ile Val Leu Ile Cys His Lys Tyr Lys
            530             535             540
```

Fig. 1a.4

```
AAG CAA TTT AGG TAC GAG AGT CAG CTG CAG ATG ATC CAG GTG ACT GGC
Lys Gln Phe Arg Tyr Glu Ser Gln Leu Gln Met Ile Gln Val Thr Gly
            545                 550                 555

CCC CTG GAT AAC GAG TAC TTC TAC GTT GAC TTC AGG GAC TAT GAA TAT
Pro Leu Asp Asn Glu Tyr Phe Tyr Val Asp Phe Arg Asp Tyr Glu Tyr
            560                 565                 570

GAC CTT AAG TGG GAG TTC CCG AGA GAG AAC TTA GAG TTT GGG AAG GTC
Asp Leu Lys Trp Glu Phe Pro Arg Glu Asn Leu Glu Phe Gly Lys Val
            575                 580                 585

CTG GGG TCT GGC GCT TTC GGG AGG GTG ATG AAC GCC ACG GCC TAT GGC
Leu Gly Ser Gly Ala Phe Gly Arg Val Met Asn Ala Thr Ala Tyr Gly
590                 595                 600                 605

ATT AGT AAA ACG GGA GTC TCA ATT CAG GTG GCG GTG AAG ATG CTA AAA
Ile Ser Lys Thr Gly Val Ser Ile Gln Val Ala Val Lys Met Leu Lys
                    610                 615                 620

GAG AAA GCT GAC AGC TGT GAA AAA GAA GCT CTC ATG TCG GAG CTC AAA
Glu Lys Ala Asp Ser Cys Glu Lys Glu Ala Leu Met Ser Glu Leu Lys
                625                 630                 635

ATG ATG ACC CAC CTG GGA CAC CAT GAC AAC ATC GTG AAT CTG CTG GGG
Met Met Thr His Leu Gly His His Asp Asn Ile Val Asn Leu Leu Gly
            640                 645                 650

GCA TGC ACA CTG TCA GGG CCA GTG TAC TTG ATT TTT GAA TAT TGT TGC
Ala Cys Thr Leu Ser Gly Pro Val Tyr Leu Ile Phe Glu Tyr Cys Cys
655                 660                 665

TAT GGT GAC CTC CTC AAC TAC CTA AGA AGT AAA AGA GAG AAG TTT CAC
Tyr Gly Asp Leu Leu Asn Tyr Leu Arg Ser Lys Arg Glu Lys Phe His
670                 675                 680                 685

AGG ACA TGG ACA GAG ATT TTT AAG GAA CAT AAT TTC AGT TCT TAC CCT
Arg Thr Trp Thr Glu Ile Phe Lys Glu His Asn Phe Ser Ser Tyr Pro
                690                 695                 700

ACT TTC CAG GCA CAT TCA AAT TCC AGC ATG CCT GGT TCA CGA GAA GTT
Thr Phe Gln Ala His Ser Asn Ser Ser Met Pro Gly Ser Arg Glu Val
            705                 710                 715

CAG TTA CAC CCG CCC TTG GAT CAG CTC TCA GGG TTC AAT GGG AAT TCA
Gln Leu His Pro Pro Leu Asp Gln Leu Ser Gly Phe Asn Gly Asn Ser
            720                 725                 730
```

Fig. 1a.5

```
ATT CAT TCT GAA GAT GAG ATT GAA TAT GAA AAC CAG AAG AGG CTG GCA
Ile His Ser Glu Asp Glu Ile Glu Tyr Glu Asn Gln Lys Arg Leu Ala
    735             740             745

GAA GAA GAG GAG GAA GAT TTG AAC GTG CTG ACG TTT GAA GAC CTC CTT
Glu Glu Glu Glu Glu Asp Leu Asn Val Leu Thr Phe Glu Asp Leu Leu
750             755             760             765

TGC TTT GCG TAC CAA GTG GCC AAA GGC ATG GAA TTC CTG GAG TTC AAG
Cys Phe Ala Tyr Gln Val Ala Lys Gly Met Glu Phe Leu Glu Phe Lys
            770             775             780

TCG TGT GTC CAC AGA GAC CTG GCA GCC AGG AAT GTG TTG GTC ACC CAC
Ser Cys Val His Arg Asp Leu Ala Ala Arg Asn Val Leu Val Thr His
        785             790             795

GGG AAG GTG GTG AAG ATC TGT GAC TTT GGA CTG GCC CGA GAC ATC CTG
Gly Lys Val Val Lys Ile Cys Asp Phe Gly Leu Ala Arg Asp Ile Leu
        800             805             810

AGC GAC TCC AGC TAC GTC GTC AGG GGC AAC GCA CGG CTG CCG GTG AAG
Ser Asp Ser Ser Tyr Val Val Arg Gly Asn Ala Arg Leu Pro Val Lys
815             820             825

TGG ATG GCA CCC GAG AGC TTA TTT GAA GGG ATC TAC ACA ATC AAG AGT
Trp Met Ala Pro Glu Ser Leu Phe Glu Gly Ile Tyr Thr Ile Lys Ser
830             835             840             845

GAC GTC TGG TCC TAC GGC ATC CTT CTC TGG GAG ATA TTT TCA CTG GGT
Asp Val Trp Ser Tyr Gly Ile Leu Leu Trp Glu Ile Phe Ser Leu Gly
            850             855             860

GTG AAC CCT TAC CCT GGC ATT CCT GTC GAC GCT AAC TTC TAT AAA CTG
Val Asn Pro Tyr Pro Gly Ile Pro Val Asp Ala Asn Phe Tyr Lys Leu
            865             870             875

ATT CAG AGT GGA TTT AAA ATG GAG CAG CCA TTC TAT GCC ACA GAA GGG
Ile Gln Ser Gly Phe Lys Met Glu Gln Pro Phe Tyr Ala Thr Glu Gly
        880             885             890

ATA TAC TTT GTA ATG CAA TCC TGC TGG GCT TTT GAC TCA AGG AAG CGG
Ile Tyr Phe Val Met Gln Ser Cys Trp Ala Phe Asp Ser Arg Lys Arg
    895             900             905
```

Fig. 1a.6

```
CCA TCC TTC CCC AAC CTG ACT TCA TTT TTA GGA TGT CAG CTG GCA GAG
Pro Ser Phe Pro Asn Leu Thr Ser Phe Leu Gly Cys Gln Leu Ala Glu
910                 915                 920                 925

GCA GAA GAA GCA TGT ATC AGA ACA TCC ATC CAT CTA CCA AAA CAG GCG
Ala Glu Glu Ala Cys Ile Arg Thr Ser Ile His Leu Pro Lys Gln Ala
                930                 935                 940

GCC CCT CAG CAG AGA GGC GGG CTC AGA GCC CAG TCG CCA CAG CGC CAG
Ala Pro Gln Gln Arg Gly Gly Leu Arg Ala Gln Ser Pro Gln Arg Gln
                945                 950                 955

GTG AAG ATT CAC AGA GAA AGA AGT TAGCGAGGAG GCCTTGGACC CCGCCACCCT
Val Lys Ile His Arg Glu Arg Ser
                960             965
```

AGCAGGCTGT AGACCGCAGA GCCAAGATTA GCCTCGCCTC TGAGGAAGCG CCCTACAGCG

CGTTGCTTCG CTGGACTTTT CTCTAGATGC TGTCTGCCAT TACTCCAAAG TGACTTCTAT

AAAATCAAAC CTCTCCTCGC ACAGGCGGGA GAGCCAATAA TGAGACTTGT TGGTGAGCCC

GCCTACCCTG GGGGCCTTTC CACGAGCTTG AGGGGAAAGC CATGTATCTG AAATATAGTA

TATTCTTGTA AATACGTGAA ACAAACCAAA CCCGTTTTTT GCTAAGGGAA AGCTAAATAT

GATTTTTAAA AATCTATGTT TTAAAATACT ATGTAACTTT TTCATCTATT TAGTGATATA

TTTTATGGAT GGAAATAAAC TTTCTACTGT AAAAAAAAAA AAAAAAAAA AAAAAA

Fig. 1b.1

```
CGAGGCGGCA TCCGAGGGCT GGGCCGGCGC CCTGGGGGAC CCCGGGCTCC GGAGGCC

ATG CCG GCG TTG GCG CGC GAC GCG GGC ACC GTG CCG CTG CTC GTT GTT
Met Pro Ala Leu Ala Arg Asp Ala Gly Thr Val Pro Leu Leu Val Val
-27     -25             -20                 -15

TTT TCT GCA ATG ATA TTT GGG ACT ATT ACA AAT CAA GAT CTG CCT GTG
Phe Ser Ala Met Ile Phe Gly Thr Ile Thr Asn Gln Asp Leu Pro Val
        -10             -5                  1                 5

ATC AAG TGT GTT TTA ATC AAT CAT AAG AAC AAT GAT TCA TCA GTG GGG
Ile Lys Cys Val Leu Ile Asn His Lys Asn Asn Asp Ser Ser Val Gly
                10                  15                  20

AAG TCA TCA TCA TAT CCC ATG GTA TCA GAA TCC CCG GAA GAC CTC GGG
Lys Ser Ser Ser Tyr Pro Met Val Ser Glu Ser Pro Glu Asp Leu Gly
            25                  30                  35

TGT GCG TTG AGA CCC CAG AGC TCA GGG ACA GTG TAC GAA GCT GCC GCT
Cys Ala Leu Arg Pro Gln Ser Ser Gly Thr Val Tyr Glu Ala Ala Ala
        40                  45                  50

GTG GAA GTG GAT GTA TCT GCT TCC ATC ACA CTG CAA GTG CTG GTC GAT
Val Glu Val Asp Val Ser Ala Ser Ile Thr Leu Gln Val Leu Val Asp
    55                  60                  65

GCC CCA GGG AAC ATT TCC TGT CTC TGG GTC TTT AAG CAC AGC TCC CTG
Ala Pro Gly Asn Ile Ser Cys Leu Trp Val Phe Lys His Ser Ser Leu
70                  75                  80                  85

AAT TGC CAG CCA CAT TTT GAT TTA CAA AAC AGA GGA GTT GTT TCC ATG
Asn Cys Gln Pro His Phe Asp Leu Gln Asn Arg Gly Val Val Ser Met
                90                  95                  100

GTC ATT TTG AAA ATG ACA GAA ACC CAA GCT GGA GAA TAC CTA CTT TTT
Val Ile Leu Lys Met Thr Glu Thr Gln Ala Gly Glu Tyr Leu Leu Phe
            105                 110                 115

ATT CAG AGT GAA GCT ACC AAT TAC ACA ATA TTG TTT ACA GTG AGT ATA
Ile Gln Ser Glu Ala Thr Asn Tyr Thr Ile Leu Phe Thr Val Ser Ile
        120                 125                 130

AGA AAT ACC CTG CTT TAC ACA TTA AGA AGA CCT TAC TTT AGA AAA ATG
Arg Asn Thr Leu Leu Tyr Thr Leu Arg Arg Pro Tyr Phe Arg Lys Met
        135                 140                 145
```

Fig. 1b.2

```
GAA AAC CAG GAC GCC CTG GTC TGC ATA TCT GAG AGC GTT CCA GAG CCG
Glu Asn Gln Asp Ala Leu Val Cys Ile Ser Glu Ser Val Pro Glu Pro
150             155             160             165

ATC GTG GAA TGG GTG CTT TGC GAT TCA CAG GGG GAA AGC TGT AAA GAA
Ile Val Glu Trp Val Leu Cys Asp Ser Gln Gly Glu Ser Cys Lys Glu
            170             175             180

GAA AGT CCA GCT GTT GTT AAA AAG GAG GAA AAA GTG CTT CAT GAA TTA
Glu Ser Pro Ala Val Val Lys Lys Glu Glu Lys Val Leu His Glu Leu
        185             190             195

TTT GGG ACG GAC ATA AGG TGC TGT GCC AGA AAT GAA CTG GGC AGG GAA
Phe Gly Thr Asp Ile Arg Cys Cys Ala Arg Asn Glu Leu Gly Arg Glu
    200             205             210

TGC ACC AGG CTG TTC ACA ATA GAT CTA AAT CAA ACT CCT CAG ACC ACA
Cys Thr Arg Leu Phe Thr Ile Asp Leu Asn Gln Thr Pro Gln Thr Thr
215             220             225

TTG CCA CAA TTA TTT CTT AAA GTA GGG GAA CCC TTA TGG ATA AGG TGC
Leu Pro Gln Leu Phe Leu Lys Val Gly Glu Pro Leu Trp Ile Arg Cys
230             235             240             245

AAA GCT GTT CAT GTG AAC CAT GGA TTC GGG CTC ACC TGG GAA TTA GAA
Lys Ala Val His Val Asn His Gly Phe Gly Leu Thr Trp Glu Leu Glu
            250             255             260

AAC AAA GCA CTC GAG GAG GGC AAC TAC TTT GAG ATG AGT ACC TAT TCA
Asn Lys Ala Leu Glu Glu Gly Asn Tyr Phe Glu Met Ser Thr Tyr Ser
        265             270             275

ACA AAC AGA ACT ATG ATA CGG ATT CTG TTT GCT TTT GTA TCA TCA GTG
Thr Asn Arg Thr Met Ile Arg Ile Leu Phe Ala Phe Val Ser Ser Val
    280             285             290

GCA AGA AAC GAC ACC GGA TAC TAC ACT TGT TCC TCT TCA AAG CAT CCC
Ala Arg Asn Asp Thr Gly Tyr Tyr Thr Cys Ser Ser Ser Lys His Pro
295             300             305

AGT CAA TCA GCT TTG GTT ACC ATC GTA GGA AAG GGA TTT ATA AAT GCT
Ser Gln Ser Ala Leu Val Thr Ile Val Gly Lys Gly Phe Ile Asn Ala
310             315             320             325

ACC AAT TCA AGT GAA GAT TAT GAA ATT GAC CAA TAT GAA GAG TTT TGT
Thr Asn Ser Ser Glu Asp Tyr Glu Ile Asp Gln Tyr Glu Glu Phe Cys
            330             335             340
```

Fig. 1b.3

```
TTT TCT GTC AGG TTT AAA GCC TAC CCA CAA ATC AGA TGT ACG TGG ACC
Phe Ser Val Arg Phe Lys Ala Tyr Pro Gln Ile Arg Cys Thr Trp Thr
        345             350             355

TTC TCT CGA AAA TCA TTT CCT TGT GAG CAA AAG GGT CTT GAT AAC GGA
Phe Ser Arg Lys Ser Phe Pro Cys Glu Gln Lys Gly Leu Asp Asn Gly
        360             365             370

TAC AGC ATA TCC AAG TTT TGC AAT CAT AAG CAC CAG CCA GGA GAA TAT
Tyr Ser Ile Ser Lys Phe Cys Asn His Lys His Gln Pro Gly Glu Tyr
        375             380             385

ATA TTC CAT GCA GAA AAT GAT GAT GCC CAA TTT ACC AAA ATG TTC ACG
Ile Phe His Ala Glu Asn Asp Asp Ala Gln Phe Thr Lys Met Phe Thr
390             395             400             405

CTG AAT ATA AGA AGG AAA CCT CAA GTG CTC GCA GAA GCA TCG GCA AGT
Leu Asn Ile Arg Arg Lys Pro Gln Val Leu Ala Glu Ala Ser Ala Ser
            410             415             420

CAG GCG TCC TGT TTC TCG GAT GGA TAC CCA TTA CCA TCT TGG ACC TGG
Gln Ala Ser Cys Phe Ser Asp Gly Tyr Pro Leu Pro Ser Trp Thr Trp
            425             430             435

AAG AAG TGT TCA GAC AAG TCT CCC AAC TGC ACA GAA GAG ATC ACA GAA
Lys Lys Cys Ser Asp Lys Ser Pro Asn Cys Thr Glu Glu Ile Thr Glu
        440             445             450

GGA GTC TGG AAT AGA AAG GCT AAC AGA AAA GTG TTT GGA CAG TGG GTG
Gly Val Trp Asn Arg Lys Ala Asn Arg Lys Val Phe Gly Gln Trp Val
    455             460             465

TCG AGC AGT ACT CTA AAC ATG AGT GAA GCC ATA AAA GGG TTC CTG GTC
Ser Ser Ser Thr Leu Asn Met Ser Glu Ala Ile Lys Gly Phe Leu Val
470             475             480             485

AAG TGC TGT GCA TAC AAT TCC CTT GGC ACA TCT TGT GAG ACG ATC CTT
Lys Cys Cys Ala Tyr Asn Ser Leu Gly Thr Ser Cys Glu Thr Ile Leu
            490             495             500

TTA AAC TCT CCA GGC CCC TTC CCT TTC ATC CAA GAC AAC ATC TCA TTC
Leu Asn Ser Pro Gly Pro Phe Pro Phe Ile Gln Asp Asn Ile Ser Phe
        505             510             515

TAT GCA ACA ATT GGT GTT TGT CTC CTC TTC ATT GTC GTT TTA ACC CTG
Tyr Ala Thr Ile Gly Val Cys Leu Leu Phe Ile Val Val Leu Thr Leu
        520             525             530
```

Fig. 1b.4

```
CTA ATT TGT CAC AAG TAC AAA AAG CAA TTT AGG TAT GAA AGC CAG CTA
Leu Ile Cys His Lys Tyr Lys Lys Gln Phe Arg Tyr Glu Ser Gln Leu
    535             540                 545

CAG ATG GTA CAG GTG ACC GGC TCC TCA GAT AAT GAG TAC TTC TAC GTT
Gln Met Val Gln Val Thr Gly Ser Ser Asp Asn Glu Tyr Phe Tyr Val
550             555                 560                 565

GAT TTC AGA GAA TAT GAA TAT GAT CTC AAA TGG GAG TTT CCA AGA GAA
Asp Phe Arg Glu Tyr Glu Tyr Asp Leu Lys Trp Glu Phe Pro Arg Glu
                570             575                 580

AAT TTA GAG TTT GGG AAG GTA CTA GGA TCA GGT GCT TTT GGA AAA GTG
Asn Leu Glu Phe Gly Lys Val Leu Gly Ser Gly Ala Phe Gly Lys Val
            585             590                 595

ATG AAC GCA ACA GCT TAT GGA ATT AGC AAA ACA GGA GTC TCA ATC CAG
Met Asn Ala Thr Ala Tyr Gly Ile Ser Lys Thr Gly Val Ser Ile Gln
            600             605             610

GTT GCC GTC AAA ATG CTG AAA GAA AAA GCA GAC AGC TCT GAA AGA GAG
Val Ala Val Lys Met Leu Lys Glu Lys Ala Asp Ser Ser Glu Arg Glu
615             620             625

GCA CTC ATG TCA GAA CTC AAG ATG ATG ACC CAG CTG GGA AGC CAC GAG
Ala Leu Met Ser Glu Leu Lys Met Met Thr Gln Leu Gly Ser His Glu
630             635             640             645

AAT ATT GTG AAC CTG CTG GGG GCG TGC ACA CTG TCA GGA CCA ATT TAC
Asn Ile Val Asn Leu Leu Gly Ala Cys Thr Leu Ser Gly Pro Ile Tyr
            650             655             660

TTG ATT TTT GAA TAC TGT TGC TAT GGT GAT CTT CTC AAC TAT CTA AGA
Leu Ile Phe Glu Tyr Cys Cys Tyr Gly Asp Leu Leu Asn Tyr Leu Arg
            665             670             675

AGT AAA AGA GAA AAA TTT CAC AGG ACT TGG ACA GAG ATT TTC AAG GAA
Ser Lys Arg Glu Lys Phe His Arg Thr Trp Thr Glu Ile Phe Lys Glu
        680             685             690

CAC AAT TTC AGT TTT TAC CCC ACT TTC CAA TCA CAT CCA AAT TCC AGC
His Asn Phe Ser Phe Tyr Pro Thr Phe Gln Ser His Pro Asn Ser Ser
        695             700             705

ATG CCT GGT TCA AGA GAA GTT CAG ATA CAC CCG GAC TCG GAT CAA ATC
Met Pro Gly Ser Arg Glu Val Gln Ile His Pro Asp Ser Asp Gln Ile
710             715             720             725
```

Fig. 1b.5

```
TCA GGG CTT CAT GGG AAT TCA TTT CAC TCT GAA GAT GAA ATT GAA TAT
Ser Gly Leu His Gly Asn Ser Phe His Ser Glu Asp Glu Ile Glu Tyr
            730                 735                 740

GAA AAC CAA AAA AGG CTG GAA GAA GAG GAG GAC TTG AAT GTG CTT ACA
Glu Asn Gln Lys Arg Leu Glu Glu Glu Glu Asp Leu Asn Val Leu Thr
            745                 750                 755

TTT GAA GAT CTT CTT TGC TTT GCA TAT CAA GTT GCC AAA GGA ATG GAA
Phe Glu Asp Leu Leu Cys Phe Ala Tyr Gln Val Ala Lys Gly Met Glu
            760                 765                 770

TTT CTG GAA TTT AAG TCG TGT GTT CAC AGA GAC CTG GCC GCC AGG AAC
Phe Leu Glu Phe Lys Ser Cys Val His Arg Asp Leu Ala Ala Arg Asn
            775                 780                 785

GTG CTT GTC ACC CAC GGG AAA GTG GTG AAG ATA TGT GAC TTT GGA TTG
Val Leu Val Thr His Gly Lys Val Val Lys Ile Cys Asp Phe Gly Leu
790                 795                 800                 805

CCT CGA GAT ATC ATG AGT GAT TCC AAC TAT GTT GTC AGG GGC AAT GCC
Ala Arg Asp Ile Met Ser Asp Ser Asn Tyr Val Val Arg Gly Asn Ala
            810                 815                 820

CGT CTG CCT GTA AAA TGG ATG GCC CCC GAA AGC CTG TTT GAA GGC ATC
Arg Leu Pro Val Lys Trp Met Ala Pro Glu Ser Leu Phe Glu Gly Ile
            825                 830                 835

TAC ACC ATT AAG AGT GAT GTC TGG TCA TAT GGA ATA TTA CTG TGG GAA
Tyr Thr Ile Lys Ser Asp Val Trp Ser Tyr Gly Ile Leu Leu Trp Glu
            840                 845                 850

ATC TTC TCA CTT GGT GTG AAT CCT TAC CCT GGC ATT CCG GTT GAT GCT
Ile Phe Ser Leu Gly Val Asn Pro Tyr Pro Gly Ile Pro Val Asp Ala
            855                 860                 865

AAC TTC TAC AAA CTG ATT CAA AAT GGA TTT AAA ATG GAT CAG CCA TTT
Asn Phe Tyr Lys Leu Ile Gln Asn Gly Phe Lys Met Asp Gln Pro Phe
870                 875                 880                 885

TAT GCT ACA GAA GAA ATA TAC ATT ATA ATG CAA TCC TGC TGG GCT TTT
Tyr Ala Thr Glu Glu Ile Tyr Ile Ile Met Gln Ser Cys Trp Ala Phe
            890                 895                 900

GAC TCA AGG AAA CGG CCA TCC TTC CCT AAT TTG ACT TCG TTT TTA GGA
Asp Ser Arg Lys Arg Pro Ser Phe Pro Asn Leu Thr Ser Phe Leu Gly
            905                 910                 915
```

Fig. 1b.6

```
TGT CAG CTG GCA GAT GCA GAA GAA GCG ATG TAT CAG AAT GTG GAT GGC
Cys Gln Leu Ala Asp Ala Glu Glu Ala Met Tyr Gln Asn Val Asp Gly
        920                 925                 930

CGT GTT TCG GAA TGT CCT CAC ACC TAC CAA AAC AGG CGA CCT TTC AGC
Arg Val Ser Glu Cys Pro His Thr Tyr Gln Asn Arg Arg Pro Phe Ser
        935                 940                 945

AGA GAG ATG GAT TTG GGG CTA CTC TCT CCG CAG GCT CAG GTC GAA GAT
Arg Glu Met Asp Leu Gly Leu Leu Ser Pro Gln Ala Gln Val Glu Asp
950                 955                 960                 965

TCG TAGAGGAACA ATTTAGTTTT AAGGACTTCA TCCCTCCACC TATCCCTAAC
Ser

AGGCTGTAGA TTACCAAAAC AAGATTAATT TCATCACTAA AAGAAAATCT ATTATCAACT

GCTGCTTCAC CAGACTTTTC TCTAGAAGCC GTCTGCGTTT ACTCTTGTTT TCAAAGGGAC

TTTTGTAAAA TCAAATCATC CTGTCACAAG GCAGGAGGAG CTGATAATGA ACTTTATTGG

AGCATTGATC TGCATCCAAG GCCTTCTCAG GCCGGCTTGA GTGAATTGTG TACCTGAAGT

ACAGTATATT CTTGTAAATA CATAAAACAA AAGCATTTTG CTAAGGAGAA GCTAATATGA

TTTTTTAAGT CTATGTTTTA AAATAATATG TAAATTTTTC AGCTATTTAG TGATATATTT

TATGGGTGGG AATAAAATTT CTACTACAGA AAAAAAAAAA AAAAAAAAAA AAAAA
```

Fig. 2.1

CTGTGTCCCG CAGCCGGATA ACCTGGCTGA CCCGATTCCG CGGACACCCG TGCAGCCGCG

GCTGGAGCCA GGGCGCCGGT GCCCGCGCTC TCCCCGGTCT TCCGCTGCGG GGGCCGATAC

CGCCTCTGTG ACTTCTTTGC GGGCCAGGGA CGGAGAAGGA GTCTGTGCCT GAGAAACTGG

GCTCTGTGCC CAGGCGCGAG GTGCAGG ATG GAG AGC AAG GGC CTG CTA GCT
              Met Glu Ser Lys Gly Leu Leu Ala
              -19      -15

```
GTC GCT CTG TGG TTC TGC GTG GAG ACC CGA GCC GCC TCT GTG GGT TTG
Val Ala Leu Trp Phe Cys Val Glu Thr Arg Ala Ala Ser Val Gly Leu
    -10              -5                   1                5

CCT GGC GAT TTT CTC CAT CCC CCC AAG CTC AGC ACA CAG AAA GAC ATA
Pro Gly Asp Phe Leu His Pro Pro Lys Leu Ser Thr Gln Lys Asp Ile
             10                  15                  20

CTG ACA ATT TTG GCA AAT ACA ACC CTT CAG ATT ACT TGC AGG GGA CAG
Leu Thr Ile Leu Ala Asn Thr Thr Leu Gln Ile Thr Cys Arg Gly Gln
             25                  30                  35

CGG GAC CTG GAC TGG CTT TGG CCC AAT GCT CAG CGT GAT TCT GAG GAA
Arg Asp Leu Asp Trp Leu Trp Pro Asn Ala Gln Arg Asp Ser Glu Glu
             40                  45                  50

AGG GTA TTG GTG ACT GAA TGC GGC GGT GGT GAC AGT ATC TTC TGC AAA
Arg Val Leu Val Thr Glu Cys Gly Gly Gly Asp Ser Ile Phe Cys Lys
     55                  60                  65

ACA CTC ACC ATT CCC AGG GTG GTT GGA AAT GAT ACT GGA GCC TAC AAG
Thr Leu Thr Ile Pro Arg Val Val Gly Asn Asp Thr Gly Ala Tyr Lys
 70                  75                  80                  85

TGC TCG TAC CGG GAC GTC GAC ATA GCC TCC ACT GTT TAT GTC TAT GTT
Cys Ser Tyr Arg Asp Val Asp Ile Ala Ser Thr Val Tyr Val Tyr Val
             90                  95                  100

CGA GAT TAC AGA TCA CCA TTC ATC GCC TCT GTC AGT GAC CAG CAT GGC
Arg Asp Tyr Arg Ser Pro Phe Ile Ala Ser Val Ser Asp Gln His Gly
             105                 110                 115

ATC GTG TAC ATC ACC GAG AAC AAG AAC AAA ACT GTG GTG ATC CCC TGC
Ile Val Tyr Ile Thr Glu Asn Lys Asn Lys Thr Val Val Ile Pro Cys
         120                 125                 130
```

Fig. 2.2

```
CGA GGG TCG ATT TCA AAC CTC AAT GTG TCT CTT TGC GCT AGG TAT CCA
Arg Gly Ser Ile Ser Asn Leu Asn Val Ser Leu Cys Ala Arg Tyr Pro
    135                 140                 145

GAA AAG AGA TTT GTT CCG GAT GGA AAC AGA ATT TCC TGG GAC AGC GAG
Glu Lys Arg Phe Val Pro Asp Gly Asn Arg Ile Ser Trp Asp Ser Glu
150                 155                 160                 165

ATA GGC TTT ACT CTC CCC AGT TAC ATG ATC AGC TAT GCC GGC ATG GTC
Ile Gly Phe Thr Leu Pro Ser Tyr Met Ile Ser Tyr Ala Gly Met Val
            170                 175                 180

TTC TGT GAG GCA AAG ATC AAT GAT GAA ACC TAT CAG TCT ATC ATG TAC
Phe Cys Glu Ala Lys Ile Asn Asp Glu Thr Tyr Gln Ser Ile Met Tyr
                185                 190                 195

ATA GTT GTG GTT GTA GGA TAT AGG ATT TAT GAT GTG ATT CTG AGC CCC
Ile Val Val Val Val Gly Tyr Arg Ile Tyr Asp Val Ile Leu Ser Pro
        200                 205                 210

CCG CAT GAA ATT GAG CTA TCT GCC GGA GAA AAA CTT GTC TTA AAT TGT
Pro His Glu Ile Glu Leu Ser Ala Gly Glu Lys Leu Val Leu Asn Cys
    215                 220                 225

ACA GCG AGA ACA GAG CTC AAT GTG GGG CTT GAT TTC ACC TGG CAC TCT
Thr Ala Arg Thr Glu Leu Asn Val Gly Leu Asp Phe Thr Trp His Ser
230                 235                 240                 245

CCA CCT TCA AAG TCT CAT CAT AAG AAG ATT GTA AAC CGG GAT GTG AAA
Pro Pro Ser Lys Ser His His Lys Lys Ile Val Asn Arg Asp Val Lys
            250                 255                 260

CCC TTT CCT GGG ACT GTG GCG AAG ATG TTT TTG AGC ACC TTG ACA ATA
Pro Phe Pro Gly Thr Val Ala Lys Met Phe Leu Ser Thr Leu Thr Ile
                265                 270                 275

GAA AGT GTG ACC AAG AGT GAC CAA GGG GAA TAC ACC TGT GTA GCG TCC
Glu Ser Val Thr Lys Ser Asp Gln Gly Glu Tyr Thr Cys Val Ala Ser
        280                 285                 290

AGT GGA CGG ATG ATC AAG AGA AAT AGA ACA TTT GTC CGA GTT CAC ACA
Ser Gly Arg Met Ile Lys Arg Asn Arg Thr Phe Val Arg Val His Thr
    295                 300                 305

AAG CCT TTT ATT GCT TTC GGT AGT GGG ATG AAA TCT TTG GTG GAA GCC
Lys Pro Phe Ile Ala Phe Gly Ser Gly Met Lys Ser Leu Val Glu Ala
310                 315                 320                 325
```

Fig. 2.3

```
ACA GTG GGC AGT CAA GTC CGA ATC CCT GTG AAG TAT CTC AGT TAC CCA
Thr Val Gly Ser Gln Val Arg Ile Pro Val Lys Tyr Leu Ser Tyr Pro
                330                 335                 340

GCT CCT GAT ATC AAA TGG TAC AGA AAT GGA AGG CCC ATT GAG TCC AAC
Ala Pro Asp Ile Lys Trp Tyr Arg Asn Gly Arg Pro Ile Glu Ser Asn
                345                 350                 355

TAC ACA ATG ATT GTT GGC GAT GAA CTC ACC ATC ATG GAA GTG ACT GAA
Tyr Thr Met Ile Val Gly Asp Glu Leu Thr Ile Met Glu Val Thr Glu
            360                 365                 370

AGA GAT GCA GGA AAC TAC ACG GTC ATC CTC ACC AAC CCC ATT TCA ATG
Arg Asp Ala Gly Asn Tyr Thr Val Ile Leu Thr Asn Pro Ile Ser Met
    375                 380                 385

GAG AAA CAG AGC CAC ATG GTC TCT CTG GTT GTG AAT GTC CCA CCC CAG
Glu Lys Gln Ser His Met Val Ser Leu Val Val Asn Val Pro Pro Gln
390                 395                 400                 405

ATC GGT GAG AAA GCC TTG ATC TCG CCT ATG GAT TCC TAC CAG TAT GGG
Ile Gly Glu Lys Ala Leu Ile Ser Pro Met Asp Ser Tyr Gln Tyr Gly
                410                 415                 420

ACC ATG CAG ACA TTG ACA TGC ACA GTC TAC GCC AAC CCT CCC CTG CAC
Thr Met Gln Thr Leu Thr Cys Thr Val Tyr Ala Asn Pro Pro Leu His
                425                 430                 435

CAC ATC CAG TGG TAC TGG CAG CTA GAA GAA GCC TGC TCC TAC AGA CCC
His Ile Gln Trp Tyr Trp Gln Leu Glu Glu Ala Cys Ser Tyr Arg Pro
                440                 445                 450

GGC CAA ACA AGC CCG TAT GCT TGT AAA GAA TGG AGA CAC GTG GAG GAT
Gly Gln Thr Ser Pro Tyr Ala Cys Lys Glu Trp Arg His Val Glu Asp
    455                 460                 465

TTC CAG GGG GGA AAC AAG ATC GAA GTC ACC AAA AAC CAA TAT GCC CTG
Phe Gln Gly Gly Asn Lys Ile Glu Val Thr Lys Asn Gln Tyr Ala Leu
470                 475                 480                 485

ATT GAA GGA AAA AAC AAA ACT GTA AGT ACG CTG GTC ATC CAA GCT GCC
Ile Glu Gly Lys Asn Lys Thr Val Ser Thr Leu Val Ile Gln Ala Ala
                490                 495                 500

AAC GTG TCA GCG TTG TAC AAA TGT GAA GCC ATC AAC AAA GCG GGA CGA
Asn Val Ser Ala Leu Tyr Lys Cys Glu Ala Ile Asn Lys Ala Gly Arg
            505                 510                 515
```

Fig. 2.4

```
GGA GAG AGG GTC ATC TCC TTC CAT GTG ATC AGG GGT CCT GAA ATT ACT
Gly Glu Arg Val Ile Ser Phe His Val Ile Arg Gly Pro Glu Ile Thr
        520                 525                 530

CTG CAA CCT GCT GCC CAG CCA ACT GAG CAG GAG AGT GTG TCC CTG TTG
Val Gln Pro Ala Ala Gln Pro Thr Glu Gln Glu Ser Val Ser Leu Leu
        535                 540                 545

TGC ACT GCA GAC AGA AAT ACG TTT GAG AAC CTC ACG TGG TAC AAG CTT
Cys Thr Ala Asp Arg Asn Thr Phe Glu Asn Leu Thr Trp Tyr Lys Leu
550             555                 560                     565

GGC TCA CAG GCA ACA TCG GTC CAC ATG GGC GAA TCA CTC ACA CCA GTT
Gly Ser Gln Ala Thr Ser Val His Met Gly Glu Ser Leu Thr Pro Val
            570                 575                 580

TGC AAG AAC TTG GAT GCT CTT TGG AAA CTG AAT GGC ACC ATG TTT TCT
Cys Lys Asn Leu Asp Ala Leu Trp Lys Leu Asn Gly Thr Met Phe Ser
            585                 590                 595

AAC AGC ACA AAT GAC ATC TTG ATT GTG GCA TTT CAG AAT GCC TCT CTG
Asn Ser Thr Asn Asp Ile Leu Ile Val Ala Phe Gln Asn Ala Ser Leu
        600                 605                 610

CAG GAC CAA GGC GAC TAT GTT TGC TCT GCT CAA GAT AAG AAG ACC AAG
Gln Asp Gln Gly Asp Tyr Val Cys Ser Ala Gln Asp Lys Lys Thr Lys
        615                 620                 625

AAA AGA CAT TGC CTG GTC AAA CAG CTC ATC ATC CTA GAG CGC ATG GCA
Lys Arg His Cys Leu Val Lys Gln Leu Ile Ile Leu Glu Arg Met Ala
630                 635                 640                 645

CCC ATG ATC ACC GGA AAT CTG GAG AAT CAG ACA ACA ACC ATT GGC GAG
Pro Met Ile Thr Gly Asn Leu Glu Asn Gln Thr Thr Thr Ile Gly Glu
                650                 655                 660

ACC ATT GAA GTG ACT TGC CCA GCA TCT GGA AAT CCT ACC CCA CAC ATT
Thr Ile Glu Val Thr Cys Pro Ala Ser Gly Asn Pro Thr Pro His Ile
            665                 670                 675

ACA TGG TTC AAA GAC AAC GAG ACC CTG GTA GAA GAT TCA GGC ATT GTA
Thr Trp Phe Lys Asp Asn Glu Thr Leu Val Glu Asp Ser Gly Ile Val
        680                 685                 690

CTG AGA GAT GGG AAC CGG AAC CTG ACT ATC CGC AGG GTG AGG AAG GAG
Leu Arg Asp Gly Asn Arg Asn Leu Thr Ile Arg Arg Val Arg Lys Glu
        695                 700                 705
```

Fig. 2.5

```
GAT GGA GGC CTC TAC ACC TGC CAG GCC TGC AAT GTC CTT GGC TGT GCA
Asp Gly Gly Leu Tyr Thr Cys Gln Ala Cys Asn Val Leu Gly Cys Ala
710                 715                 720                 725

AGA GCG GAG ACG CTC TTC ATA ATA GAA GGT GCC CAG GAA AAG ACC AAC
Arg Ala Glu Thr Leu Phe Ile Ile Glu Gly Ala Gln Glu Lys Thr Asn
                    730                 735                 740

TTG GAA GTC ATT ATC CTC GTC GGC ACT GCA GTG ATT GCC ATG TTC TTC
Leu Glu Val Ile Ile Leu Val Gly Thr Ala Val Ile Ala Met Phe Phe
                745                 750                 755

TGG CTC CTT CTT GTC ATT CTC GTA CGG ACC GTT AAG CGG GCC AAT GAA
Trp Leu Leu Leu Val Ile Leu Val Arg Thr Val Lys Arg Ala Asn Glu
        760                 765                 770

GGG GAA CTG AAG ACA GGC TAC TTG TCT ATT GTC ATG GAT CCA GAT GAA
Gly Glu Leu Lys Thr Gly Tyr Leu Ser Ile Val Met Asp Pro Asp Glu
        775                 780                 785

TTG CCC TTG GAT GAG CGC TGT GAA CGC TTG CCT TAT GAT GCC AGC AAG
Leu Pro Leu Asp Glu Arg Cys Glu Arg Leu Pro Tyr Asp Ala Ser Lys
790                 795                 800                 805

TGG GAA TTC CCC AGG GAC CGG CTG AAA CTA GGA AAA CCT CTT GGC CGC
Trp Glu Phe Pro Arg Asp Arg Leu Lys Leu Gly Lys Pro Leu Gly Arg
                810                 815                 820

GGT GCC TTC GGC CAA GTG ATT GAG GCA GAC GCT TTT GGA ATT GAC AAG
Gly Ala Phe Gly Gln Val Ile Glu Ala Asp Ala Phe Gly Ile Asp Lys
                825                 830                 835

ACA GCG ACT TGC AAA ACA GTA GCC GTC AAG ATG TTG AAA GAA GGA GCA
Thr Ala Thr Cys Lys Thr Val Ala Val Lys Met Leu Lys Glu Gly Ala
        840                 845                 850

ACA CAC AGC GAG CAT CGA GCC CTC ATG TCT GAA CTC AAG ATC CTC ATC
Thr His Ser Glu His Arg Ala Leu Met Ser Glu Leu Lys Ile Leu Ile
        855                 860                 865

CAC ATT GGT CAC CAT CTC AAT GTG GTG AAC CTC CTA GGC GCC TGC ACC
His Ile Gly His His Leu Asn Val Val Asn Leu Leu Gly Ala Cys Thr
870                 875                 880                 885

AAG CCG GGA GGG CCT CTC ATG GTG ATT GTG GAA TTC TCG AAG TTT GGA
Lys Pro Gly Gly Pro Leu Met Val Ile Val Glu Phe Ser Lys Phe Gly
                890                 895                 900
```

Fig. 2.6

```
AAC CTA TCA ACT TAC TTA CGG GGC AAG AGA AAT GAA TTT GTT CCC TAT
Asn Leu Ser Thr Tyr Leu Arg Gly Lys Arg Asn Glu Phe Val Pro Tyr
            905             910                 915

AAG AGC AAA GGG GCA CGC TTC CGC CAG GGC AAG GAC TAC GTT GGG GAG
Lys Ser Lys Gly Ala Arg Phe Arg Gln Gly Lys Asp Tyr Val Gly Glu
            920             925                 930

CTC TCC GTG GAT CTG AAA AGA CGC TTG GAC AGC ATC ACC AGC AGC CAG
Leu Ser Val Asp Leu Lys Arg Arg Leu Asp Ser Ile Thr Ser Ser Gln
            935             940                 945

AGC TCT GCC AGC TCA GGC TTT GTT GAG GAG AAA TCG CTC AGT GAT GTA
Ser Ser Ala Ser Ser Gly Phe Val Glu Glu Lys Ser Leu Ser Asp Val
950             955             960                         965

GAG GAA GAA GAA GCT TCT GAA GAA CTG TAC AAG GAC TTC CTG ACC TTG
Glu Glu Glu Glu Ala Ser Glu Glu Leu Tyr Lys Asp Phe Leu Thr Leu
            970             975                 980

GAG CAT CTC ATC TGT TAC AGC TTC CAA GTG GCT AAG GGC ATG GAG TTC
Glu His Leu Ile Cys Tyr Ser Phe Gln Val Ala Lys Gly Met Glu Phe
            985             990                 995

TTG GCA TCA AGG AAG TGT ATC CAC AGG GAC CTG GCA GCA CGA AAC ATT
Leu Ala Ser Arg Lys Cys Ile His Arg Asp Leu Ala Ala Arg Asn Ile
            1000            1005                1010

CTC CTA TCG GAG AAG AAT GTG GTT AAG ATC TGT GAC TTC GGC TTG GCC
Leu Leu Ser Glu Lys Asn Val Val Lys Ile Cys Asp Phe Gly Leu Ala
            1015            1020                1025

CGG GAC ATT TAT AAA GAC CCG GAT TAT GTC AGA AAA GGA GAT GCC CGA
Arg Asp Ile Tyr Lys Asp Pro Asp Tyr Val Arg Lys Gly Asp Ala Arg
1030            1035            1040                        1045

CTC CCT TTG AAG TGG ATG GCC CCG GAA ACC ATT TTT GAC AGA GTA TAC
Leu Pro Leu Lys Trp Met Ala Pro Glu Thr Ile Phe Asp Arg Val Tyr
            1050            1055                1060

ACA ATT CAG AGC GAT GTG TGG TCT TTC GGT GTG TTG CTC TGG GAA ATA
Thr Ile Gln Ser Asp Val Trp Ser Phe Gly Val Leu Leu Trp Glu Ile
            1065            1070                1075

TTT TCC TTA GGT GCC TCC CCA TAC CCT GGG GTC AAG ATT GAT GAA GAA
Phe Ser Leu Gly Ala Ser Pro Tyr Pro Gly Val Lys Ile Asp Glu Glu
            1080            1085                1090
```

Fig. 2.7

```
TTT TGT AGG AGA TTG AAA GAA GGA ACT AGA ATG CGG GCT CCT GAC TAC
Phe Cys Arg Arg Leu Lys Glu Gly Thr Arg Met Arg Ala Pro Asp Tyr
    1095            1100                1105

ACT ACC CCA GAA ATG TAC CAG ACC ATG CTG GAC TGC TGG CAT GAG GAC
Thr Thr Pro Glu Met Tyr Gln Thr Met Leu Asp Cys Trp His Glu Asp
1110            1115                1120                1125

CCC AAC CAG AGA CCC TCG TTT TCA GAG TTG GTG GAG CAT TTG GGA AAC
Pro Asn Gln Arg Pro Ser Phe Ser Glu Leu Val Glu His Leu Gly Asn
                1130            1135                1140

CTC CTG CAA GCA AAT GCG CAG CAG GAT GGC AAA GAC TAT ATT GTT CTT
Leu Leu Gln Ala Asn Ala Gln Gln Asp Gly Lys Asp Tyr Ile Val Leu
            1145                1150                1155

CCA ATG TCA GAG ACA CTG AGC ATG GAA GAG GAT TCT GGA CTC TCC CTG
Pro Met Ser Glu Thr Leu Ser Met Glu Glu Asp Ser Gly Leu Ser Leu
        1160                1165                1170

CCT ACC TCA CCT GTT TCC TGT ATG GAG GAA GAG GAA GTG TGC GAC CCC
Pro Thr Ser Pro Val Ser Cys Met Glu Glu Glu Glu Val Cys Asp Pro
    1175                1180                1185

AAA TTC CAT TAT GAC AAC ACA GCA GGA ATC AGT CAT TAT CTC CAG AAC
Lys Phe His Tyr Asp Asn Thr Ala Gly Ile Ser His Tyr Leu Gln Asn
1190            1195                1200                1205

AGT AAG CGA AAG AGC CGG CCA GTG AGT GTA AAA ACA TTT GAA GAT ATC
Ser Lys Arg Lys Ser Arg Pro Val Ser Val Lys Thr Phe Glu Asp Ile
                1210            1215                1220

CCA TTG GAG GAA CCA GAA GTA AAA GTG ATC CCA GAT GAC AGC CAG ACA
Pro Leu Glu Glu Pro Glu Val Lys Val Ile Pro Asp Asp Ser Gln Thr
            1225                1230                1235

GAC AGT GGG ATG GTC CTT GCA TCA GAA GAG CTG AAA ACT CTG GAA GAC
Asp Ser Gly Met Val Leu Ala Ser Glu Glu Leu Lys Thr Leu Glu Asp
        1240                1245                1250

AGG AAC AAA TTA TCT CCA TCT TTT GGT GGA ATG ATG CCC AGT AAA AGC
Arg Asn Lys Leu Ser Pro Ser Phe Gly Gly Met Met Pro Ser Lys Ser
    1255                1260                1265

AGG GAG TCT GTG GCC TCG GAA GGC TCC AAC CAG ACC AGT GGC TAC CAG
Arg Glu Ser Val Ala Ser Glu Gly Ser Asn Gln Thr Ser Gly Tyr Gln
1270            1275                1280                1285
```

Fig. 2.8

```
TCT GGG TAT CAC TCA GAT GAC ACA GAC ACC ACC GTG TAC TCC AGC GAC
Ser Gly Tyr His Ser Asp Asp Thr Asp Thr Thr Val Tyr Ser Ser Asp
            1290            1295                    1300

GAG GCA GGA CTT TTA AAG ATG GTG GAT GCT GCA GTT CAC GCT GAC TCA
Glu Ala Gly Leu Leu Lys Met Val Asp Ala Ala Val His Ala Asp Ser
            1305            1310                    1315

GGG ACC ACA CTG CAG CTC ACC TCC TGT TTA AAT GGA AGT GGT CCT GTC
Gly Thr Thr Leu Gln Leu Thr Ser Cys Leu Asn Gly Ser Gly Pro Val
            1320            1325                    1330

CCG GCT CCG CCC CCA ACT CCT GGA AAT CAC GAG AGA GGT GCT GCT TAG
Pro Ala Pro Pro Pro Thr Pro Gly Asn His Glu Arg Gly Ala Ala
            1335            1340                    1345
```

```
ATTTTCAAGT GTTGTTCTTT CCACCACCCG GAAGTAGCCA CATTTGATTT TCATTTTTGG
AGGAGGGACC TCAGACTGCA AGGAGCTTGT CCTCAGGGCA TTTCCAGAGA AGATGCCCAT
GACCCAAGAA TGTGTTGACT CTACTCTCTT TTCCATTCAT TTAAAAGTCC TATATAATGT
GCCCTGCTGT GGTCTCACTA CCAGTTAAAG CAAAAGACTT TCAAACACGT GGACTCTGTC
CTCCAAGAAG TGGCAACGGC ACCTCTGTGA AACTGGATCG AATGGGCAAT GCTTTGTGTG
TTGAGGATGG GTGAGATGTC CCAGGGCCGA GTCTGTCTAC CTTGGAGGCT TTGTGGAGGA
TGCGGCTATG AGCCAAGTGT TAAGTGTGGG ATGTGGACTG GGAGGAAGGA AGGCGCAAGC
CGTCCGGAGA GCGGTTGGAG CCTGCAGATG CATTGTGCTG GCTCTGGTGG AGGTGGGCTT
GTGGCCTGTC AGGAAACGCA AAGGCGGCCG GCAGGGTTTG GTTTTGGAAG GTTTGCGTGC
TCTTCACAGT CGGGTTACAG GCGAGTTCCC TGTGGCGTTT CCTACTCCTA ATGAGAGTTC
CTTCCGGACT CTTACGTGTC TCCTGGCCTG GCCCCAGGAA GGAAATGATG CAGCTTGCTC
CTTCCTCATC TCTCAGGCTG TGCCTTAATT CAGAACACCA AAAGAGAGGA ACGTCGGCAG
AGGCTCCTGA CGGGGCCGAA GAATTGTGAG AACAGAACAG AAACTCAGGG TTTCTGCTGG
GTGGAGACCC ACGTGGCGCC CTGGTGGCAG GTCTGAGGGT TCTCTGTCAA GTGGCGGTAA
AGGCTCAGGC TGGTGTTCTT CCTCTATCTC CACTCCTGTC AGGCCCCAA GTCCTCAGTA
TTTTAGCTTT GTGGCTTCCT GATGGCAGAA AAATCTTAAT TGGTTGGTTT GCTCTCCAGA
```

Fig. 29

TAATCACTAG CCAGATTTCG AAATTACTTT TTAGCCGAGG TTATGATAAC ATCTACTGTA
TCCTTTAGAA TTTTAACCTA TAAAACTATG TCTACTGGTT TCTGCCTGTG TGCTTATGTT
AAAAAAAAAA AAAAA

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 3453 base pairs
      (B) TYPE: nucleic acid
      (C) STRANDEDNESS: double

```
          (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
          (A) NAME/KEY: mat_peptide
          (B) LOCATION: 112..3006

(ix) FEATURE:
          (A) NAME/KEY: sig_peptide
          (B) LOCATION: 31..111

(ix) FEATURE:
          (A) NAME/KEY: CDS
          (B) LOCATION: 31..3009

(xi) SEQUENCE DESCRIPTION: SEQ ID NO: 1:

GCGGCCTGGC TACCGCGCGC TCCGGAGGCC ATG CGG GCG TTG GCG CAG CGC AGC        54
                                 Met Arg Ala Leu Ala Gln Arg Ser
                                 -27     -25                 -20

GAC CGG CGG CTG CTG CTG CTT GTT GTT TTG TCA GTA ATG ATT CTT GAG        102
Asp Arg Arg Leu Leu Leu Leu Val Val Leu Ser Val Met Ile Leu Glu
            -15                 -10                  -5

ACC GTT ACA AAC CAA GAC CTG CCT GTG ATC AAG TGT GTT TTA ATC AGT        150
Thr Val Thr Asn Gln Asp Leu Pro Val Ile Lys Cys Val Leu Ile Ser
              1               5                  10

CAT GAG AAC AAT GGC TCA TCA GCG GGA AAG CCA TCA TCG TAC CGA ATG        198
His Glu Asn Asn Gly Ser Ser Ala Gly Lys Pro Ser Ser Tyr Arg Met
 15              20                  25

GTG CGA GGA TCC CCA GAA GAC CTC CAG TGT ACC CCG AGG CGC CAG AGT        246
Val Arg Gly Ser Pro Glu Asp Leu Gln Cys Thr Pro Arg Arg Gln Ser
 30              35                  40                      45

GAA GGG ACG GTA TAT GAA GCG GCC ACC GTG GAG GTG GCC GAG TCT GGG        294
Glu Gly Thr Val Tyr Glu Ala Ala Thr Val Glu Val Ala Glu Ser Gly
                 50                  55                  60

TCC ATC ACC CTG CAA GTG CAG CTC GCC ACC CCA GGG GAC CTT TCC TGC        342
Ser Ile Thr Leu Gln Val Gln Leu Ala Thr Pro Gly Asp Leu Ser Cys
                 65                  70                  75

CTC TGG GTC TTT AAG CAC AGC TCC CTG GGC TGC CAG CCG CAC TTT GAT        390
Leu Trp Val Phe Lys His Ser Ser Leu Gly Cys Gln Pro His Phe Asp
             80                  85                  90

TTA CAA AAC AGA GGA ATC GTT TCC ATG GCC ATC TTG AAC GTG ACA GAG        438
Leu Gln Asn Arg Gly Ile Val Ser Met Ala Ile Leu Asn Val Thr Glu
     95                 100                 105

ACC CAG GCA GGA GAA TAC CTA CTC CAT ATT CAG AGC GAA CGC GCC AAC        486
Thr Gln Ala Gly Glu Tyr Leu Leu His Ile Gln Ser Glu Arg Ala Asn
110                 115                 120                 125

TAC ACA GTA CTG TTC ACA GTG AAT GTA AGA GAT ACA CAG CTG TAT GTG        534
Tyr Thr Val Leu Phe Thr Val Asn Val Arg Asp Thr Gln Leu Tyr Val
                130                 135                 140

CTA AGG AGA CCT TAC TTT AGG AAG ATG GAA AAC CAG GAT GCA CTG CTC        582
Leu Arg Arg Pro Tyr Phe Arg Lys Met Glu Asn Gln Asp Ala Leu Leu
                145                 150                 155

TGC ATC TCC GAG GGT GTT CCG GAG CCC ACT GTG GAG TGG GTG CTC TGC        630
Cys Ile Ser Glu Gly Val Pro Glu Pro Thr Val Glu Trp Val Leu Cys
                160                 165                 170

AGC TCC CAC AGG GAA AGC TGT AAA GAA GAA GGC CCT GCT GTT GTC AGA        678
Ser Ser His Arg Glu Ser Cys Lys Glu Glu Gly Pro Ala Val Val Arg
            175                 180                 185
```

```
AAG GAG GAA AAG GTA CTT CAT GAG TTG TTC GGA ACA GAC ATC AGA TGC      726
Lys Glu Glu Lys Val Leu His Glu Leu Phe Gly Thr Asp Ile Arg Cys
190                 195                 200                 205

TGT GCT AGA AAT GCA CTG GGC CGC GAA TGC ACC AAG CTG TTC ACC ATA      774
Cys Ala Arg Asn Ala Leu Gly Arg Glu Cys Thr Lys Leu Phe Thr Ile
            210                 215                 220

GAT CTA AAC CAG GCT CCT CAG AGC ACA CTG CCC CAG TTA TTC CTG AAA      822
Asp Leu Asn Gln Ala Pro Gln Ser Thr Leu Pro Gln Leu Phe Leu Lys
                225                 230                 235

GTG GGG GAA CCC TTG TGG ATC AGG TGT AAG GCC ATC CAT GTG AAC CAT      870
Val Gly Glu Pro Leu Trp Ile Arg Cys Lys Ala Ile His Val Asn His
            240                 245                 250

GGA TTC GGG CTC ACC TGG GAG CTG GAA GAC AAA GCC CTG GAG GAG GGC      918
Gly Phe Gly Leu Thr Trp Glu Leu Glu Asp Lys Ala Leu Glu Glu Gly
255                 260                 265

AGC TAC TTT GAG ATG AGT ACC TAC TCC ACA AAC AGG ACC ATG ATT CGG      966
Ser Tyr Phe Glu Met Ser Thr Tyr Ser Thr Asn Arg Thr Met Ile Arg
270                 275                 280                 285

ATT CTC TTG GCC TTT GTG TCT TCC GTG GGA AGG AAC GAC ACC GGA TAT     1014
Ile Leu Leu Ala Phe Val Ser Ser Val Gly Arg Asn Asp Thr Gly Tyr
                290                 295                 300

TAC ACC TGC TCT TCC TCA AAG CAC CCC AGC CAG TCA GCG TTG GTG ACC     1062
Tyr Thr Cys Ser Ser Ser Lys His Pro Ser Gln Ser Ala Leu Val Thr
            305                 310                 315

ATC CTA GAA AAA GGG TTT ATA AAC GCT ACC AGC TCG CAA GAA GAG TAT     1110
Ile Leu Glu Lys Gly Phe Ile Asn Ala Thr Ser Ser Gln Glu Glu Tyr
                320                 325                 330

GAA ATT GAC CCG TAC GAA AAG TTC TGC TTC TCA GTC AGG TTT AAA GCG     1158
Glu Ile Asp Pro Tyr Glu Lys Phe Cys Phe Ser Val Arg Phe Lys Ala
335                 340                 345

TAC CCA CGA ATC CGA TGC ACG TGG ATC TTC TCT CAA GCC TCA TTT CCT     1206
Tyr Pro Arg Ile Arg Cys Thr Trp Ile Phe Ser Gln Ala Ser Phe Pro
350                 355                 360                 365

TGT GAA CAG AGA GGC CTG GAG GAT GGG TAC AGC ATA TCT AAA TTT TGC     1254
Cys Glu Gln Arg Gly Leu Glu Asp Gly Tyr Ser Ile Ser Lys Phe Cys
                370                 375                 380

GAT CAT AAG AAC AAG CCA GGA GAG TAC ATA TTC TAT GCA GAA AAT GAT     1302
Asp His Lys Asn Lys Pro Gly Glu Tyr Ile Phe Tyr Ala Glu Asn Asp
            385                 390                 395

GAC GCC CAG TTC ACC AAA ATG TTC ACG CTG AAT ATA AGA AAG AAA CCT     1350
Asp Ala Gln Phe Thr Lys Met Phe Thr Leu Asn Ile Arg Lys Lys Pro
                400                 405                 410

CAA GTG CTA GCA AAT GCC TCA GCC AGC CAG GCG TCC TGT TCC TCT GAT     1398
Gln Val Leu Ala Asn Ala Ser Ala Ser Gln Ala Ser Cys Ser Ser Asp
                415                 420                 425

GGC TAC CCG CTA CCC TCT TGG ACC TGG AAG AAG TGT TCG GAC AAA TCT     1446
Gly Tyr Pro Leu Pro Ser Trp Thr Trp Lys Lys Cys Ser Asp Lys Ser
430                 435                 440                 445

CCC AAT TGC ACG GAG GAA ATC CCA GAA GGA GTT TGG AAT AAA AAG GCT     1494
Pro Asn Cys Thr Glu Glu Ile Pro Glu Gly Val Trp Asn Lys Lys Ala
            450                 455                 460

AAC AGA AAA GTG TTT GGC CAG TGG GTG TCG AGC AGT ACT CTA AAT ATG     1542
Asn Arg Lys Val Phe Gly Gln Trp Val Ser Ser Ser Thr Leu Asn Met
                465                 470                 475

AGT GAG GCC GGG AAA GGG CTT CTG GTC AAA TGC TGT GCG TAC AAT TCT     1590
Ser Glu Ala Gly Lys Gly Leu Leu Val Lys Cys Cys Ala Tyr Asn Ser
            480                 485                 490

ATG GGC ACG TCT TGC GAA ACC ATC TTT TTA AAC TCA CCA GGC CCC TTC     1638
Met Gly Thr Ser Cys Glu Thr Ile Phe Leu Asn Ser Pro Gly Pro Phe
```

-continued

|  |  |
|---|---|
| CCT TTC ATC CAA GAC AAC ATC TCC TTC TAT GCG ACC ATT GGG CTC TGT<br>Pro Phe Ile Gln Asp Asn Ile Ser Phe Tyr Ala Thr Ile Gly Leu Cys<br>510                         515                     520                    525 | 1686 |
| CTC CCC TTC ATT GTT GTT CTC ATT GTG TTG ATC TGC CAC AAA TAC AAA<br>Leu Pro Phe Ile Val Val Leu Ile Val Leu Ile Cys His Lys Tyr Lys<br>                    530                     535                     540 | 1734 |
| AAG CAA TTT AGG TAC GAG AGT CAG CTG CAG ATG ATC CAG GTG ACT GGC<br>Lys Gln Phe Arg Tyr Glu Ser Gln Leu Gln Met Ile Gln Val Thr Gly<br>               545                     550                     555 | 1782 |
| CCC CTG GAT AAC GAG TAC TTC TAC GTT GAC TTC AGG GAC TAT GAA TAT<br>Pro Leu Asp Asn Glu Tyr Phe Tyr Val Asp Phe Arg Asp Tyr Glu Tyr<br>           560                     565                     570 | 1830 |
| GAC CTT AAG TGG GAG TTC CCG AGA GAG AAC TTA GAG TTT GGG AAG GTC<br>Asp Leu Lys Trp Glu Phe Pro Arg Glu Asn Leu Glu Phe Gly Lys Val<br>575                         580                     585 | 1878 |
| CTG GGG TCT GGC GCT TTC GGG AGG GTG ATG AAC GCC ACG GCC TAT GGC<br>Leu Gly Ser Gly Ala Phe Gly Arg Val Met Asn Ala Thr Ala Tyr Gly<br>590                         595                     600                     605 | 1926 |
| ATT AGT AAA ACG GGA GTC TCA ATT CAG GTG GCG GTG AAG ATG CTA AAA<br>Ile Ser Lys Thr Gly Val Ser Ile Gln Val Ala Val Lys Met Leu Lys<br>                    610                     615                     620 | 1974 |
| GAG AAA GCT GAC AGC TGT GAA AAA GAA GCT CTC ATG TCG GAG CTC AAA<br>Glu Lys Ala Asp Ser Cys Glu Lys Glu Ala Leu Met Ser Glu Leu Lys<br>           625                     630                     635 | 2022 |
| ATG ATG ACC CAC CTG GGA CAC CAT GAC AAC ATC GTG AAT CTG CTG GGG<br>Met Met Thr His Leu Gly His His Asp Asn Ile Val Asn Leu Leu Gly<br>        640                     645                     650 | 2070 |
| GCA TGC ACA CTG TCA GGG CCA GTG TAC TTG ATT TTT GAA TAT TGT TGC<br>Ala Cys Thr Leu Ser Gly Pro Val Tyr Leu Ile Phe Glu Tyr Cys Cys<br>655                         660                     665 | 2118 |
| TAT GGT GAC CTC CTC AAC TAC CTA AGA AGT AAA AGA GAG AAG TTT CAC<br>Tyr Gly Asp Leu Leu Asn Tyr Leu Arg Ser Lys Arg Glu Lys Phe His<br>670                       675                     680                     685 | 2166 |
| AGG ACA TGG ACA GAG ATT TTT AAG GAA CAT AAT TTC AGT TCT TAC CCT<br>Arg Thr Trp Thr Glu Ile Phe Lys Glu His Asn Phe Ser Ser Tyr Pro<br>                    690                     695                     700 | 2214 |
| ACT TTC CAG GCA CAT TCA AAT TCC AGC ATG CCT GGT TCA CGA GAA GTT<br>Thr Phe Gln Ala His Ser Asn Ser Ser Met Pro Gly Ser Arg Glu Val<br>           705                     710                     715 | 2262 |
| CAG TTA CAC CCG CCC TTG GAT CAG CTC TCA GGG TTC AAT GGG AAT TCA<br>Gln Leu His Pro Pro Leu Asp Gln Leu Ser Gly Phe Asn Gly Asn Ser<br>        720                     725                     730 | 2310 |
| ATT CAT TCT GAA GAT GAG ATT GAA TAT GAA AAC CAG AAG AGG CTG GCA<br>Ile His Ser Glu Asp Glu Ile Glu Tyr Glu Asn Gln Lys Arg Leu Ala<br>735                         740                     745 | 2358 |
| GAA GAA GAG GAG GAA GAT TTG AAC GTG CTG ACG TTT GAA GAC CTC CTT<br>Glu Glu Glu Glu Glu Asp Leu Asn Val Leu Thr Phe Glu Asp Leu Leu<br>750                         755                     760                     765 | 2406 |
| TGC TTT GCG TAC CAA GTG GCC AAA GGC ATG GAA TTC CTG GAG TTC AAG<br>Cys Phe Ala Tyr Gln Val Ala Lys Gly Met Glu Phe Leu Glu Phe Lys<br>                    770                     775                     780 | 2454 |
| TCG TGT GTC CAC AGA GAC CTG GCA GCC AGG AAT GTG TTG GTC ACC CAC<br>Ser Cys Val His Arg Asp Leu Ala Ala Arg Asn Val Leu Val Thr His<br>           785                     790                     795 | 2502 |
| GGG AAG GTG GTG AAG ATC TGT GAC TTT GGA CTG GCC CGA GAC ATC CTG<br>Gly Lys Val Val Lys Ile Cys Asp Phe Gly Leu Ala Arg Asp Ile Leu<br>        800                     805                     810 | 2550 |
| AGC GAC TCC AGC TAC GTC GTC AGG GGC AAC GCA CGG CTG CCG GTG AAG | 2598 |

-continued

```
Ser Asp Ser Ser Tyr Val Val Arg Gly Asn Ala Arg Leu Pro Val Lys
    815                 820                 825

TGG ATG GCA CCC GAG AGC TTA TTT GAA GGG ATC TAC ACA ATC AAG AGT    2646
Trp Met Ala Pro Glu Ser Leu Phe Glu Gly Ile Tyr Thr Ile Lys Ser
830                 835                 840                 845

GAC GTC TGG TCC TAC GGC ATC CTT CTC TGG GAG ATA TTT TCA CTG GGT    2694
Asp Val Trp Ser Tyr Gly Ile Leu Leu Trp Glu Ile Phe Ser Leu Gly
            850                 855                 860

GTG AAC CCT TAC CCT GGC ATT CCT GTC GAC GCT AAC TTC TAT AAA CTG    2742
Val Asn Pro Tyr Pro Gly Ile Pro Val Asp Ala Asn Phe Tyr Lys Leu
            865                 870                 875

ATT CAG AGT GGA TTT AAA ATG GAG CAG CCA TTC TAT GCC ACA GAA GGG    2790
Ile Gln Ser Gly Phe Lys Met Glu Gln Pro Phe Tyr Ala Thr Glu Gly
                880                 885                 890

ATA TAC TTT GTA ATG CAA TCC TGC TGG GCT TTT GAC TCA AGG AAG CGG    2838
Ile Tyr Phe Val Met Gln Ser Cys Trp Ala Phe Asp Ser Arg Lys Arg
895                 900                 905

CCA TCC TTC CCC AAC CTG ACT TCA TTT TTA GGA TGT CAG CTG GCA GAG    2886
Pro Ser Phe Pro Asn Leu Thr Ser Phe Leu Gly Cys Gln Leu Ala Glu
910                 915                 920                 925

GCA GAA GAA GCA TGT ATC AGA ACA TCC ATC CAT CTA CCA AAA CAG GCG    2934
Ala Glu Glu Ala Cys Ile Arg Thr Ser Ile His Leu Pro Lys Gln Ala
                930                 935                 940

GCC CCT CAG CAG AGA GGC GGG CTC AGA GCC CAG TCG CCA CAG CGC CAG    2982
Ala Pro Gln Gln Arg Gly Gly Leu Arg Ala Gln Ser Pro Gln Arg Gln
            945                 950                 955

GTG AAG ATT CAC AGA GAA AGA AGT TAGCGAGGAG GCCTTGGACC CCGCCACCCT    3036
Val Lys Ile His Arg Glu Arg Ser
            960                 965

AGCAGGCTGT AGACCGCAGA GCCAAGATTA GCCTCGCCTC TGAGGAAGCG CCCTACAGCG    3096

CGTTGCTTCG CTGGACTTTT CTCTAGATGC TGTCTGCCAT TACTCCAAAG TGACTTCTAT    3156

AAAATCAAAC CTCTCCTCGC ACAGGCGGGA GAGCCAATAA TGAGACTTGT TGGTGAGCCC    3216

GCCTACCCTG GGGGCCTTTC CACGAGCTTG AGGGGAAAGC CATGTATCTG AAATATAGTA    3276

TATTCTTGTA AATACGTGAA ACAAACCAAA CCCGTTTTTT GCTAAGGGAA AGCTAAATAT    3336

GATTTTTAAA AATCTATGTT TTAAAATACT ATGTAACTTT TTCATCTATT TAGTGATATA    3396

TTTTATGGAT GGAAATAAAC TTTCTACTGT AAAAAAAAAA AAAAAAAAAA AAAAAAA       3453

(2) INFORMATION FOR SEQ ID NO: 2:

(i) SEQUENCE CHARACTERISTICS:
        (A) LENGTH: 992 amino acids
        (B) TYPE: amino acid
        (D) TOPOLOGY: linear (ii) MOLECULE TYPE: protein (xi) SEQUENCE DESCRIPTION: SEQ ID NO: 2:

Met Arg Ala Leu Ala Gln Arg Ser Asp Arg Arg Leu Leu Leu Leu Val
-27     -25                 -20                 -15

Val Leu Ser Val Met Ile Leu Glu Thr Val Thr Asn Gln Asp Leu Pro
    -10                 -5                  1                   5

Val Ile Lys Cys Val Leu Ile Ser His Glu Asn Asn Gly Ser Ser Ala
                10                  15                  20

Gly Lys Pro Ser Ser Tyr Arg Met Val Arg Gly Ser Pro Glu Asp Leu
            25                  30                  35

Gln Cys Thr Pro Arg Arg Gln Ser Glu Gly Thr Val Tyr Glu Ala Ala
        40                  45                  50
```

-continued

Thr Val Glu Val Ala Glu Ser Gly Ser Ile Thr Leu Gln Val Gln Leu
 55                  60                  65

Ala Thr Pro Gly Asp Leu Ser Cys Leu Trp Val Phe Lys His Ser Ser
 70                  75                  80                  85

Leu Gly Cys Gln Pro His Phe Asp Leu Gln Asn Arg Gly Ile Val Ser
                 90                  95                 100

Met Ala Ile Leu Asn Val Thr Glu Thr Gln Ala Gly Glu Tyr Leu Leu
            105                 110                 115

His Ile Gln Ser Glu Arg Ala Asn Tyr Thr Val Leu Phe Thr Val Asn
        120                 125                 130

Val Arg Asp Thr Gln Leu Tyr Val Leu Arg Arg Pro Tyr Phe Arg Lys
135                 140                 145

Met Glu Asn Gln Asp Ala Leu Leu Cys Ile Ser Gly Val Pro Glu
150                 155                 160                 165

Pro Thr Val Glu Trp Val Leu Cys Ser Ser His Arg Glu Ser Cys Lys
                170                 175                 180

Glu Glu Gly Pro Ala Val Val Arg Lys Glu Lys Val Leu His Glu
            185                 190                 195

Leu Phe Gly Thr Asp Ile Arg Cys Cys Ala Arg Asn Ala Leu Gly Arg
        200                 205                 210

Glu Cys Thr Lys Leu Phe Thr Ile Asp Leu Asn Gln Ala Pro Gln Ser
215                 220                 225

Thr Leu Pro Gln Leu Phe Leu Lys Val Gly Glu Pro Leu Trp Ile Arg
230                 235                 240                 245

Cys Lys Ala Ile His Val Asn His Gly Phe Gly Leu Thr Trp Glu Leu
                250                 255                 260

Glu Asp Lys Ala Leu Glu Glu Gly Ser Tyr Phe Glu Met Ser Thr Tyr
            265                 270                 275

Ser Thr Asn Arg Thr Met Ile Arg Ile Leu Leu Ala Phe Val Ser Ser
        280                 285                 290

Val Gly Arg Asn Asp Thr Gly Tyr Tyr Thr Cys Ser Ser Ser Lys His
295                 300                 305

Pro Ser Gln Ser Ala Leu Val Thr Ile Leu Glu Lys Gly Phe Ile Asn
310                 315                 320                 325

Ala Thr Ser Ser Gln Glu Glu Tyr Glu Ile Asp Pro Tyr Glu Lys Phe
                330                 335                 340

Cys Phe Ser Val Arg Phe Lys Ala Tyr Pro Arg Ile Arg Cys Thr Trp
            345                 350                 355

Ile Phe Ser Gln Ala Ser Phe Pro Cys Glu Gln Arg Gly Leu Glu Asp
        360                 365                 370

Gly Tyr Ser Ile Ser Lys Phe Cys Asp His Lys Asn Lys Pro Gly Glu
        375                 380                 385

Tyr Ile Phe Tyr Ala Glu Asn Asp Asp Ala Gln Phe Thr Lys Met Phe
390                 395                 400                 405

Thr Leu Asn Ile Arg Lys Lys Pro Gln Val Leu Ala Asn Ala Ser Ala
                410                 415                 420

Ser Gln Ala Ser Cys Ser Ser Asp Gly Tyr Pro Leu Pro Ser Trp Thr
            425                 430                 435

Trp Lys Lys Cys Ser Asp Lys Ser Pro Asn Cys Thr Glu Glu Ile Pro
        440                 445                 450

Glu Gly Val Trp Asn Lys Lys Ala Asn Arg Lys Val Phe Gly Gln Trp
455                 460                 465

```
-continued

Val Ser Ser Ser Thr Leu Asn Met Ser Glu Ala Gly Lys Gly Leu Leu
470             475                 480                 485

Val Lys Cys Cys Ala Tyr Asn Ser Met Gly Thr Ser Cys Glu Thr Ile
                490                 495                 500

Phe Leu Asn Ser Pro Gly Pro Phe Pro Phe Ile Gln Asp Asn Ile Ser
            505                 510                 515

Phe Tyr Ala Thr Ile Gly Leu Cys Leu Pro Phe Ile Val Val Leu Ile
        520                 525                 530

Val Leu Ile Cys His Lys Tyr Lys Lys Gln Phe Arg Tyr Glu Ser Gln
    535                 540                 545

Leu Gln Met Ile Gln Val Thr Gly Pro Leu Asp Asn Glu Tyr Phe Tyr
550             555                 560                 565

Val Asp Phe Arg Asp Tyr Glu Tyr Asp Leu Lys Trp Glu Phe Pro Arg
            570                 575                 580

Glu Asn Leu Glu Phe Gly Lys Val Leu Gly Ser Gly Ala Phe Gly Arg
        585                 590                 595

Val Met Asn Ala Thr Ala Tyr Gly Ile Ser Lys Thr Gly Val Ser Ile
    600                 605                 610

Gln Val Ala Val Lys Met Leu Lys Glu Lys Ala Asp Ser Cys Glu Lys
615             620                 625

Glu Ala Leu Met Ser Glu Leu Lys Met Met Thr His Leu Gly His His
630             635                 640                 645

Asp Asn Ile Val Asn Leu Leu Gly Ala Cys Thr Leu Ser Gly Pro Val
            650                 655                 660

Tyr Leu Ile Phe Glu Tyr Cys Cys Tyr Gly Asp Leu Leu Asn Tyr Leu
        665                 670                 675

Arg Ser Lys Arg Glu Lys Phe His Arg Thr Trp Thr Glu Ile Phe Lys
    680                 685                 690

Glu His Asn Phe Ser Ser Tyr Pro Thr Phe Gln Ala His Ser Asn Ser
695             700                 705

Ser Met Pro Gly Ser Arg Glu Val Gln Leu His Pro Pro Leu Asp Gln
710             715                 720                 725

Leu Ser Gly Phe Asn Gly Asn Ser Ile His Ser Glu Asp Glu Ile Glu
            730                 735                 740

Tyr Glu Asn Gln Lys Arg Leu Ala Glu Glu Glu Glu Asp Leu Asn
        745                 750                 755

Val Leu Thr Phe Glu Asp Leu Leu Cys Phe Ala Tyr Gln Val Ala Lys
    760                 765                 770

Gly Met Glu Phe Leu Glu Phe Lys Ser Cys Val His Arg Asp Leu Ala
775             780                 785

Ala Arg Asn Val Leu Val Thr His Gly Lys Val Val Lys Ile Cys Asp
790             795                 800                 805

Phe Gly Leu Ala Arg Asp Ile Leu Ser Asp Ser Ser Tyr Val Val Arg
            810                 815                 820

Gly Asn Ala Arg Leu Pro Val Lys Trp Met Ala Pro Glu Ser Leu Phe
        825                 830                 835

Glu Gly Ile Tyr Thr Ile Lys Ser Asp Val Trp Ser Tyr Gly Ile Leu
    840                 845                 850

Leu Trp Glu Ile Phe Ser Leu Gly Val Asn Pro Tyr Pro Gly Ile Pro
855             860                 865

Val Asp Ala Asn Phe Tyr Lys Leu Ile Gln Ser Gly Phe Lys Met Glu
870             875                 880                 885

Gln Pro Phe Tyr Ala Thr Glu Gly Ile Tyr Phe Val Met Gln Ser Cys
```

```
                    890              895                 900
Trp Ala Phe Asp Ser Arg Lys Arg Pro Ser Phe Pro Asn Leu Thr Ser
            905                 910                 915

Phe Leu Gly Cys Gln Leu Ala Glu Ala Glu Glu Ala Cys Ile Arg Thr
            920                 925                 930

Ser Ile His Leu Pro Lys Gln Ala Ala Pro Gln Gln Arg Gly Gly Leu
            935                 940                 945

Arg Ala Gln Ser Pro Gln Arg Gln Val Lys Ile His Arg Glu Arg Ser
950                 955                 960                 965

(2) INFORMATION FOR SEQ ID NO: 3:

(i) SEQUENCE CHARACTERISTICS:
        (A) LENGTH: 3501 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 58..3039

(ix) FEATURE:
        (A) NAME/KEY: mat_peptide
        (B) LOCATION: 139..3036

(ix) FEATURE:
        (A) NAME/KEY: sig_peptide
        (B) LOCATION: 58..138

(xi) SEQUENCE DESCRIPTION: SEQ ID NO: 3:

CGAGGCGGCA TCCGAGGGCT GGGCCGGCGC CCTGGGGGAC CCCGGGCTCC GGAGGCC              57

ATG CCG GCG TTG GCG CGC GAC GCG GGC ACC GTG CCG CTG CTC GTT GTT            105
Met Pro Ala Leu Ala Arg Asp Ala Gly Thr Val Pro Leu Leu Val Val
-27         -25                 -20                 -15

TTT TCT GCA ATG ATA TTT GGG ACT ATT ACA AAT CAA GAT CTG CCT GTG            153
Phe Ser Ala Met Ile Phe Gly Thr Ile Thr Asn Gln Asp Leu Pro Val
        -10                 -5                   1                5

ATC AAG TGT GTT TTA ATC AAT CAT AAG AAC AAT GAT TCA TCA GTG GGG            201
Ile Lys Cys Val Leu Ile Asn His Lys Asn Asn Asp Ser Ser Val Gly
                    10                  15                  20

AAG TCA TCA TCA TAT CCC ATG GTA TCA GAA TCC CCG GAA GAC CTC GGG            249
Lys Ser Ser Ser Tyr Pro Met Val Ser Glu Ser Pro Glu Asp Leu Gly
                25                  30                  35

TGT GCG TTG AGA CCC CAG AGC TCA GGG ACA GTG TAC GAA GCT GCC GCT            297
Cys Ala Leu Arg Pro Gln Ser Ser Gly Thr Val Tyr Glu Ala Ala Ala
            40                  45                  50

GTG GAA GTG GAT GTA TCT GCT TCC ATC ACA CTG CAA GTG CTG GTC GAT            345
Val Glu Val Asp Val Ser Ala Ser Ile Thr Leu Gln Val Leu Val Asp
        55                  60                  65

GCC CCA GGG AAC ATT TCC TGT CTC TGG GTC TTT AAG CAC AGC TCC CTG            393
Ala Pro Gly Asn Ile Ser Cys Leu Trp Val Phe Lys His Ser Ser Leu
70                  75                  80                  85

AAT TGC CAG CCA CAT TTT GAT TTA CAA AAC AGA GGA GTT GTT TCC ATG            441
Asn Cys Gln Pro His Phe Asp Leu Gln Asn Arg Gly Val Val Ser Met
                90                  95                 100
```

| | | |
|---|---|---|
| GTC ATT TTG AAA ATG ACA GAA ACC CAA GCT GGA GAA TAC CTA CTT TTT<br>Val Ile Leu Lys Met Thr Glu Thr Gln Ala Gly Glu Tyr Leu Leu Phe<br>            105                   110                 115 | 489 |
| ATT CAG AGT GAA GCT ACC AAT TAC ACA ATA TTG TTT ACA GTG AGT ATA<br>Ile Gln Ser Glu Ala Thr Asn Tyr Thr Ile Leu Phe Thr Val Ser Ile<br>       120                   125                 130 | 537 |
| AGA AAT ACC CTG CTT TAC ACA TTA AGA AGA CCT TAC TTT AGA AAA ATG<br>Arg Asn Thr Leu Leu Tyr Thr Leu Arg Arg Pro Tyr Phe Arg Lys Met<br>135                   140                 145 | 585 |
| GAA AAC CAG GAC GCC CTG GTC TGC ATA TCT GAG AGC GTT CCA GAG CCG<br>Glu Asn Gln Asp Ala Leu Val Cys Ile Ser Glu Ser Val Pro Glu Pro<br>150                 155               160             165 | 633 |
| ATC GTG GAA TGG GTG CTT TGC GAT TCA CAG GGG GAA AGC TGT AAA GAA<br>Ile Val Glu Trp Val Leu Cys Asp Ser Gln Gly Glu Ser Cys Lys Glu<br>               170               175             180 | 681 |
| GAA AGT CCA GCT GTT GTT AAA AAG GAG GAA AAA GTG CTT CAT GAA TTA<br>Glu Ser Pro Ala Val Val Lys Lys Glu Glu Lys Val Leu His Glu Leu<br>             185               190               195 | 729 |
| TTT GGG ACG GAC ATA AGG TGC TGT GCC AGA AAT GAA CTG GGC AGG GAA<br>Phe Gly Thr Asp Ile Arg Cys Cys Ala Arg Asn Glu Leu Gly Arg Glu<br>       200                   205                 210 | 777 |
| TGC ACC AGG CTG TTC ACA ATA GAT CTA AAT CAA ACT CCT CAG ACC ACA<br>Cys Thr Arg Leu Phe Thr Ile Asp Leu Asn Gln Thr Pro Gln Thr Thr<br>             215               220               225 | 825 |
| TTG CCA CAA TTA TTT CTT AAA GTA GGG GAA CCC TTA TGG ATA AGG TGC<br>Leu Pro Gln Leu Phe Leu Lys Val Gly Glu Pro Leu Trp Ile Arg Cys<br>230                   235               240             245 | 873 |
| AAA GCT GTT CAT GTG AAC CAT GGA TTC GGG CTC ACC TGG GAA TTA GAA<br>Lys Ala Val His Val Asn His Gly Phe Gly Leu Thr Trp Glu Leu Glu<br>               250               255             260 | 921 |
| AAC AAA GCA CTC GAG GAG GGC AAC TAC TTT GAG ATG AGT ACC TAT TCA<br>Asn Lys Ala Leu Glu Glu Gly Asn Tyr Phe Glu Met Ser Thr Tyr Ser<br>             265               270               275 | 969 |
| ACA AAC AGA ACT ATG ATA CGG ATT CTG TTT GCT TTT GTA TCA TCA GTG<br>Thr Asn Arg Thr Met Ile Arg Ile Leu Phe Ala Phe Val Ser Ser Val<br>       280                   285                 290 | 1017 |
| GCA AGA AAC GAC ACC GGA TAC TAC ACT TGT TCC TCT TCA AAG CAT CCC<br>Ala Arg Asn Asp Thr Gly Tyr Tyr Thr Cys Ser Ser Ser Lys His Pro<br>295                   300               305 | 1065 |
| AGT CAA TCA GCT TTG GTT ACC ATC GTA GGA AAG GGA TTT ATA AAT GCT<br>Ser Gln Ser Ala Leu Val Thr Ile Val Gly Lys Gly Phe Ile Asn Ala<br>310                   315               320             325 | 1113 |
| ACC AAT TCA AGT GAA GAT TAT GAA ATT GAC CAA TAT GAA GAG TTT TGT<br>Thr Asn Ser Ser Glu Asp Tyr Glu Ile Asp Gln Tyr Glu Glu Phe Cys<br>               330               335             340 | 1161 |
| TTT TCT GTC AGG TTT AAA GCC TAC CCA CAA ATC AGA TGT ACG TGG ACC<br>Phe Ser Val Arg Phe Lys Ala Tyr Pro Gln Ile Arg Cys Thr Trp Thr<br>             345               350               355 | 1209 |
| TTC TCT CGA AAA TCA TTT CCT TGT GAG CAA AAG GGT CTT GAT AAC GGA<br>Phe Ser Arg Lys Ser Phe Pro Cys Glu Gln Lys Gly Leu Asp Asn Gly<br>       360                   365                 370 | 1257 |
| TAC AGC ATA TCC AAG TTT TGC AAT CAT AAG CAC CAG CCA GGA GAA TAT<br>Tyr Ser Ile Ser Lys Phe Cys Asn His Lys His Gln Pro Gly Glu Tyr<br>375                   380               385 | 1305 |
| ATA TTC CAT GCA GAA AAT GAT GAT GCC CAA TTT ACC AAA ATG TTC ACG<br>Ile Phe His Ala Glu Asn Asp Asp Ala Gln Phe Thr Lys Met Phe Thr<br>390                   395               400             405 | 1353 |
| CTG AAT ATA AGA AGG AAA CCT CAA GTG CTC GCA GAA GCA TCG GCA AGT<br>Leu Asn Ile Arg Arg Lys Pro Gln Val Leu Ala Glu Ala Ser Ala Ser<br>             410               415               420 | 1401 |

-continued

| | |
|---|---|
| CAG GCG TCC TGT TTC TCG GAT GGA TAC CCA TTA CCA TCT TGG ACC TGG<br>Gln Ala Ser Cys Phe Ser Asp Gly Tyr Pro Leu Pro Ser Trp Thr Trp<br>            425                      430                      435 | 1449 |
| AAG AAG TGT TCA GAC AAG TCT CCC AAC TGC ACA GAA GAG ATC ACA GAA<br>Lys Lys Cys Ser Asp Lys Ser Pro Asn Cys Thr Glu Glu Ile Thr Glu<br>            440                      445                      450 | 1497 |
| GGA GTC TGG AAT AGA AAG GCT AAC AGA AAA GTG TTT GGA CAG TGG GTG<br>Gly Val Trp Asn Arg Lys Ala Asn Arg Lys Val Phe Gly Gln Trp Val<br>455                      460                      465 | 1545 |
| TCG AGC AGT ACT CTA AAC ATG AGT GAA GCC ATA AAA GGG TTC CTG GTC<br>Ser Ser Ser Thr Leu Asn Met Ser Glu Ala Ile Lys Gly Phe Leu Val<br>470                      475                      480                      485 | 1593 |
| AAG TGC TGT GCA TAC AAT TCC CTT GGC ACA TCT TGT GAG ACG ATC CTT<br>Lys Cys Cys Ala Tyr Asn Ser Leu Gly Thr Ser Cys Glu Thr Ile Leu<br>                      490                      495                      500 | 1641 |
| TTA AAC TCT CCA GGC CCC TTC CCT TTC ATC CAA GAC AAC ATC TCA TTC<br>Leu Asn Ser Pro Gly Pro Phe Pro Phe Ile Gln Asp Asn Ile Ser Phe<br>            505                      510                      515 | 1689 |
| TAT GCA ACA ATT GGT GTT TGT CTC CTC TTC ATT GTC GTT TTA ACC CTG<br>Tyr Ala Thr Ile Gly Val Cys Leu Leu Phe Ile Val Val Leu Thr Leu<br>520                      525                      530 | 1737 |
| CTA ATT TGT CAC AAG TAC AAA AAG CAA TTT AGG TAT GAA AGC CAG CTA<br>Leu Ile Cys His Lys Tyr Lys Lys Gln Phe Arg Tyr Glu Ser Gln Leu<br>            535                      540                      545 | 1785 |
| CAG ATG GTA CAG GTG ACC GGC TCC TCA GAT AAT GAG TAC TTC TAC GTT<br>Gln Met Val Gln Val Thr Gly Ser Ser Asp Asn Glu Tyr Phe Tyr Val<br>550                      555                      560                      565 | 1833 |
| GAT TTC AGA GAA TAT GAA TAT GAT CTC AAA TGG GAG TTT CCA AGA GAA<br>Asp Phe Arg Glu Tyr Glu Tyr Asp Leu Lys Trp Glu Phe Pro Arg Glu<br>                      570                      575                      580 | 1881 |
| AAT TTA GAG TTT GGG AAG GTA CTA GGA TCA GGT GCT TTT GGA AAA GTG<br>Asn Leu Glu Phe Gly Lys Val Leu Gly Ser Gly Ala Phe Gly Lys Val<br>                      585                      590                      595 | 1929 |
| ATG AAC GCA ACA GCT TAT GGA ATT AGC AAA ACA GGA GTC TCA ATC CAG<br>Met Asn Ala Thr Ala Tyr Gly Ile Ser Lys Thr Gly Val Ser Ile Gln<br>            600                      605                      610 | 1977 |
| GTT GCC GTC AAA ATG CTG AAA GAA AAA GCA GAC AGC TCT GAA AGA GAG<br>Val Ala Val Lys Met Leu Lys Glu Lys Ala Asp Ser Ser Glu Arg Glu<br>615                      620                      625 | 2025 |
| GCA CTC ATG TCA GAA CTC AAG ATG ATG ACC CAG CTG GGA AGC CAC GAG<br>Ala Leu Met Ser Glu Leu Lys Met Met Thr Gln Leu Gly Ser His Glu<br>630                      635                      640                      645 | 2073 |
| AAT ATT GTG AAC CTG CTG GGG GCG TGC ACA CTG TCA GGA CCA ATT TAC<br>Asn Ile Val Asn Leu Leu Gly Ala Cys Thr Leu Ser Gly Pro Ile Tyr<br>                      650                      655                      660 | 2121 |
| TTG ATT TTT GAA TAC TGT TGC TAT GGT GAT CTT CTC AAC TAT CTA AGA<br>Leu Ile Phe Glu Tyr Cys Cys Tyr Gly Asp Leu Leu Asn Tyr Leu Arg<br>            665                      670                      675 | 2169 |
| AGT AAA AGA GAA AAA TTT CAC AGG ACT TGG ACA GAG ATT TTC AAG GAA<br>Ser Lys Arg Glu Lys Phe His Arg Thr Trp Thr Glu Ile Phe Lys Glu<br>                      680                      685                      690 | 2217 |
| CAC AAT TTC AGT TTT TAC CCC ACT TTC CAA TCA CAT CCA AAT TCC AGC<br>His Asn Phe Ser Phe Tyr Pro Thr Phe Gln Ser His Pro Asn Ser Ser<br>695                      700                      705 | 2265 |
| ATG CCT GGT TCA AGA GAA GTT CAG ATA CAC CCG GAC TCG GAT CAA ATC<br>Met Pro Gly Ser Arg Glu Val Gln Ile His Pro Asp Ser Asp Gln Ile<br>710                      715                      720                      725 | 2313 |
| TCA GGG CTT CAT GGG AAT TCA TTT CAC TCT GAA GAT GAA ATT GAA TAT<br>Ser Gly Leu His Gly Asn Ser Phe His Ser Glu Asp Glu Ile Glu Tyr | 2361 |

```
                    730                  735                  740
GAA AAC CAA AAA AGG CTG GAA GAA GAG GAG GAC TTG AAT GTG CTT ACA          2409
Glu Asn Gln Lys Arg Leu Glu Glu Glu Glu Asp Leu Asn Val Leu Thr
                745                  750                  755

TTT GAA GAT CTT CTT TGC TTT GCA TAT CAA GTT GCC AAA GGA ATG GAA          2457
Phe Glu Asp Leu Leu Cys Phe Ala Tyr Gln Val Ala Lys Gly Met Glu
            760                  765                  770

TTT CTG GAA TTT AAG TCG TGT GTT CAC AGA GAC CTG GCC GCC AGG AAC          2505
Phe Leu Glu Phe Lys Ser Cys Val His Arg Asp Leu Ala Ala Arg Asn
775                  780                  785

GTG CTT GTC ACC CAC GGG AAA GTG GTG AAG ATA TGT GAC TTT GGA TTG          2553
Val Leu Val Thr His Gly Lys Val Val Lys Ile Cys Asp Phe Gly Leu
        790                  795                  800                  805

GCT CGA GAT ATC ATG AGT GAT TCC AAC TAT GTT GTC AGG GGC AAT GCC          2601
Ala Arg Asp Ile Met Ser Asp Ser Asn Tyr Val Val Arg Gly Asn Ala
                810                  815                  820

CGT CTG CCT GTA AAA TGG ATG GCC CCC GAA AGC CTG TTT GAA GGC ATC          2649
Arg Leu Pro Val Lys Trp Met Ala Pro Glu Ser Leu Phe Glu Gly Ile
            825                  830                  835

TAC ACC ATT AAG AGT GAT GTC TGG TCA TAT GGA ATA TTA CTG TGG GAA          2697
Tyr Thr Ile Lys Ser Asp Val Trp Ser Tyr Gly Ile Leu Leu Trp Glu
        840                  845                  850

ATC TTC TCA CTT GGT GTG AAT CCT TAC CCT GGC ATT CCG GTT GAT GCT          2745
Ile Phe Ser Leu Gly Val Asn Pro Tyr Pro Gly Ile Pro Val Asp Ala
    855                  860                  865

AAC TTC TAC AAA CTG ATT CAA AAT GGA TTT AAA ATG GAT CAG CCA TTT          2793
Asn Phe Tyr Lys Leu Ile Gln Asn Gly Phe Lys Met Asp Gln Pro Phe
870                  875                  880                  885

TAT GCT ACA GAA GAA ATA TAC ATT ATA ATG CAA TCC TGC TGG GCT TTT          2841
Tyr Ala Thr Glu Glu Ile Tyr Ile Ile Met Gln Ser Cys Trp Ala Phe
        890                  895                  900

GAC TCA AGG AAA CGG CCA TCC TTC CCT AAT TTG ACT TCG TTT TTA GGA          2889
Asp Ser Arg Lys Arg Pro Ser Phe Pro Asn Leu Thr Ser Phe Leu Gly
            905                  910                  915

TGT CAG CTG GCA GAT GCA GAA GAA GCG ATG TAT CAG AAT GTG GAT GGC          2937
Cys Gln Leu Ala Asp Ala Glu Glu Ala Met Tyr Gln Asn Val Asp Gly
        920                  925                  930

CGT GTT TCG GAA TGT CCT CAC ACC TAC CAA AAC AGG CGA CCT TTC AGC          2985
Arg Val Ser Glu Cys Pro His Thr Tyr Gln Asn Arg Arg Pro Phe Ser
    935                  940                  945

AGA GAG ATG GAT TTG GGG CTA CTC TCT CCG CAG GCT CAG GTC GAA GAT          3033
Arg Glu Met Asp Leu Gly Leu Leu Ser Pro Gln Ala Gln Val Glu Asp
950                  955                  960                  965

TCG TAGAGGAACA ATTTAGTTTT AAGGACTTCA TCCCTCCACC TATCCCTAAC               3086
Ser

AGGCTGTAGA TTACCAAAAC AAGATTAATT TCATCACTAA AGAAAATCT ATTATCAACT         3146

GCTGCTTCAC CAGACTTTTC TCTAGAAGCC GTCTGCGTTT ACTCTTGTTT TCAAAGGGAC        3206

TTTTGTAAAA TCAAATCATC CTGTCACAAG GCAGGAGGAG CTGATAATGA ACTTTATTGG        3266

AGCATTGATC TGCATCCAAG GCCTTCTCAG GCCGGCTTGA GTGAATTGTG TACCTGAAGT        3326

ACAGTATATT CTTGTAAATA CATAAAACAA AAGCATTTTG CTAAGGAGAA GCTAATATGA        3386

TTTTTTAAGT CTATGTTTTA AAATAATATG TAAATTTTTC AGCTATTTAG TGATATATTT        3446

TATGGGTGGG AATAAAATTT CTACTACAGA AAAAAAAAAA AAAAAAAAAA AAAAA            3501
```

(2) INFORMATION FOR SEQ ID NO: 4:

(i) SEQUENCE CHARACTERISTICS:

-continued

```
        (A) LENGTH: 993 amino acids
        (B) TYPE: amino acid
        (D) TOPOLOGY: linear (ii) MOLECULE TYPE: protein (xi) SEQUENCE DESCRIPTION: SEQ ID NO: 4:

Met Pro Ala Leu Ala Arg Asp Ala Gly Thr Val Pro Leu Val Val
-27         -25                 -20                 -15

Phe Ser Ala Met Ile Phe Gly Thr Ile Thr Asn Gln Asp Leu Pro Val
-10                      -5                   1                  5

Ile Lys Cys Val Leu Ile Asn His Lys Asn Asn Asp Ser Ser Val Gly
                10                  15                      20

Lys Ser Ser Ser Tyr Pro Met Val Ser Glu Ser Pro Glu Asp Leu Gly
                25                  30                  35

Cys Ala Leu Arg Pro Gln Ser Ser Gly Thr Val Tyr Glu Ala Ala Ala
                40                  45                  50

Val Glu Val Asp Val Ser Ala Ser Ile Thr Leu Gln Val Leu Val Asp
    55                  60                  65

Ala Pro Gly Asn Ile Ser Cys Leu Trp Val Phe Lys His Ser Ser Leu
70                  75                  80                  85

Asn Cys Gln Pro His Phe Asp Leu Gln Asn Arg Gly Val Val Ser Met
                90                  95                      100

Val Ile Leu Lys Met Thr Glu Thr Gln Ala Gly Glu Tyr Leu Leu Phe
                105                 110                 115

Ile Gln Ser Glu Ala Thr Asn Tyr Thr Ile Leu Phe Thr Val Ser Ile
                120                 125                 130

Arg Asn Thr Leu Leu Tyr Thr Leu Arg Arg Pro Tyr Phe Arg Lys Met
135                 140                 145

Glu Asn Gln Asp Ala Leu Val Cys Ile Ser Glu Ser Val Pro Glu Pro
150                 155                 160                 165

Ile Val Glu Trp Val Leu Cys Asp Ser Gln Gly Glu Ser Cys Lys Glu
                170                 175                 180

Glu Ser Pro Ala Val Val Lys Lys Glu Glu Lys Val Leu His Glu Leu
                185                 190                 195

Phe Gly Thr Asp Ile Arg Cys Cys Ala Arg Asn Glu Leu Gly Arg Glu
                200                 205                 210

Cys Thr Arg Leu Phe Thr Ile Asp Leu Asn Gln Thr Pro Gln Thr Thr
215                 220                 225

Leu Pro Gln Leu Phe Leu Lys Val Gly Glu Pro Leu Trp Ile Arg Cys
230                 235                 240                 245

Lys Ala Val His Val Asn His Gly Phe Gly Leu Thr Trp Glu Leu Glu
                250                 255                 260

Asn Lys Ala Leu Glu Glu Gly Asn Tyr Phe Glu Met Ser Thr Tyr Ser
                265                 270                 275

Thr Asn Arg Thr Met Ile Arg Ile Leu Phe Ala Phe Val Ser Ser Val
                280                 285                 290

Ala Arg Asn Asp Thr Gly Tyr Tyr Thr Cys Ser Ser Ser Lys His Pro
295                 300                 305

Ser Gln Ser Ala Leu Val Thr Ile Val Gly Lys Gly Phe Ile Asn Ala
310                 315                 320                 325

Thr Asn Ser Ser Glu Asp Tyr Glu Ile Asp Gln Tyr Glu Glu Phe Cys
                330                 335                 340

Phe Ser Val Arg Phe Lys Ala Tyr Pro Gln Ile Arg Cys Thr Trp Thr
                345                 350                 355
```

```
Phe Ser Arg Lys Ser Phe Pro Cys Glu Gln Lys Gly Leu Asp Asn Gly
            360                 365                 370

Tyr Ser Ile Ser Lys Phe Cys Asn His Lys His Gln Pro Gly Glu Tyr
        375                 380                 385

Ile Phe His Ala Glu Asn Asp Asp Ala Gln Phe Thr Lys Met Phe Thr
390                 395                 400                 405

Leu Asn Ile Arg Arg Lys Pro Gln Val Leu Ala Glu Ala Ser Ala Ser
            410                 415                 420

Gln Ala Ser Cys Phe Ser Asp Gly Tyr Pro Leu Pro Ser Trp Thr Trp
            425                 430                 435

Lys Lys Cys Ser Asp Lys Ser Pro Asn Cys Thr Glu Ile Thr Glu
            440                 445                 450

Gly Val Trp Asn Arg Lys Ala Asn Arg Lys Val Phe Gly Gln Trp Val
        455                 460                 465

Ser Ser Ser Thr Leu Asn Met Ser Glu Ala Ile Lys Gly Phe Leu Val
470                 475                 480                 485

Lys Cys Cys Ala Tyr Asn Ser Leu Gly Thr Ser Cys Glu Thr Ile Leu
            490                 495                 500

Leu Asn Ser Pro Gly Pro Phe Pro Phe Ile Gln Asp Asn Ile Ser Phe
            505                 510                 515

Tyr Ala Thr Ile Gly Val Cys Leu Leu Phe Ile Val Val Leu Thr Leu
        520                 525                 530

Leu Ile Cys His Lys Tyr Lys Lys Gln Phe Arg Tyr Glu Ser Gln Leu
        535                 540                 545

Gln Met Val Gln Val Thr Gly Ser Ser Asp Asn Glu Tyr Phe Tyr Val
550                 555                 560                 565

Asp Phe Arg Glu Tyr Glu Tyr Asp Leu Lys Trp Glu Phe Pro Arg Glu
            570                 575                 580

Asn Leu Glu Phe Gly Lys Val Leu Gly Ser Gly Ala Phe Gly Lys Val
            585                 590                 595

Met Asn Ala Thr Ala Tyr Gly Ile Ser Lys Thr Gly Val Ser Ile Gln
            600                 605                 610

Val Ala Val Lys Met Leu Lys Glu Lys Ala Asp Ser Ser Glu Arg Glu
        615                 620                 625

Ala Leu Met Ser Glu Leu Lys Met Met Thr Gln Leu Gly Ser His Glu
630                 635                 640                 645

Asn Ile Val Asn Leu Leu Gly Ala Cys Thr Leu Ser Gly Pro Ile Tyr
            650                 655                 660

Leu Ile Phe Glu Tyr Cys Cys Tyr Gly Asp Leu Leu Asn Tyr Leu Arg
            665                 670                 675

Ser Lys Arg Glu Lys Phe His Arg Thr Trp Thr Glu Ile Phe Lys Glu
            680                 685                 690

His Asn Phe Ser Phe Tyr Pro Thr Phe Gln Ser His Pro Asn Ser Ser
        695                 700                 705

Met Pro Gly Ser Arg Glu Val Gln Ile His Pro Asp Ser Asp Gln Ile
710                 715                 720                 725

Ser Gly Leu His Gly Asn Ser Phe His Ser Glu Asp Glu Ile Glu Tyr
            730                 735                 740

Glu Asn Gln Lys Arg Leu Glu Glu Glu Glu Asp Leu Asn Val Leu Thr
            745                 750                 755

Phe Glu Asp Leu Leu Cys Phe Ala Tyr Gln Val Ala Lys Gly Met Glu
            760                 765                 770
```

```
Phe Leu Glu Phe Lys Ser Cys Val His Arg Asp Leu Ala Ala Arg Asn
    775                 780                 785
Val Leu Val Thr His Gly Lys Val Val Lys Ile Cys Asp Phe Gly Leu
790                 795                 800                 805
Ala Arg Asp Ile Met Ser Asp Ser Asn Tyr Val Val Arg Gly Asn Ala
                810                 815                 820
Arg Leu Pro Val Lys Trp Met Ala Pro Glu Ser Leu Phe Glu Gly Ile
            825                 830                 835
Tyr Thr Ile Lys Ser Asp Val Trp Ser Tyr Gly Ile Leu Leu Trp Glu
        840                 845                 850
Ile Phe Ser Leu Gly Val Asn Pro Tyr Pro Gly Ile Pro Val Asp Ala
    855                 860                 865
Asn Phe Tyr Lys Leu Ile Gln Asn Gly Phe Lys Met Asp Gln Pro Phe
870                 875                 880                 885
Tyr Ala Thr Glu Glu Ile Tyr Ile Ile Met Gln Ser Cys Trp Ala Phe
                890                 895                 900
Asp Ser Arg Lys Arg Pro Ser Phe Pro Asn Leu Thr Ser Phe Leu Gly
            905                 910                 915
Cys Gln Leu Ala Asp Ala Glu Glu Ala Met Tyr Gln Asn Val Asp Gly
        920                 925                 930
Arg Val Ser Glu Cys Pro His Thr Tyr Gln Asn Arg Arg Pro Phe Ser
    935                 940                 945
Arg Glu Met Asp Leu Gly Leu Leu Ser Pro Gln Ala Gln Val Glu Asp
950                 955                 960                 965
Ser (2) INFORMATION FOR SEQ ID NO: 5:

(i) SEQUENCE CHARACTERISTICS:
        (A) LENGTH: 5406 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE: N-terminal (ix) FEATURE:
        (A) NAME/KEY: CDS
        (B) LOCATION: 208..4311

(ix) FEATURE:
        (A) NAME/KEY: mat_peptide
        (B) LOCATION: 265..4308

(ix) FEATURE:
        (A) NAME/KEY: sig_peptide
        (B) LOCATION: 208..264

(xi) SEQUENCE DESCRIPTION: SEQ ID NO: 5:

CTGTGTCCCG CAGCCGGATA ACCTGGCTGA CCCGATTCCG CGGACACCCG TGCAGCCGCG    60

GCTGGAGCCA GGGCGCCGGT GCCCGCGCTC TCCCCGGTCT TGCGCTGCGG GGGCCGATAC   120

CGCCTCTGTG ACTTCTTTGC GGGCCAGGGA CGGAGAAGGA GTCTGTGCCT GAGAAACTGG   180

GCTCTGTGCC CAGGCGCGAG GTGCAGG ATG GAG AGC AAG GGC CTG CTA GCT       231
                               Met Glu Ser Lys Gly Leu Leu Ala
                               -19                 -15
```

-continued

| | | |
|---|---|---|
| GTC GCT CTG TGG TTC TGC GTG GAG ACC CGA GCC GCT TCT GTG GGT TTG<br>Val Ala Leu Trp Phe Cys Val Glu Thr Arg Ala Ala Ser Val Gly Leu<br>    -10                         -5                           1                  5 | 279 |

```
GTC GCT CTG TGG TTC TGC GTG GAG ACC CGA GCC GCT TCT GTG GGT TTG       279
Val Ala Leu Trp Phe Cys Val Glu Thr Arg Ala Ala Ser Val Gly Leu
        -10                  -5                   1                5

CCT GGC GAT TTT CTC CAT CCC CCC AAG CTC AGC ACA CAG AAA GAC ATA       327
Pro Gly Asp Phe Leu His Pro Pro Lys Leu Ser Thr Gln Lys Asp Ile
             10                  15                  20

CTG ACA ATT TTG GCA AAT ACA ACC CTT CAG ATT ACT TGC AGG GGA CAG       375
Leu Thr Ile Leu Ala Asn Thr Thr Leu Gln Ile Thr Cys Arg Gly Gln
         25                  30                  35

CGG GAC CTG GAC TGG CTT TGG CCC AAT GCT CAG CGT GAT TCT GAG GAA       423
Arg Asp Leu Asp Trp Leu Trp Pro Asn Ala Gln Arg Asp Ser Glu Glu
     40                  45                  50

AGG GTA TTG GTG ACT GAA TGC GGC GGT GGT GAC AGT ATC TTC TGC AAA       471
Arg Val Leu Val Thr Glu Cys Gly Gly Gly Asp Ser Ile Phe Cys Lys
 55                  60                  65

ACA CTC ACC ATT CCC AGG GTG GTT GGA AAT GAT ACT GGA GCC TAC AAG       519
Thr Leu Thr Ile Pro Arg Val Val Gly Asn Asp Thr Gly Ala Tyr Lys
 70              75                  80                  85

TGC TCG TAC CGG GAC GTC GAC ATA GCC TCC ACT GTT TAT GTC TAT GTT       567
Cys Ser Tyr Arg Asp Val Asp Ile Ala Ser Thr Val Tyr Val Tyr Val
             90                  95                 100

CGA GAT TAC AGA TCA CCA TTC ATC GCC TCT GTC AGT GAC CAG CAT GGC       615
Arg Asp Tyr Arg Ser Pro Phe Ile Ala Ser Val Ser Asp Gln His Gly
            105                 110                 115

ATC GTG TAC ATC ACC GAG AAC AAG AAC AAA ACT GTG GTG ATC CCC TGC       663
Ile Val Tyr Ile Thr Glu Asn Lys Asn Lys Thr Val Val Ile Pro Cys
        120                 125                 130

CGA GGG TCG ATT TCA AAC CTC AAT GTG TCT CTT TGC GCT AGG TAT CCA       711
Arg Gly Ser Ile Ser Asn Leu Asn Val Ser Leu Cys Ala Arg Tyr Pro
    135                 140                 145

GAA AAG AGA TTT GTT CCG GAT GGA AAC AGA ATT TCC TGG GAC AGC GAG       759
Glu Lys Arg Phe Val Pro Asp Gly Asn Arg Ile Ser Trp Asp Ser Glu
150                 155                 160                 165

ATA GGC TTT ACT CTC CCC AGT TAC ATG ATC AGC TAT GCC GGC ATG GTC       807
Ile Gly Phe Thr Leu Pro Ser Tyr Met Ile Ser Tyr Ala Gly Met Val
                170                 175                 180

TTC TGT GAG GCA AAG ATC AAT GAT GAA ACC TAT CAG TCT ATC ATG TAC       855
Phe Cys Glu Ala Lys Ile Asn Asp Glu Thr Tyr Gln Ser Ile Met Tyr
            185                 190                 195

ATA GTT GTG GTT GTA GGA TAT AGG ATT TAT GAT GTG ATT CTG AGC CCC       903
Ile Val Val Val Val Gly Tyr Arg Ile Tyr Asp Val Ile Leu Ser Pro
        200                 205                 210

CCG CAT GAA ATT GAG CTA TCT GCC GGA GAA AAA CTT GTC TTA AAT TGT       951
Pro His Glu Ile Glu Leu Ser Ala Gly Glu Lys Leu Val Leu Asn Cys
    215                 220                 225

ACA GCG AGA ACA GAG CTC AAT GTG GGG CTT GAT TTC ACC TGG CAC TCT       999
Thr Ala Arg Thr Glu Leu Asn Val Gly Leu Asp Phe Thr Trp His Ser
230                 235                 240                 245

CCA CCT TCA AAG TCT CAT CAT AAG AAG ATT GTA AAC CGG GAT GTG AAA      1047
Pro Pro Ser Lys Ser His His Lys Lys Ile Val Asn Arg Asp Val Lys
                250                 255                 260

CCC TTT CCT GGG ACT GTG GCG AAG ATG TTT TTG AGC ACC TTG ACA ATA      1095
Pro Phe Pro Gly Thr Val Ala Lys Met Phe Leu Ser Thr Leu Thr Ile
            265                 270                 275

GAA AGT GTG ACC AAG AGT GAC CAA GGG GAA TAC ACC TGT GTA GCG TCC      1143
Glu Ser Val Thr Lys Ser Asp Gln Gly Glu Tyr Thr Cys Val Ala Ser
        280                 285                 290

AGT GGA CGG ATG ATC AAG AGA AAT AGA ACA TTT GTC CGA GTT CAC ACA      1191
Ser Gly Arg Met Ile Lys Arg Asn Arg Thr Phe Val Arg Val His Thr
    295                 300                 305
```

|  |  |
|---|---|
| AAG CCT TTT ATT GCT TTC GGT AGT GGG ATG AAA TCT TTG GTG GAA GCC<br>Lys Pro Phe Ile Ala Phe Gly Ser Gly Met Lys Ser Leu Val Glu Ala<br>310                         315                    320                   325 | 1239 |
| ACA GTG GGC AGT CAA GTC CGA ATC CCT GTG AAG TAT CTC AGT TAC CCA<br>Thr Val Gly Ser Gln Val Arg Ile Pro Val Lys Tyr Leu Ser Tyr Pro<br>                    330                         335                   340 | 1287 |
| GCT CCT GAT ATC AAA TGG TAC AGA AAT GGA AGG CCC ATT GAG TCC AAC<br>Ala Pro Asp Ile Lys Trp Tyr Arg Asn Gly Arg Pro Ile Glu Ser Asn<br>345                              350                    355 | 1335 |
| TAC ACA ATG ATT GTT GGC GAT GAA CTC ACC ATC ATG GAA GTG ACT GAA<br>Tyr Thr Met Ile Val Gly Asp Glu Leu Thr Ile Met Glu Val Thr Glu<br>                  360                     365                   370 | 1383 |
| AGA GAT GCA GGA AAC TAC ACG GTC ATC CTC ACC AAC CCC ATT TCA ATG<br>Arg Asp Ala Gly Asn Tyr Thr Val Ile Leu Thr Asn Pro Ile Ser Met<br>375                         380                        385 | 1431 |
| GAG AAA CAG AGC CAC ATG GTC TCT CTG GTT GTG AAT GTC CCA CCC CAG<br>Glu Lys Gln Ser His Met Val Ser Leu Val Val Asn Val Pro Pro Gln<br>390                         395                    400                   405 | 1479 |
| ATC GGT GAG AAA GCC TTG ATC TCG CCT ATG GAT TCC TAC CAG TAT GGG<br>Ile Gly Glu Lys Ala Leu Ile Ser Pro Met Asp Ser Tyr Gln Tyr Gly<br>                  410                    415                   420 | 1527 |
| ACC ATG CAG ACA TTG ACA TGC ACA GTC TAC GCC AAC CCT CCC CTG CAC<br>Thr Met Gln Thr Leu Thr Cys Thr Val Tyr Ala Asn Pro Pro Leu His<br>425                       430                        435 | 1575 |
| CAC ATC CAG TGG TAC TGG CAG CTA GAA GAA GCC TGC TCC TAC AGA CCC<br>His Ile Gln Trp Tyr Trp Gln Leu Glu Glu Ala Cys Ser Tyr Arg Pro<br>                  440                    445                   450 | 1623 |
| GGC CAA ACA AGC CCG TAT GCT TGT AAA GAA TGG AGA CAC GTG GAG GAT<br>Gly Gln Thr Ser Pro Tyr Ala Cys Lys Glu Trp Arg His Val Glu Asp<br>455                         460                    465 | 1671 |
| TTC CAG GGG GGA AAC AAG ATC GAA GTC ACC AAA AAC CAA TAT GCC CTG<br>Phe Gln Gly Gly Asn Lys Ile Glu Val Thr Lys Asn Gln Tyr Ala Leu<br>470                       475                    480                   485 | 1719 |
| ATT GAA GGA AAA AAC AAA ACT GTA AGT ACG CTG GTC ATC CAA GCT GCC<br>Ile Glu Gly Lys Asn Lys Thr Val Ser Thr Leu Val Ile Gln Ala Ala<br>                  490                    495                   500 | 1767 |
| AAC GTG TCA GCG TTG TAC AAA TGT GAA GCC ATC AAC AAA GCG GGA CGA<br>Asn Val Ser Ala Leu Tyr Lys Cys Glu Ala Ile Asn Lys Ala Gly Arg<br>                    505                     510                   515 | 1815 |
| GGA GAG AGG GTC ATC TCC TTC CAT GTG ATC AGG GGT CCT GAA ATT ACT<br>Gly Glu Arg Val Ile Ser Phe His Val Ile Arg Gly Pro Glu Ile Thr<br>                  520                    525                   530 | 1863 |
| GTG CAA CCT GCT GCC CAG CCA ACT GAG CAG GAG AGT GTG TCC CTG TTG<br>Val Gln Pro Ala Ala Gln Pro Thr Glu Gln Glu Ser Val Ser Leu Leu<br>535                         540                    545 | 1911 |
| TGC ACT GCA GAC AGA AAT ACG TTT GAG AAC CTC ACG TGG TAC AAG CTT<br>Cys Thr Ala Asp Arg Asn Thr Phe Glu Asn Leu Thr Trp Tyr Lys Leu<br>550                         555                    560                   565 | 1959 |
| GGC TCA CAG GCA ACA TCG GTC CAC ATG GGC GAA TCA CTC ACA CCA GTT<br>Gly Ser Gln Ala Thr Ser Val His Met Gly Glu Ser Leu Thr Pro Val<br>                  570                    575                   580 | 2007 |
| TGC AAG AAC TTG GAT GCT CTT TGG AAA CTG AAT GGC ACC ATG TTT TCT<br>Cys Lys Asn Leu Asp Ala Leu Trp Lys Leu Asn Gly Thr Met Phe Ser<br>                    585                     590                   595 | 2055 |
| AAC AGC ACA AAT GAC ATC TTG ATT GTG GCA TTT CAG AAT GCC TCT CTG<br>Asn Ser Thr Asn Asp Ile Leu Ile Val Ala Phe Gln Asn Ala Ser Leu<br>                  600                    605                   610 | 2103 |
| CAG GAC CAA GGC GAC TAT GTT TGC TCT GCT CAA GAT AAG AAG ACC AAG<br>Gln Asp Gln Gly Asp Tyr Val Cys Ser Ala Gln Asp Lys Lys Thr Lys | 2151 |

```
              615                 620                 625
AAA AGA CAT TGC CTG GTC AAA CAG CTC ATC ATC CTA GAG CGC ATG GCA         2199
Lys Arg His Cys Leu Val Lys Gln Leu Ile Ile Leu Glu Arg Met Ala
630             635                 640                 645

CCC ATG ATC ACC GGA AAT CTG GAG AAT CAG ACA ACA ACC ATT GGC GAG         2247
Pro Met Ile Thr Gly Asn Leu Glu Asn Gln Thr Thr Thr Ile Gly Glu
                650                 655                 660

ACC ATT GAA GTG ACT TGC CCA GCA TCT GGA AAT CCT ACC CCA CAC ATT         2295
Thr Ile Glu Val Thr Cys Pro Ala Ser Gly Asn Pro Thr Pro His Ile
            665                 670                 675

ACA TGG TTC AAA GAC AAC GAG ACC CTG GTA GAA GAT TCA GGC ATT GTA         2343
Thr Trp Phe Lys Asp Asn Glu Thr Leu Val Glu Asp Ser Gly Ile Val
        680                 685                 690

CTG AGA GAT GGG AAC CGG AAC CTG ACT ATC CGC AGG GTG AGG AAG GAG         2391
Leu Arg Asp Gly Asn Arg Asn Leu Thr Ile Arg Arg Val Arg Lys Glu
    695                 700                 705

GAT GGA GGC CTC TAC ACC TGC CAG GCC TGC AAT GTC CTT GGC TGT GCA         2439
Asp Gly Gly Leu Tyr Thr Cys Gln Ala Cys Asn Val Leu Gly Cys Ala
710                 715                 720                 725

AGA GCG GAG ACG CTC TTC ATA ATA GAA GGT GCC CAG GAA AAG ACC AAC         2487
Arg Ala Glu Thr Leu Phe Ile Ile Glu Gly Ala Gln Glu Lys Thr Asn
                730                 735                 740

TTG GAA GTC ATT ATC CTC GTC GGC ACT GCA GTG ATT GCC ATG TTC TTC         2535
Leu Glu Val Ile Ile Leu Val Gly Thr Ala Val Ile Ala Met Phe Phe
            745                 750                 755

TGG CTC CTT CTT GTC ATT CTC GTA CGG ACC GTT AAG CGG GCC AAT GAA         2583
Trp Leu Leu Leu Val Ile Leu Val Arg Thr Val Lys Arg Ala Asn Glu
        760                 765                 770

GGG GAA CTG AAG ACA GGC TAC TTG TCT ATT GTC ATG GAT CCA GAT GAA         2631
Gly Glu Leu Lys Thr Gly Tyr Leu Ser Ile Val Met Asp Pro Asp Glu
    775                 780                 785

TTG CCC TTG GAT GAG CGC TGT GAA CGC TTG CCT TAT GAT GCC AGC AAG         2679
Leu Pro Leu Asp Glu Arg Cys Glu Arg Leu Pro Tyr Asp Ala Ser Lys
790                 795                 800                 805

TGG GAA TTC CCC AGG GAC CGG CTG AAA CTA GGA AAA CCT CTT GGC CGC         2727
Trp Glu Phe Pro Arg Asp Arg Leu Lys Leu Gly Lys Pro Leu Gly Arg
                810                 815                 820

GGT GCC TTC GGC CAA GTG ATT GAG GCA GAC GCT TTT GGA ATT GAC AAG         2775
Gly Ala Phe Gly Gln Val Ile Glu Ala Asp Ala Phe Gly Ile Asp Lys
            825                 830                 835

ACA GCG ACT TGC AAA ACA GTA GCC GTC AAG ATG TTG AAA GAA GGA GCA         2823
Thr Ala Thr Cys Lys Thr Val Ala Val Lys Met Leu Lys Glu Gly Ala
        840                 845                 850

ACA CAC AGC GAG CAT CGA GCC CTC ATG TCT GAA CTC AAG ATC CTC ATC         2871
Thr His Ser Glu His Arg Ala Leu Met Ser Glu Leu Lys Ile Leu Ile
    855                 860                 865

CAC ATT GGT CAC CAT CTC AAT GTG GTG AAC CTC CTA GGC GCC TGC ACC         2919
His Ile Gly His His Leu Asn Val Val Asn Leu Leu Gly Ala Cys Thr
870                 875                 880                 885

AAG CCG GGA GGG CCT CTC ATG GTG ATT GTG GAA TTC TCG AAG TTT GGA         2967
Lys Pro Gly Gly Pro Leu Met Val Ile Val Glu Phe Ser Lys Phe Gly
                890                 895                 900

AAC CTA TCA ACT TAC TTA CGG GGC AAG AGA AAT GAA TTT GTT CCC TAT         3015
Asn Leu Ser Thr Tyr Leu Arg Gly Lys Arg Asn Glu Phe Val Pro Tyr
            905                 910                 915

AAG AGC AAA GGG GCA CGC TTC CGC CAG GGC AAG GAC TAC GTT GGG GAG         3063
Lys Ser Lys Gly Ala Arg Phe Arg Gln Gly Lys Asp Tyr Val Gly Glu
        920                 925                 930

CTC TCC GTG GAT CTG AAA AGA CGC TTG GAC AGC ATC ACC AGC AGC CAG         3111
```

```
                Leu Ser Val Asp Leu Lys Arg Arg Leu Asp Ser Ile Thr Ser Ser Gln
                    935                 940                 945

AGC TCT GCC AGC TCA GGC TTT GTT GAG GAG AAA TCG CTC AGT GAT GTA           3159
Ser Ser Ala Ser Ser Gly Phe Val Glu Glu Lys Ser Leu Ser Asp Val
950                 955                 960                 965

GAG GAA GAA GAA GCT TCT GAA GAA CTG TAC AAG GAC TTC CTG ACC TTG           3207
Glu Glu Glu Glu Ala Ser Glu Glu Leu Tyr Lys Asp Phe Leu Thr Leu
                    970                 975                 980

GAG CAT CTC ATC TGT TAC AGC TTC CAA GTG GCT AAG GGC ATG GAG TTC           3255
Glu His Leu Ile Cys Tyr Ser Phe Gln Val Ala Lys Gly Met Glu Phe
                985                 990                 995

TTG GCA TCA AGG AAG TGT ATC CAC AGG GAC CTG GCA GCA CGA AAC ATT           3303
Leu Ala Ser Arg Lys Cys Ile His Arg Asp Leu Ala Ala Arg Asn Ile
            1000                1005                1010

CTC CTA TCG GAG AAG AAT GTG GTT AAG ATC TGT GAC TTC GGC TTG GCC           3351
Leu Leu Ser Glu Lys Asn Val Val Lys Ile Cys Asp Phe Gly Leu Ala
        1015                1020                1025

CGG GAC ATT TAT AAA GAC CCG GAT TAT GTC AGA AAA GGA GAT GCC CGA           3399
Arg Asp Ile Tyr Lys Asp Pro Asp Tyr Val Arg Lys Gly Asp Ala Arg
1030                1035                1040                1045

CTC CCT TTG AAG TGG ATG GCC CCG GAA ACC ATT TTT GAC AGA GTA TAC           3447
Leu Pro Leu Lys Trp Met Ala Pro Glu Thr Ile Phe Asp Arg Val Tyr
                1050                1055                1060

ACA ATT CAG AGC GAT GTG TGG TCT TTC GGT GTG TTG CTC TGG GAA ATA           3495
Thr Ile Gln Ser Asp Val Trp Ser Phe Gly Val Leu Leu Trp Glu Ile
                1065                1070                1075

TTT TCC TTA GGT GCC TCC CCA TAC CCT GGG GTC AAG ATT GAT GAA GAA           3543
Phe Ser Leu Gly Ala Ser Pro Tyr Pro Gly Val Lys Ile Asp Glu Glu
            1080                1085                1090

TTT TGT AGG AGA TTG AAA GAA GGA ACT AGA ATG CGG GCT CCT GAC TAC           3591
Phe Cys Arg Arg Leu Lys Glu Gly Thr Arg Met Arg Ala Pro Asp Tyr
        1095                1100                1105

ACT ACC CCA GAA ATG TAC CAG ACC ATG CTG GAC TGC TGG CAT GAG GAC           3639
Thr Thr Pro Glu Met Tyr Gln Thr Met Leu Asp Cys Trp His Glu Asp
1110                1115                1120                1125

CCC AAC CAG AGA CCC TCG TTT TCA GAG TTG GTG GAG CAT TTG GGA AAC           3687
Pro Asn Gln Arg Pro Ser Phe Ser Glu Leu Val Glu His Leu Gly Asn
                1130                1135                1140

CTC CTG CAA GCA AAT GCG CAG CAG GAT GGC AAA GAC TAT ATT GTT CTT           3735
Leu Leu Gln Ala Asn Ala Gln Gln Asp Gly Lys Asp Tyr Ile Val Leu
                1145                1150                1155

CCA ATG TCA GAG ACA CTG AGC ATG GAA GAG GAT TCT GGA CTC TCC CTG           3783
Pro Met Ser Glu Thr Leu Ser Met Glu Glu Asp Ser Gly Leu Ser Leu
            1160                1165                1170

CCT ACC TCA CCT GTT TCC TGT ATG GAG GAA GAG GAA GTG TGC GAC CCC           3831
Pro Thr Ser Pro Val Ser Cys Met Glu Glu Glu Glu Val Cys Asp Pro
        1175                1180                1185

AAA TTC CAT TAT GAC AAC ACA GCA GGA ATC AGT CAT TAT CTC CAG AAC           3879
Lys Phe His Tyr Asp Asn Thr Ala Gly Ile Ser His Tyr Leu Gln Asn
1190                1195                1200                1205

AGT AAG CGA AAG AGC CGG CCA GTG AGT GTA AAA ACA TTT GAA GAT ATC           3927
Ser Lys Arg Lys Ser Arg Pro Val Ser Val Lys Thr Phe Glu Asp Ile
                1210                1215                1220

CCA TTG GAG GAA CCA GAA GTA AAA GTG ATC CCA GAT GAC AGC CAG ACA           3975
Pro Leu Glu Glu Pro Glu Val Lys Val Ile Pro Asp Asp Ser Gln Thr
                1225                1230                1235

GAC AGT GGG ATG GTC CTT GCA TCA GAA GAG CTG AAA ACT CTG GAA GAC           4023
Asp Ser Gly Met Val Leu Ala Ser Glu Glu Leu Lys Thr Leu Glu Asp
            1240                1245                1250
```

-continued

```
AGG AAC AAA TTA TCT CCA TCT TTT GGT GGA ATG ATG CCC AGT AAA AGC    4071
Arg Asn Lys Leu Ser Pro Ser Phe Gly Gly Met Met Pro Ser Lys Ser
        1255            1260            1265

AGG GAG TCT GTG GCC TCG GAA GGC TCC AAC CAG ACC AGT GGC TAC CAG    4119
Arg Glu Ser Val Ala Ser Glu Gly Ser Asn Gln Thr Ser Gly Tyr Gln
1270            1275            1280            1285

TCT GGG TAT CAC TCA GAT GAC ACA GAC ACC ACC GTG TAC TCC AGC GAC    4167
Ser Gly Tyr His Ser Asp Asp Thr Asp Thr Thr Val Tyr Ser Ser Asp
            1290            1295            1300

GAG GCA GGA CTT TTA AAG ATG GTG GAT GCT GCA GTT CAC GCT GAC TCA    4215
Glu Ala Gly Leu Leu Lys Met Val Asp Ala Ala Val His Ala Asp Ser
                1305            1310            1315

GGG ACC ACA CTG CAG CTC ACC TCC TGT TTA AAT GGA AGT GGT CCT GTC    4263
Gly Thr Thr Leu Gln Leu Thr Ser Cys Leu Asn Gly Ser Gly Pro Val
        1320            1325            1330

CCG GCT CCG CCC CCA ACT CCT GGA AAT CAC GAG AGA GGT GCT GCT        4308
Pro Ala Pro Pro Pro Thr Pro Gly Asn His Glu Arg Gly Ala Ala
        1335            1340            1345

TAGATTTTCA AGTGTTGTTC TTTCCACCAC CCGGAAGTAG CCACATTTGA TTTTCATTTT    4368

TGGAGGAGGG ACCTCAGACT GCAAGGAGCT TGTCCTCAGG GCATTTCCAG AGAAGATGCC    4428

CATGACCCAA GAATGTGTTG ACTCTACTCT CTTTTCCATT CATTTAAAAG TCCTATATAA    4488

TGTGCCCTGC TGTGGTCTCA CTACCAGTTA AAGCAAAAGA CTTTCAAACA CGTGGACTCT    4548

GTCCTCCAAG AAGTGGCAAC GGCACCTCTG TGAAACTGGA TCGAATGGGC AATGCTTTGT    4608

GTGTTGAGGA TGGGTGAGAT GTCCCAGGGC CGAGTCTGTC TACCTTGGAG GCTTTGTGGA    4668

GGATGCGGCT ATGAGCCAAG TGTTAAGTGT GGGATGTGGA CTGGGAGGAA GGAAGGCGCA    4728

AGCCGTCCGG AGAGCGGTTG GAGCCTGCAG ATGCATTGTG CTGGCTCTGG TGGAGGTGGG    4788

CTTGTGGCCT GTCAGGAAAC GCAAAGGCGG CCGGCAGGGT TTGGTTTTGG AAGGTTTGCG    4848

TGCTCTTCAC AGTCGGGTTA CAGGCGAGTT CCCTGTGGCG TTTCCTACTC CTAATGAGAG    4908

TTCCTTCCGG ACTCTTACGT GTCTCCTGGC CTGGCCCCAG GAAGGAAATG ATGCAGCTTG    4968

CTCCTTCCTC ATCTCTCAGG CTGTGCCTTA ATTCAGAACA CCAAAAGAGA GGAACGTCGG    5028

CAGAGGCTCC TGACGGGGCC GAAGAATTGT GAGAACAGAA CAGAAACTCA GGGTTTCTGC    5088

TGGGTGGAGA CCCACGTGGC GCCCTGGTGG CAGGTCTGAG GGTTCTCTGT CAAGTGGCGG    5148

TAAAGGCTCA GGCTGGTGTT CTTCCTCTAT CTCCACTCCT GTCAGGCCCC CAAGTCCTCA    5208

GTATTTTAGC TTTGTGGCTT CCTGATGGCA GAAAAATCTT AATTGGTTGG TTTGCTCTCC    5268

AGATAATCAC TAGCCAGATT TCGAAATTAC TTTTTAGCCG AGGTTATGAT AACATCTACT    5328

GTATCCTTTA GAATTTTAAC CTATAAAACT ATGTCTACTG GTTTCTGCCT GTGTGCTTAT    5388

GTTAAAAAAA AAAAAAAA                                                  5406
```

(2) INFORMATION FOR SEQ ID NO: 6:

(i) SEQUENCE CHARACTERISTICS:
        (A) LENGTH: 1367 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Glu Ser Lys Gly Leu Leu Ala Val Ala Leu Trp Phe Cys Val Glu
-19             -15             -10                 -5

Thr Arg Ala Ala Ser Val Gly Leu Pro Gly Asp Phe Leu His Pro Pro
            1               5                   10
```

-continued

```
Lys Leu Ser Thr Gln Lys Asp Ile Leu Thr Ile Leu Ala Asn Thr Thr
     15                  20                  25

Leu Gln Ile Thr Cys Arg Gly Gln Arg Asp Leu Asp Trp Leu Trp Pro
 30                  35                  40                  45

Asn Ala Gln Arg Asp Ser Glu Glu Arg Val Leu Val Thr Glu Cys Gly
                 50                  55                  60

Gly Gly Asp Ser Ile Phe Cys Lys Thr Leu Thr Ile Pro Arg Val Val
             65                  70                  75

Gly Asn Asp Thr Gly Ala Tyr Lys Cys Ser Tyr Arg Asp Val Asp Ile
         80                  85                  90

Ala Ser Thr Val Tyr Val Tyr Val Arg Asp Tyr Arg Ser Pro Phe Ile
     95                 100                 105

Ala Ser Val Ser Asp Gln His Gly Ile Val Tyr Ile Thr Glu Asn Lys
110                 115                 120                 125

Asn Lys Thr Val Val Ile Pro Cys Arg Gly Ser Ile Ser Asn Leu Asn
                130                 135                 140

Val Ser Leu Cys Ala Arg Tyr Pro Glu Lys Arg Phe Val Pro Asp Gly
            145                 150                 155

Asn Arg Ile Ser Trp Asp Ser Glu Ile Gly Phe Thr Leu Pro Ser Tyr
        160                 165                 170

Met Ile Ser Tyr Ala Gly Met Val Phe Cys Glu Ala Lys Ile Asn Asp
    175                 180                 185

Glu Thr Tyr Gln Ser Ile Met Tyr Ile Val Val Val Gly Tyr Arg
190                 195                 200                 205

Ile Tyr Asp Val Ile Leu Ser Pro Pro His Glu Ile Glu Leu Ser Ala
                210                 215                 220

Gly Glu Lys Leu Val Leu Asn Cys Thr Ala Arg Thr Glu Leu Asn Val
            225                 230                 235

Gly Leu Asp Phe Thr Trp His Ser Pro Pro Ser Lys Ser His His Lys
        240                 245                 250

Lys Ile Val Asn Arg Asp Val Lys Pro Phe Pro Gly Thr Val Ala Lys
    255                 260                 265

Met Phe Leu Ser Thr Leu Thr Ile Glu Ser Val Thr Lys Ser Asp Gln
270                 275                 280                 285

Gly Glu Tyr Thr Cys Val Ala Ser Ser Gly Arg Met Ile Lys Arg Asn
                290                 295                 300

Arg Thr Phe Val Arg Val His Thr Lys Pro Phe Ile Ala Phe Gly Ser
            305                 310                 315

Gly Met Lys Ser Leu Val Glu Ala Thr Val Gly Ser Gln Val Arg Ile
        320                 325                 330

Pro Val Lys Tyr Leu Ser Tyr Pro Ala Pro Asp Ile Lys Trp Tyr Arg
    335                 340                 345

Asn Gly Arg Pro Ile Glu Ser Asn Tyr Thr Met Ile Val Gly Asp Glu
350                 355                 360                 365

Leu Thr Ile Met Glu Val Thr Glu Arg Asp Ala Gly Asn Tyr Thr Val
                370                 375                 380

Ile Leu Thr Asn Pro Ile Ser Met Glu Lys Gln Ser His Met Val Ser
            385                 390                 395

Leu Val Val Asn Val Pro Pro Gln Ile Gly Glu Lys Ala Leu Ile Ser
        400                 405                 410

Pro Met Asp Ser Tyr Gln Tyr Gly Thr Met Gln Thr Leu Thr Cys Thr
    415                 420                 425
```

-continued

```
Val Tyr Ala Asn Pro Pro Leu His His Ile Gln Trp Tyr Trp Gln Leu
430                 435                 440                 445

Glu Glu Ala Cys Ser Tyr Arg Pro Gly Gln Thr Ser Pro Tyr Ala Cys
                450                 455                 460

Lys Glu Trp Arg His Val Glu Asp Phe Gln Gly Gly Asn Lys Ile Glu
            465                 470                 475

Val Thr Lys Asn Gln Tyr Ala Leu Ile Glu Gly Lys Asn Lys Thr Val
        480                 485                 490

Ser Thr Leu Val Ile Gln Ala Ala Asn Val Ser Ala Leu Tyr Lys Cys
    495                 500                 505

Glu Ala Ile Asn Lys Ala Gly Arg Gly Glu Arg Val Ile Ser Phe His
510                 515                 520                 525

Val Ile Arg Gly Pro Glu Ile Thr Val Gln Pro Ala Ala Gln Pro Thr
                530                 535                 540

Glu Gln Glu Ser Val Ser Leu Leu Cys Thr Ala Asp Arg Asn Thr Phe
                545                 550                 555

Glu Asn Leu Thr Trp Tyr Lys Leu Gly Ser Gln Ala Thr Ser Val His
            560                 565                 570

Met Gly Glu Ser Leu Thr Pro Val Cys Lys Asn Leu Asp Ala Leu Trp
575                 580                 585

Lys Leu Asn Gly Thr Met Phe Ser Asn Ser Thr Asn Asp Ile Leu Ile
590                 595                 600                 605

Val Ala Phe Gln Asn Ala Ser Leu Gln Asp Gln Gly Asp Tyr Val Cys
                610                 615                 620

Ser Ala Gln Asp Lys Lys Thr Lys Lys Arg His Cys Leu Val Lys Gln
                625                 630                 635

Leu Ile Ile Leu Glu Arg Met Ala Pro Met Ile Thr Gly Asn Leu Glu
            640                 645                 650

Asn Gln Thr Thr Thr Ile Gly Glu Thr Ile Glu Val Thr Cys Pro Ala
            655                 660                 665

Ser Gly Asn Pro Thr Pro His Ile Thr Trp Phe Lys Asp Asn Glu Thr
670                 675                 680                 685

Leu Val Glu Asp Ser Gly Ile Val Leu Arg Asp Gly Asn Arg Asn Leu
                690                 695                 700

Thr Ile Arg Arg Val Arg Lys Glu Asp Gly Gly Leu Tyr Thr Cys Gln
            705                 710                 715

Ala Cys Asn Val Leu Gly Cys Ala Arg Ala Glu Thr Leu Phe Ile Ile
            720                 725                 730

Glu Gly Ala Gln Glu Lys Thr Asn Leu Glu Val Ile Ile Leu Val Gly
            735                 740                 745

Thr Ala Val Ile Ala Met Phe Phe Trp Leu Leu Leu Val Ile Leu Val
750                 755                 760                 765

Arg Thr Val Lys Arg Ala Asn Glu Gly Glu Leu Lys Thr Gly Tyr Leu
                770                 775                 780

Ser Ile Val Met Asp Pro Asp Glu Leu Pro Leu Asp Glu Arg Cys Glu
            785                 790                 795

Arg Leu Pro Tyr Asp Ala Ser Lys Trp Glu Phe Pro Arg Asp Arg Leu
            800                 805                 810

Lys Leu Gly Lys Pro Leu Gly Arg Gly Ala Phe Gly Gln Val Ile Glu
            815                 820                 825

Ala Asp Ala Phe Gly Ile Asp Lys Thr Ala Thr Cys Lys Thr Val Ala
830                 835                 840                 845

Val Lys Met Leu Lys Glu Gly Ala Thr His Ser Glu His Arg Ala Leu
```

-continued

```
                850                 855                 860
Met Ser Glu Leu Lys Ile Leu Ile His Ile Gly His His Leu Asn Val
            865                 870                 875
Val Asn Leu Leu Gly Ala Cys Thr Lys Pro Gly Gly Pro Leu Met Val
            880                 885                 890
Ile Val Glu Phe Ser Lys Phe Gly Asn Leu Ser Thr Tyr Leu Arg Gly
            895                 900                 905
Lys Arg Asn Glu Phe Val Pro Tyr Lys Ser Lys Gly Ala Arg Phe Arg
910                 915                 920                 925
Gln Gly Lys Asp Tyr Val Gly Glu Leu Ser Val Asp Leu Lys Arg Arg
            930                 935                 940
Leu Asp Ser Ile Thr Ser Ser Gln Ser Ser Ala Ser Ser Gly Phe Val
            945                 950                 955
Glu Glu Lys Ser Leu Ser Asp Val Glu Glu Glu Ala Ser Glu Glu
            960                 965                 970
Leu Tyr Lys Asp Phe Leu Thr Leu Glu His Leu Ile Cys Tyr Ser Phe
            975                 980                 985
Gln Val Ala Lys Gly Met Glu Phe Leu Ala Ser Arg Lys Cys Ile His
990                 995                 1000                1005
Arg Asp Leu Ala Ala Arg Asn Ile Leu Leu Ser Glu Lys Asn Val Val
                1010                1015                1020
Lys Ile Cys Asp Phe Gly Leu Ala Arg Asp Ile Tyr Lys Asp Pro Asp
            1025                1030                1035
Tyr Val Arg Lys Gly Asp Ala Arg Leu Pro Leu Lys Trp Met Ala Pro
            1040                1045                1050
Glu Thr Ile Phe Asp Arg Val Tyr Thr Ile Gln Ser Asp Val Trp Ser
            1055                1060                1065
Phe Gly Val Leu Leu Trp Glu Ile Phe Ser Leu Gly Ala Ser Pro Tyr
1070                1075                1080                1085
Pro Gly Val Lys Ile Asp Glu Glu Phe Cys Arg Arg Leu Lys Glu Gly
                1090                1095                1100
Thr Arg Met Arg Ala Pro Asp Tyr Thr Thr Pro Glu Met Tyr Gln Thr
            1105                1110                1115
Met Leu Asp Cys Trp His Glu Asp Pro Asn Gln Arg Pro Ser Phe Ser
            1120                1125                1130
Glu Leu Val Glu His Leu Gly Asn Leu Leu Gln Ala Asn Ala Gln Gln
            1135                1140                1145
Asp Gly Lys Asp Tyr Ile Val Leu Pro Met Ser Glu Thr Leu Ser Met
1150                1155                1160                1165
Glu Glu Asp Ser Gly Leu Ser Leu Pro Thr Ser Pro Val Ser Cys Met
            1170                1175                1180
Glu Glu Glu Glu Val Cys Asp Pro Lys Phe His Tyr Asp Asn Thr Ala
            1185                1190                1195
Gly Ile Ser His Tyr Leu Gln Asn Ser Lys Arg Lys Ser Arg Pro Val
            1200                1205                1210
Ser Val Lys Thr Phe Glu Asp Ile Pro Leu Glu Glu Pro Glu Val Lys
            1215                1220                1225
Val Ile Pro Asp Asp Ser Gln Thr Asp Ser Gly Met Val Leu Ala Ser
1230                1235                1240                1245
Glu Glu Leu Lys Thr Leu Glu Asp Arg Asn Lys Leu Ser Pro Ser Phe
                1250                1255                1260
Gly Gly Met Met Pro Ser Lys Ser Arg Glu Ser Val Ala Ser Glu Gly
                1265                1270                1275
```

```
Ser Asn Gln Thr Ser Gly Tyr Gln Ser Gly Tyr His Ser Asp Asp Thr
        1280                1285                1290

Asp Thr Thr Val Tyr Ser Ser Asp Glu Ala Gly Leu Leu Lys Met Val
        1295                1300                1305

Asp Ala Ala Val His Ala Asp Ser Gly Thr Thr Leu Gln Leu Thr Ser
1310                1315                1320                1325

Cys Leu Asn Gly Ser Gly Pro Val Pro Ala Pro Pro Thr Pro Gly
                1330                1335                1340

Asn His Glu Arg Gly Ala Ala
        1345
```

(2) INFORMATION FOR SEQ ID NO: 7:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

```
AATTCGTCGACT TTCTGTCACCAT GAGTGCACTTCT GATCCTAGCCCT TGTGGGAGCTGC    60

TGTTGCTGACTA CAAAGATGATGA TGACAAGATCTA                              96
```

(2) INFORMATION FOR SEQ ID NO: 8:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

```
AGCTTAGATCTT GTCATCATCATC TTTGTAGTCAGC AACAGCAGCTCC CACAAGGGCTAG    60

GATCAGAAGTGC ACTCATGGTGAC AGAAAGTCGACG                              96
```

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 9:

```
TGAGAAGATC TCAAACCAAG ACCTGCCTGT                                    30
```

(2) INFORMATION FOR SEQ ID NO: 10:

```
    (i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

CCAATGGCGGC CGCTCAGGAGA TGTTGTCTTGGA                                34

(2) INFORMATION FOR SEQ ID NO: 11:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 11:

Asp Tyr Lys Asp Asp Asp Asp Lys Ile
1               5
```

METHOD FOR ISOLATING CELLS EXPRESSING FLK-2

This application is a continuation of application U.S. Ser. No. 09/208,786, filed Dec. 10, 1998 now abandoned, which is a continuation of U.S. Ser. No. 09/021,324 filed Feb. 10, 1998, now U.S. Pat. No. 5,912,133, which is a continuation of U.S. Ser. No. 08/601,891 filed Feb. 15, 1996, now U.S. Pat. No. 5,747,651, which is a divisional of U.S. Ser. No. 08/252,498 filed Oct. 31, 1994, now abandoned, which is a divisional of U.S. Ser. No. 08/055,269 filed Apr. 30, 1993, now U.S. Pat. No. 5,367,057, which is a divisional of U.S. Ser. No. 07/977,451 filed Nov. 19, 1992, now U.S. Pat. No. 5,270,458, which is a continuation-in-part of U.S. Ser. No. 07/975,049 filed Nov. 12, 1992, now abandoned, which is a continuation-in-part of U.S. Ser. No. 07/906,397 filed Jun. 26, 1992, now U.S. Pat. No. 5,621,090, which is a continuation-in-part of U.S. Ser. No. 07/813,593 filed Dec. 24, 1991, now U.S. Pat. No. 5,185,438, which is a continuation-in-part of U.S. Ser. No. 07/793,065 filed Nov. 15, 1991, now abandoned, which is a continuation-in-part of U.S. Ser. No. 07/728,913 filed Jun. 28, 1991, now abandoned, which is a continuation-in-part of U.S. Ser. No. 07/679,666 filed Apr. 2, 1991, now abandoned.

The invention described in this application was made with U.S. government support from Grant Numbers R01-CA45339 and R01-DK42989 awarded by the National Institutes of Health. The government has certain rights in this invention.

FIELD OF THE INVENTION

The present invention relates to hematopoietic stem cell receptors, ligands for such receptors, and nucleic acid molecules encoding such receptors and ligands.

BACKGROUND OF THE INVENTION

The mammalian hematopoietic system comprises red and white blood cells. These cells are the mature cells that result from more primitive lineage-restricted cells. The cells of the hematopoietic system have been reviewed by Dexter and Spooncer in the Annual Review of Cell Biology 3, 423–441 (1987).

The red blood cells, or erythrocytes, result from primitive cells referred to by Dexter and Spooncer as erythroid burst-forming units (BFU-E). The immediate progeny of the erythroid burst-forming units are called erythroid colony-forming units (CFU-E).

The white blood cells contain the mature cells of the lymphoid and myeloid systems. The lymphoid cells include B lymphocytes and T lymphocytes. The B and T lymphocytes result from earlier progenitor cells referred to by Dexter and Spooncer as preT and preB cells.

The myeloid system comprises a number of cells including granulocytes, platelets, monocytes, macrophages, and megakaryocytes. The granulocytes are further divided into neutrophils, ecsinophils, basophils and mast cells.

Each of the mature hematopoietic cells are specialized for specific functions. For example, erythrocytes are responsible for oxygen and carbon dioxide transport. T and B lymphocytes are responsible for cell-and antibody-mediated immune responses, respectively. Platelets are involved in blood clotting. Granulocytes and macrophages act generally as scavengers and accessory cells in the immune response against invading organisms and their by-products.

At the center of the hematopoietic system lie one or more totipotent hematopoietic stem cells, which undergo a series of differentiation steps leading to increasingly lineage-restricted progenitor cells. The more mature progenitor cells are restricted to producing one or two lineages. Some examples of lineage-restricted progenitor cells mentioned by Dexter and Spooncer include granulocyte/macrophage colony-forming cells (GM-CFC), megakaryocyte colony-forming cells (Meg-CFC), eosinophil colony-forming cells (Eos-CFC), and basophil colony-forming cells (Bas-CFC). Other examples of progenitor cells are discussed above.

The hematopoietic system functions by means of a precisely controlled production of the various mature lineages. The totipotent stem cell possesses the ability both to self renew and to differentiate into committed progenitors for all hematopoietic lineages. These most primitive of hematopoietic cells are both necessary and sufficient for the complete and permanent hematopoietic reconstitution of a radiation-ablated hematopoietic system in mammals. The ability of stem cells to reconstitute the entire hematopoietic system is the basis of bone marrow transplant therapy.

It is known that growth factors play an important role in the development and operation of the mammalian hematopoietic system. The role of growth factors is complex, however, and not well understood at the present time. One reason for the uncertainty is that much of what is known about hematopoietic growth factors results from in vitro experiments. Such experiments do not necessarily reflect in vivo realities.

In addition, in vitro hematopoiesis can be established in the absence of added growth factors, provided that marrow stromal cells are added to the medium. The relationship between stromal cells and hematopoietic growth factors in vivo is not understood. Nevertheless, hematopoietic growth factors have been shown to be highly active in vivo.

From what is known about them, hematopoietic growth factors appear to exhibit a spectrum of activities. At one end of the spectrum are growth factors such as erythropoietin, which is believed to promote proliferation only of mature erythroid progenitor cells. In the middle of the spectrum are growth factors such as IL-3, which is believed to facilitate the growth and development of early stem cells as well as of numerous progenitor cells. Some examples of progenitor cells induced by IL-3 include those restricted to the granulocyte/macrophage, eosinophil, megakaryocyte, erythroid and mast cell lineages.

At the other end of the spectrum is the hematopoietic growth factor that, along with the corresponding receptor, was discussed in a series of articles in the Oct. 5, 1990 edition of Cell. The receptor is the product of the W locus, c-kit, which is a member of the class of receptor protein tyrosine kinases. The ligand for c-kit, which is referred to by various names such as stem cell factor (SCF) and mast cell growth factor (MGF), is believed to be essential for the development of early hematopoietic stem cells and cells restricted to the erythroid and mast cell lineages in mice; see, for example, Copeland et al., Cell 63, 175–183 (1990).

It appears, therefore, that there are growth factors that exclusively affect mature cells. There also appear to be growth factors that affect both mature cells and stem cells. The growth factors that affect both types of cells may affect a small number or a large number of mature cells.

There further appears to be an inverse relationship between the ability of a growth factor to affect mature cells and the ability of the growth factor to affect stem cells. For example, the c-kit ligand, which stimulates a small number of mature cells, is believed to be more important in the renewal and development of stem cells then is IL-3, which is reporter to stimulate proliferation of many mature cells (see above).

Prior to the present specification, there have been no reports of growth factors that exclusively stimulate stem cells in the absence of an effect on mature cells. The discovery of such growth factors would be of particular significance.

As mentioned above, c-kit is a protein tyrosine kinase (pTK). It is becoming increasingly apparent that the protein tyrosine kinases play an important role as cellular receptors for hematopoietic growth factors. Other receptor pTKs include the receptors of colony stimulating factor 1 (CSF-1) and PDGF.

The pTK family can be recognized by the presence of several conserved amino acid regions in the catalytic domain. These conserved regions are summarized by Hanks et al. in Science 241, 42–52 (1988), see FIG. 1 starting on page 46 and by Wilks in Proc. Natl. Acad. Sci. USA 86, 1603–1607 (1989), see FIG. 2 on page 1605.

Additional protein tyrosine kinases that represent hematopoietic growth factor receptors are needed in order more effectively to stimulate the self-renewal of the totipotent hematopoietic stem cell and to stimulate the development of all cells of the hematopoietic system both in vitro and in vivo. Novel hematopoietic growth factor receptors that are present only on primitive stem cells, but are not present on mature progenitor cells, are particularly desired. Ligands for the novel receptors are also desirable to act as hematopoietic growth factors. Nucleic acid sequences encoding the receptors and ligands are needed to produce recombinant receptors and ligands.

SUMMARY OF THE INVENTION

These and other objectives as will be apparent to those with ordinary skill in the art have been met by providing isolated mammalian nucleic acid molecules encoding receptor protein tyrosine kinases expressed in primitive hematopoietic cells and not expressed in mature hematopoietic cells. Also included are the receptors encoded by such nucleic acid molecules; the nucleic acid molecules encoding receptor protein tyrosine kinases having the sequences shown in FIG. 1a (murine flk-2), FIG. 1b (human flk-2) and FIG. 2 (murine flk-1); the receptor protein tyrosine kinases having the amino acid sequences shown in FIG. 1a, FIG. 1b and FIG. 2; ligands for the receptors; nucleic acid sequences that encode the ligands; and methods of stimulating the proliferation of primitive mammalian hematopoietic stem cells comprising contacting the stem cells with a ligand that binds to a receptor protein tyrosine kinase expressed in primitive mammalian hematopoietic cells and not expressed in mature hematopoietic cells.

DESCRIPTION OF THE FIGURES

FIGS. 1a.1 through 1a.6 shows the cDNA and amino acid sequences of murine flk-2. All subsequent references to FIG. 1a are intended to refer to FIGS. 1a.1 through 1a.6. The amino acid residues occur directly below the nucleotides in the open reading frame. Amino acids −27 to −1 constitute the hydrophobic leader sequence. Amino acids 1 to 517 constitute the extracellular receptor domain. Amino acids 518 to 537 constitute the transmembrane region. Amino acids 538 to 966 constitute the intracellular catalytic domain. Counting amino acid residue −27 as residue number 1, the following amino acid residues in the intracellular domain are catalytic sub-domains identified by Hanks (see above): 618–623, 811–819, 832–834, 857–862, 872–878 The sequence at residues 709–785 is a signature sequence characteristic of flk-2. The protein tyrosine kinases generally have a signature sequence in this region. (See SEQ. ID. NOS. 1–2)

FIGS. 1b.1 through 1b.6 shows the complete cDNA and amino acid sequences of human flk-2 receptor. All subsequent references to FIG. 1b are intended to refer to FIGS. 1b.1 through 1b.6. Amino acids −27 to −1 constitute the hydrophobic leader sequence. Amino acids 1 to 516 constitute the extracellular receptor domain. Amino acids 517 to 536 constitute the transmembrane region. Amino acids 537 to 966 constitute the intracellular catalytic domain. (See SEQ. ID. NOS. 3–4)

FIGS. 2.1 through 2.9 shows the cDNA and amino acid sequences of murine flk-1. All subsequent references to FIG. 2 are intended to refer to FIGS. 2.1 through 2.9. Amino acids −19 to −1 constitute the hydrophobic leader sequence. Amino acids 1 to 743 constitute the extracellular receptor domain. Amino acids 744 to 765 constitute the transmembrane region. Amino acids 766 to 1348 constitute the intracellular catalytic domain. (See SEQ. ID. NOS. 5–6)

DETAILED DESCRIPTION OF THE INVENTION

Receptors

Figure 3:
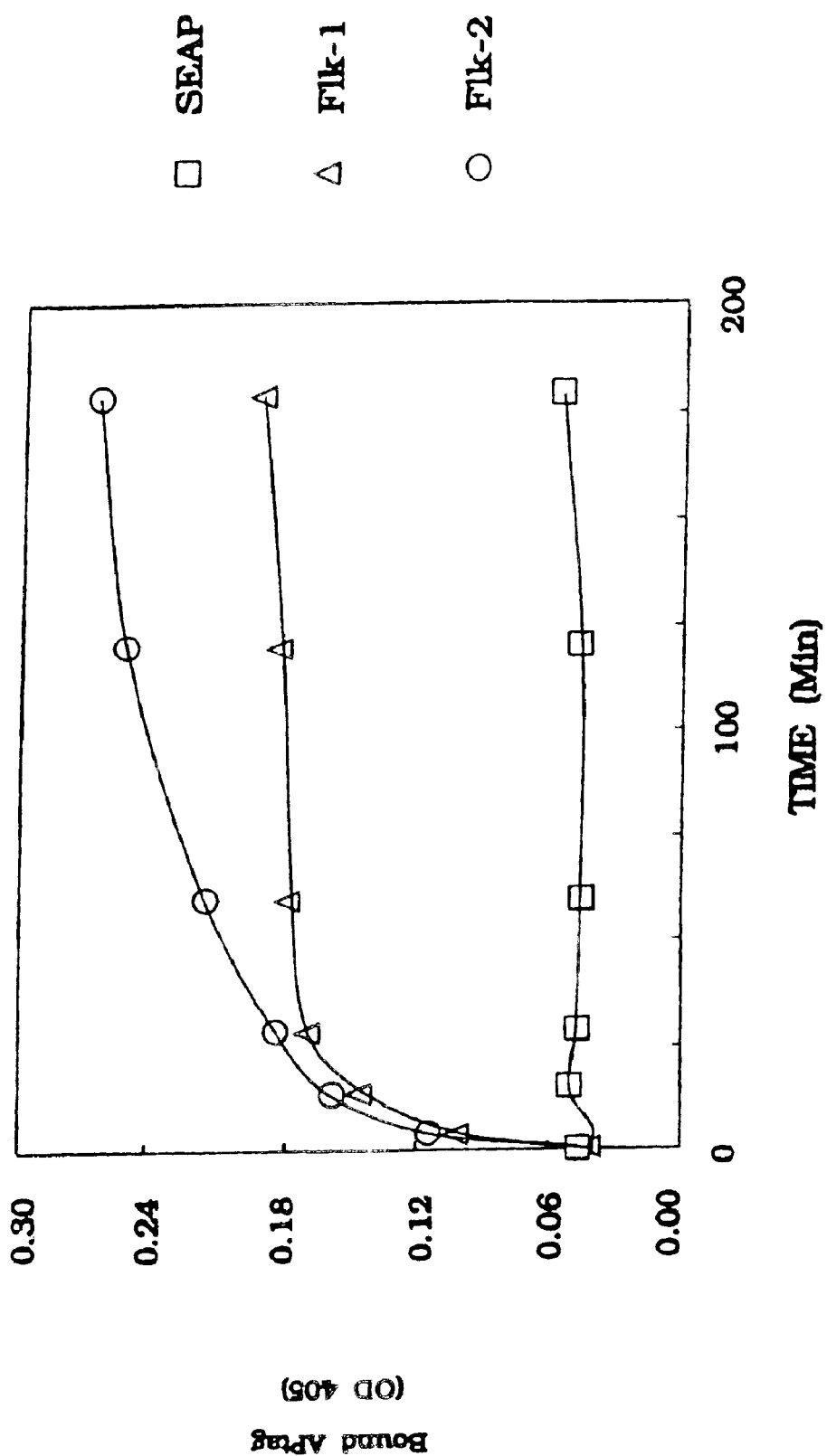
FIG. 3 shows the time response of binding between a murine stromal cell line (2018) and APtag-flk-2 as well as APtag-flk-1. APtag without receptor (SEAP) is used as a control. See Example 8.

In one embodiment, the invention relates to an isolated mammalian nucleic acid molecule encoding a receptor protein tyrosine kinase expressed in primitive mammalian hematopoietic cells and not expressed in mature hematopoietic cells.

The nucleic acid molecule may be a DNA, cDNA, or RNA molecule. The mammal in which the nucleic acid molecule exists may be any mammal, such as a mouse, rat, rabbit, or human.

The nucleic acid molecule encodes a protein tyrosine kinase (pTK). Members of the pTK family can be recognized by the conserved amino acid regions in the catalytic domains. Examples of pTK consensus sequences have been provided by Hanks et al. in Science 241, 42–52 (1988); see especially FIG. 1 starting on page 46 and by Wilks in Proc. Natl. Acad. Sci. USA 86, 1603–1607 (1989); see especially FIG. 2 on page 1605. A methionine residue at position 205 in the conserved sequence WMAPES is characteristic of pTK's that are receptors.

The Hanks et al article identifies eleven catalytic sub-domains containing pTK consensus residues and sequences. The pTKs of the present invention will have most or all of these consensus residues and sequences.

Some particularly strongly conserved residues and sequences are shown in Table 1.

TABLE 1

Conserved Residues and Sequences in pTKs[1]

| Position[2] | Residue or Sequence | Catalytic Domain |
|---|---|---|
| 50 | G | I |
| 52 | G | I |
| 57 | V | I |
| 70 | A | II |
| 72 | K | II |

TABLE 1-continued

Conserved Residues and Sequences in pTKs[1]

| Position[2] | Residue or Sequence | Catalytic Domain |
|---|---|---|
| 91 | E | III |
| 166 | D | VI |
| 171 | N | VI |
| 184–186 | DFG | VII |
| 208 | E | VIII |
| 220 | D | IX |
| 225 | G | IX |
| 280 | R | XI |

[1]See Hanks et al., Science 241, 42–52 (1988)
[2]Adjusted in accordance with Hanks et al., Id.

A pTK of the invention may contain all thirteen of these highly conserved residues and sequences. As a result of natural or synthetic mutations, the pTKs of the invention may contain fewer than all thirteen strongly conserved residues and sequences, such as 11, 9, or 7 such sequences.

The receptors of the invention generally belong to the same class of pTK sequences that c-kit belongs to. It has surprisingly been discovered, however, that a new functional class of receptor pTKs exists. The new functional class of receptor pTKs is expressed in primitive hematopoietic cells, but not expressed in mature hematopoietic cells.

For the purpose of this specification, a primitive hematopoietic cell is totipotent, i.e. capable of reconstituting all hematopoietic blood cells in vivo. A mature hematopoietic cell is non-self-renewing, and has limited proliferative capacity—i.e., a limited ability to give rise to multiple lineages. Mature hematopoietic cells, for the purposes of this specification, are generally capable of giving rise to only one or two lineages in vitro or in vivo.

It should be understood that the hematopoietic system is complex, and contains many intermediate cells between the primitive totipotent hematopoietic stem cell and the totally committed mature hematopoietic cells defined above. As the stem cell develops into increasingly mature, lineage-restricted cells, it gradually loses its capacity for self-renewal.

The receptors of the present invention may and may not be expressed in these intermediate cells. The necessary and sufficient condition that defines members of the new class of receptors is that they are present in the primitive, totipotent stem cell or cells, and not in mature cells restricted only to one or, at most, two lineages.

An example of a member of the new class of receptor pTKs is called fetal liver kinase 2 (flk-2) after the organ in which it was found. There is approximately 1 totipotent stem cell per $10^4$ cells in mid-gestation (day 14) fetal liver in mice. In addition to fetal liver, flk-2 is also expressed in fetal spleen, fetal thymus, adult brain, and adult marrow.

For example, flk-2 is expressed in individual multipotential CFU-Blast colonies capable of generating numerous multilineage colonies upon replating. It is likely, therefore, that flk-2 is expressed in the entire primitive (i.e. self-renewing) portion of the hematopoietic hierarchy. This discovery is consistent with flk-2 being important in transducing putative self-renewal signals from the environment.

It is particularly relevant that the expression of flk-2 mRNA occurs in the most primitive thymocyte subset. Even in two closely linked immature subsets that differ in expression of the IL-2 receptor, flk-2 expression segregates to the more primitive subset lacking an IL-2 receptor. The earliest thymocyte subset is believed to be uncommitted. Therefore, the thymocytes expressing flk-2 may be multipotential. flk-2 is the first receptor tyrosine kinase known to be expressed in the T-lymphoid lineage.

The fetal liver mRNA migrates relative to 28S and 18S ribosomal bands on formaldehyde agarose gels at approximately 3.5 kb, while the brain message is considerably larger. In adult tissues, flk-2 m-RNA from both brain and bone marrow migrated at approximately 3.5 kb.

A second pTK receptor is also included in the present invention. This second receptor, which is called fetal liver kinase 1 (flk-1), is not a member of the same class of receptors as flk-2, since flk-1 may be found in some more mature hematopoietic cells. The amino acid sequence of murine flk-1 is given in FIG. 2.

The present invention includes the flk-1 receptor as well as DNA, cDNA and RNA encoding flk-1. The DNA sequence of murine flk-1 is also given in FIG. 2. Flk-1 may be found in the same organs as flk-2, as well as in fetal brain, stomach, kidney, lung, heart and intestine; and in adult kidney, heart, spleen, lung, muscle, and lymph nodes.

The receptor protein tyrosine kinases of the invention are known to be divided into easily found domains. The DNA sequence corresponding to the pTKs encode, starting at their 5'-ends, a hydrophobic leader sequence followed by a hydrophilic extracellular domain, which binds to, and is activated by, a specific ligand. Immediately downstream from the extracellular receptor domain, is a hydrophobic transmembrane region. The transmembrane region is immediately followed by a basic catalytic domain, which may easily be identified by reference to the Hanks et al. and Wilks articles discussed above.

The following table shows the nucleic acid and amino acid numbers that correspond to the signal peptide, the extracellular domain, the transmembrane region and the intracellular domain for murine flk-1 (mflk-1), murine flk-2 (mflk-2) and human flk-2 (hflk-2).

| Signal Peptide | Extracellular | Transmembrane | Intracellular |
|---|---|---|---|
| mFLK-1 | | | |
| aa # −19 to −1 | 1 to 743 | 744 to 765 | 766 to 1348 |
| aa code M    A | A    E | V    V | R    A |
| na #   208–264 | 265–2493 | 2494–2559 | 2560–4308 |
| mFLK-2 | | | |
| aa # −27 to −1 | 1 to 517 | 518 to 537 | 538 to 966 |
| aa code M    T | N    S | F    C | H    S |
| na #   31–111 | 112–1662 | 1663–1722 | 1723–3006 |
| hFLK-2 | | | |
| aa # −27 to −1 | 1 to 516 | 517 to 536 | 537 to 966 |
| aa code M    N | Q    F | Y    C | H    S |
| na #   58–138 | 139–1689 | 1690–1746 | 1747–3036 |

The present invention includes the extracellular receptor domain lacking the transmembrane region and catalytic domain. Preferably, the hydrophobic leader sequence is also removed from the extracellular domain. In the case of human and murine flk-2, the hydrophobic leader sequence includes amino acids −27 to −1.

These regions and domains may easily be visually identified by those having ordinary skill in the art by reviewing the amino acid sequence in a suspected pTK and comparing it to known pTKs. For example, referring to FIG. 1a, the transmembrane region of flk-2, which separates the extracellular receptor domain from the catalytic domain, is encoded by nucleotides 1663 (T) to 1722 (C). These nucleotides correspond to amino acid residues 545 (Phe) to 564

(Cys). The amino acid sequence between the transmembrane region and the catalytic sub-domain (amino acids 618–623) identified by Hanks et al. as sub-domain I (i.e., GXGXXG) is characteristic of receptor protein tyrosine kinases.

The extracellular domain may also be identified through commonly recognized criteria of extracellular amino acid sequences. The determination of appropriate criteria is known to those skilled in the art, and has been described, for example, by Hopp et al, Proc. Nat'l Acad. Sci. USA 78, 3824–3828 (1981); Kyte et al, J. Mol. Biol. 157, 105–132 (1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed characteristic of extracellular domains.

As will be discussed in more detail below, the nucleic acid molecules that encode the receptors of the invention may be inserted into known vectors for use in standard recombinant DNA techniques. Standard recombinant DNA techniques are those such as are described in Sambrook et al., "Molecular Cloning," Second Edition, Cold Spring Harbor Laboratory Press (1987) and by Ausubel et al., Eds, "Current Protocols in Molecular Biology," Green Publishing Associates and Wiley-Interscience, New York (1987). The vectors may be circular (i.e. plasmids) or non-circular. Standard vectors are available for cloning and expression in a host. The host may be prokaryotic or eucaryotic. Prokaryotic hosts are preferably *E. coli*. Preferred eucaryotic hosts include yeast, insect and mammalian cells. Preferred mammalian cells include, for example, CHO, COS and human cells.

Ligands

The invention also includes ligands that bind to the receptor pTKs of the invention. In addition to binding, the ligands stimulate the proliferation of additional primitive stem cells, differentiation into more mature progenitor cells, or both.

The ligand may be a growth factor that occurs naturally in a mammal, preferably the same mammal that produces the corresponding receptor. The growth factor may be isolated and purified, or be present on the surface of an isolated population of cells, such as stromal cells.

The ligand may also be a molecule that does not occur naturally in a mammal. For example, antibodies, preferably monoclonal, raised against the receptors of the invention or against anti-ligand antibodies mimic the shape of, and act as, ligands if they constitute the negative image of the receptor or anti-ligand antibody binding site. The ligand may also be a non-protein molecule that acts as a ligand when it binds to, or otherwise comes into contact with, the receptor.

In another embodiment, nucleic acid molecules encoding the ligands of the invention are provided. The nucleic acid molecule may be RNA, DNA or cDNA.

Stimulating Proliferation of Stem Cells

The invention also includes a method of stimulating the proliferation and/or differentiation of primitive mammalian hematopoietic stem cells as defined above. The method comprises contacting the stem cells with a ligand in accordance with the present invention. The stimulation of proliferation and/or differentiation may occur in vitro or in vivo.

The ability of a ligand according to the invention to stimulate proliferation of stem cells in vitro and in vivo has important therapeutic applications. Such applications include treating mammals, including humans, whose primitive stem cells do not sufficiently undergo self-renewal. Example of such medical problems include those that occur when defects in hematopoietic stem cells or their related growth factors depress the number of white blood cells. Examples of such medical problems include anemia, such as macrocytic and aplastic anemia. Bone marrow damage resulting from cancer chemotherapy and radiation is another example of a medical problem that would be helped by the stem cell factors of the invention.

Functional Equivalents

The invention includes functional equivalents of the pTK receptors, receptor domains, and ligands described above as well as of the nucleic acid sequences encoding them. A protein is considered a functional equivalent of another protein for a specific function if the equivalent protein is immunologically cross-reactive with, and has the same function as, the receptors and ligands of the invention. The equivalent may, for example, be a fragment of the protein, or a substitution, addition or deletion mutant of the protein.

For example, it is possible to substitute amino acids in a sequence with equivalent amino acids. Groups of amino acids known normally to be equivalent are:

(a) Ala(A) Ser(S) Thr(T) Pro(P) Gly(G);

(b) Asn(N) Asp(D) Glu(E) Gln(Q);

(c) His(H) Arg(R) Lys(K);

(d) Met(M) Leu(L) Ile(I) Val(V); and (e) Phe(F) Tyr(Y) Trp(W).

Substitutions, additions and/or deletions in the receptors and ligands may be made as long as the resulting equivalent receptors and ligands are immunologically cross reactive with, and have the same function as, the native receptors and ligands.

The equivalent receptors and ligands will normally have substantially the same amino acid sequence as the native receptors and ligands. An amino acid sequence that is substantially the same as another sequence, but that differs from the other sequence by means of one or more substitutions, additions and/or deletions is considered to be an equivalent sequence. Preferably, less than 25%, more preferably less than 10%, and most preferably less than 5% of the number of amino acid residues in the amino acid sequence of the native receptors and ligands are substituted for, added to, or deleted from.

Equivalent nucleic acid molecules include nucleic acid sequences that encode equivalent receptors and ligands as defined above. Equivalent nucleic acid molecules also include nucleic acid sequences that differ from native nucleic acid sequences in ways that do not affect the corresponding amino acid sequences.

Isolation of Nucleic Acid Molecules and Proteins

Isolation of Nucleic Acid Molecules Encoding Receptors

In order to produce nucleic acid molecules encoding mammalian stem cell receptors, a source of stem cells is provided. Suitable sources include fetal liver, spleen, or thymus cells or adult marrow or brain cells.

For example, suitable mouse fetal liver cells may be obtained at day 14 of gestation. Mouse fetal thymus cells may be obtained at day 14–18, preferably day 15, of gestation. Suitable fetal cells of other mammals are obtained at gestation times corresponding to those of mouse.

Total RNA is prepared by standard procedures from stem cell receptor-containing tissue. The total RNA is used to direct cDNA synthesis. Standard methods for isolating RNA and synthesizing cDNA are provided in standard manuals of molecular biology such as, for example, in Sambrook et al., "Molecular Cloning," Second Edition, Cold Spring Harbor Laboratory Press (1987) and in Ausubel et al., (Eds), "Current Protocols in Molecular Biology," Greene Associates/Wiley Interscience, New York (1990).

The cDNA of the receptors is amplified by known methods. For example, the cDNA may be used as a template for amplification by polymerase chain reaction (PCR); see Saiki et al., Science, 239, 487 (1988) or Mullis et al., U.S. Pat. No. 4,683,195. The sequences of the oligonucleotide primers for the PCR amplification are derived from the sequences of known receptors, such as from the sequences given in FIGS. 1 and 2 for flk-2 and flk-1, respectively, preferably from flk-2. The oligonucleotides are synthesized by methods known in the art. Suitable methods include those described by Caruthers in Science 230, 281–285 (1985).

In order to isolate the entire protein-coding regions for the receptors of the invention, the upstream oligonucleotide is complementary to the sequence at the 5' end, preferably encompassing the ATG start codon and at least 5–10 nucleotides upstream of the start codon. The downstream oligonucleotide is complementary to the sequence at the 3' end, optionally encompassing the stop codon. A mixture of upstream and downstream oligonucleotides are used in the PCR amplification. The conditions are optimized for each particular primer pair according to standard procedures. The PCR product is analyzed by electrophoresis for the correct size cDNA corresponding to the sequence between the primers.

Alternatively, the coding region may be amplified in two or more overlapping fragments. The overlapping fragments are designed to include a restriction site permitting the assembly of the intact cDNA from the fragments.

The amplified DNA encoding the receptors of the invention may be replicated in a wide variety of cloning vectors in a wide variety of host cells. The host cell may be prokaryotic or eukaryotic. The DNA may be obtained from natural sources and, optionally, modified, or may be synthesized in whole or in part.

The vector into which the DNA is spliced may comprise segments of chromosomal, non-chromosomal and synthetic DNA sequences. Some suitable prokaryotic cloning vectors include plasmids from *E. coli,* such as colE1, pCR1, pBR322, pMB9, pUC, pKSM, and RP4. Prokaryotic vectors also include derivatives of phage DNA such as M13 and other filamentous single-stranded DNA phages.

Isolation of Receptors

DNA encoding the receptors of the invention are inserted into a suitable vector and expressed in a suitable prokaryotic or eucaryotic host. Vectors for expressing proteins in bacteria, especially *E. coli,* are known. Such vectors include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); lambda $P_L$; maltose binding protein (pMAL); and glutathione S-transferase (pGST)—see Gene 67, 31 (1988) and Peptide Research 3, 167 (1990).

Vectors useful in yeast are available. A suitable example is the 2μ plasmid.

Suitable vectors for use in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. Natl. Acad. Sci. USA 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, acenovirus, retrovirus, and simian virus, e.g., the early and late promoters or SV40, and other sequences known to control the expression of genes of prokaryotic or eukaryotic cells and their viruses or combinations thereof.

Vectors containing the receptor-encoding DNA and control signals are inserted into a host cell for expression of the receptor. Some useful expression host cells include well-known prokaryotic and eukaryotic cells. Some suitable prokaryotic hosts include, for example, *E. coli,* such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus,* such as *Bacillus subtilis,* and *Streptomyces.* Suitable eukaryotic cells include yeast and other fungi, insect, animal cells, such as COS cells and CHO cells, human cells and plant cells in tissue culture.

The human homologs of the mouse receptors described above are isolated by a similar strategy. RNA encoding the receptors are obtained from a source of human cells enriched for primitive stem cells. Suitable human cells include fecal spleen, thymus and liver cells, and umbilical cord blood as well as adult brain and bone marrow cells. The human fetal cells are preferably obtained on the day of gestation corresponding to mid-gestation in mice. The amino acid sequences of the human flk receptors as well as of the nucleic acid sequences encoding them are homologous to the amino acid and nucleotide sequences of the mouse receptors.

In the present specification, the sequence of a first protein, such as a receptor or a ligand, or of a nucleic acid molecule that encodes the protein, is considered homologous to a second protein or nucleic acid molecule if the amino acid or nucleotide sequence of the first protein or nucleic acid molecule is at least about 30% homologous, preferably at least about 50% homologous, and more preferably at least about 65% homologous to the respective sequences of the second protein or nucleic acid molecule. In the case of proteins having high homology, the amino acid or nucleotide sequence of the first protein or nucleic acid molecule is at least about 75% homologous, preferably at least about 85% homologous, and more preferably at least about 95% homologous to the amino acid or nucleotide sequence of the second protein or nucleic acid molecule.

Combinations of mouse oligonucleotide pairs are used as PCR primers to amplify the human homologs from the cells to account for sequence divergence. The remainder of the procedure for obtaining the human flk homologs are similar to those described above for obtaining mouse flk receptors. The less than perfect homology between the human flk homologs and the mouse oligonucleotides is taken into account in determining the stringency of the hybridization conditions.

Assay for Expression of Receptors on Stem Cells

In order to demonstrate the expression of flk receptors on the surface of primitive hematopoietic stem cells, antibodies that recognize the receptor are raised. The receptor may be the entire protein as it exists in nature, or an antigenic fragment of the whole protein. Preferably, the fragment comprises the predicted extra-cellular portion of the molecule.

Antigenic fragments may be identified by methods known in the art. Fragments containing antigenic sequences may be selected on the basis of generally accepted criteria of potential antigenicity and/or exposure. Such criteria include the hydrophilicity and relative antigenic index, as determined by surface exposure analysis of proteins. The determination of appropriate criteria is known to those skilled in the art, and has been described, for example, by Hopp et al, Proc. Nat'l Acad. Sci. USA 78, 3824–3828 (1981); Kyte et al, J. Mol. Biol. 157, 105–132 (1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed are selected preferentially over domains predicted to be more hydrophobic or hidden.

The proteins and fragments of the receptors to be used as antigens may be prepared by methods known in the art. Such methods include isolating or synthesizing DNA encoding the proteins and fragments, and using the DNA to produce recombinant proteins, as described above.

Fragments of proteins and DNA encoding the fragments may be chemically synthesized by methods known in the art from individual amino acids and nucleotides. Suitable methods for synthesizing protein fragments are described by Stuart and Young in "Solid Phase Peptide Synthesis," Second Edition, Pierce Chemical Company (1984). Suitable methods for synthesizing DNA fragments are described by Caruthers in Science 230, 281–285 (1985).

If the receptor fragment defines the epitope, but is too short to be antigenic, it may be conjugated to a carrier molecule in order to produce antibodies. Some suitable carrier molecules include keyhole limpet hemocyanin, Ig sequences, TrpE, and human or bovine serum albumen. Conjugation may be carried out by methods known in the art. One such method is to combine a cysteine residue of the fragment with a cysteine residue on the carrier molecule.

The antibodies are preferably monoclonal. Monoclonal antibodies may be produced by methods known in the art. These methods include the immunological method described by Kohler and Milstein in Nature 256, 495–497 (1975) and Campbell in "Monoclonal Antibody Technology, The Production and Characterization Of Rodent and Human Hybridomas" in Burdon et al., Eds, Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

Polyclonal or monoclonal antisera shown to be reactive with receptor-encoded native proteins, such as with flk-1 and flk-2 encoded proteins, expressed on the surface of viable cells are used to isolate antibody-positive cells. One method for isolating such cells is flow cytometry; see, for example, Loken et al., European patent application 317,156. The cells obtained are assayed for stem cells by engraftment into radiation-ablated hosts by methods known in the art; see, for example, Jordan et al., Cell 61, 953–963 (1990).

Criteria for Novel Stem Cell Receptor Tyrosine Kinases Expressed in Stem Cells

Additional novel receptor tyrosine kinase cDNAs are obtained by amplifying cDNAs from stem cell populations using oligonucleotides as PCR primers; see above. Examples of suitable oligonucleotides are PTK1 and PTK2, which were described by Wilks et al. in Proc. Natl. Acad. Sci. USA 86, 1603–1607 (1989). Novel cDNA is selected on the basis of differential hybridization screening with probes representing known kinases. The cDNA clones hybridizing only at low stringency are selected and sequenced. The presence of the amino acid triplet DFG confirms that the sequence represents a kinase. The diagnostic methionine residue in the WMAPES motif is indicative of a receptor-like kinase, as described above. Potentially novel sequences obtained are compared to available sequences using databases such as Genbank in order to confirm uniqueness. Gene-specific oligonucleotides are prepared as described above based on the sequence obtained. The oligonucleotides are used to analyze stem cell enriched and depleted populations for expression. Such cell populations in mice are described, for example, by Jordan et al. in Cell 61, 953–956 (1990); Ikuta et al. in Cell 62, 863–864 (1990); Spangrude et al. in Science 241, 58–62 (1988); and Szilvassy et al. in Blood 74, 930–939 (1989). Examples of such human cell populations are described as $CD33^-CD34^-$ by Andrews et al. in the Journal of Experimental Medicine 169, 1721–1731 (1989). Other human stem cell populations are described, for example, in Civin et al., European Patent Application 395, 355 and in Loken et al., European Patent Application 317,156.

Isolating Ligands and Nucleic Acid Molecules Encoding Ligands

Cells that may be used for obtaining ligands include stromal cells, for example stromal cells from fetal liver, fetal spleen, fetal thymus and fetal or adult bone marrow. Cell lines expressing ligands are established and screened.

For example, cells such as stromal (non-hematopoietic) cells from fetal liver are immortalized by known methods. Examples of known methods of immortalizing cells include transduction with a temperature sensitive SV40 T-antigen expressed in a retroviral vector. Infection of fetal liver cells with this virus permits the rapid and efficient establishment of multiple independent cell lines. These lines are screened for ligand activity by methods known in the art, such as those outlined below.

Ligands for the receptors of the invention, such as flk-1 and flk-2, may be obtained from the cells in several ways. For example, a bioassay system for ligand activity employs chimeric tagged receptors; see, for example, Flanagan et al., Cell 63, 185–194 (1990). One strategy measures ligand binding directly via a histochemical assay. Fusion proteins comprising the extracellular receptor domains and secretable alkaline phosphatase (SEAP) are constructed and transfected into suitable cells such as NIH/3T3 or COS cells. Flanagan et al refer to such DNA or amino acid constructs as APtag followed by the name of the receptor—i.e. APtag-c-kit. The fusion proteins bind with high affinity to cells expressing surface-bound ligand. Binding is detectable by the enzymatic activity of the alkaline phosphatase secreted into the medium. The bound cells, which are often stromal cells, are isolated from the APtag-receptor complex.

For example, some stromal cells that bind APtag-flk1 and APtag-flk2 fusion proteins include mouse fetal liver cells (see example 1); human fetal spleen cells (see example 3); and human fetal liver (example 3). Some stromal fetal thymus cells contain flk-1 ligand (example 3).

To clone the cDNA that encodes the ligand, a cDNA library is constructed from the isolated stromal cells in a suitable expression vector, preferably a phage such as CDM8, pSV Sport (BRL Gibco) or piH3, (Seed et al., Proc. Natl. Acad. Sci. USA 84, 3365–3369 (1987)). The library is transfected into suitable host cells, such as COS cells. Cells containing ligands on their surface are detected by known methods, see above.

In one such method, transfected COS cells are distributed into single cell suspensions and incubated with the secreted alkaline phosphatase-flk receptor fusion protein, which is present in the medium from NIH/3T3 or COS cells prepared by the method described by Flanagan et al., see above. Alkaline phosphatase-receptor fusion proteins that are not bound to the cells are removed by centrifugation, and the cells are panned on plates coated with antibodies to alkaline phosphatase. Bound cells are isolated following several washes with a suitable wash reagent, such as 5% fetal bovine serum in PBS, and the DNA is extracted from the cells. Additional details of the panning method described above may be found in an article by Seed et al., Proc. Natl. Acad. Sci. USA 84, 3365–3369 (1987).

In a second strategy, the putative extracellular ligand binding domains of the receptors are fused to the transmembrane and kinase domains of the human c-fms tyrosine kinase and introduced into 3T3 fibroblasts. The human c-fms kinase is necessary and sufficient to transduce proliferative signals in these cells after appropriate activation i.e. with the flk-1 or flk-2 ligand. The 3T3 cells expressing the chimeras are used to screen putative sources of ligand in a cell proliferation assay.

An alternate approach for isolating ligands using the fusion receptor-expressing 3T3 cells and insertional activation is also possible. A retrovirus is introduced into random chromosomal positions in a large population of these cells. In a small fraction, the retrovirus is inserted in the vicinity of the ligand-encoding gene, thereby activating it. These cells proliferate due to autocrine stimulation of the receptor. The ligand gene is "tagged" by the retrovirus, thus facilitating its isolation.

EXAMPLES

Example 1

Cells Containing Mouse flk-1 and flk-2 Ligands Murine Stromal Cell Line 2018.

In order to establish stromal cell lines, fetal liver cells are disaggregated with collagen and grown in a mixture of Dulbecco's Modified Eagle's Medium (DMEM) and 10% heat-inactivated fetal calf serum at 37° C. The cells are immortalized by standard methods. A suitable method involves introducing DNA encoding a growth regulating- or oncogene-encoding sequence into the target host cell. The DNA may be introduced by means of transduction in a recombinant viral particle or transfection in a plasmid. See, for example, Hammerschmidt et al., Nature 340, 393–397 (1989) and Abcouwer et al, Biotechnology 7, 939–946 (1989). Retroviruses are the preferred viral vectors, although SV40 and Epstein-Barr virus can also serve as donors of the growth-enhancing sequences. A suitable retrovirus is the ecotropic retrovirus containing a temperature sensitive SV40 T-antigen (tsA58) and a G418 resistance gene described by McKay in Cell 66, 713–729 (1991). After several days at 37° C., the temperature of the medium is lowered to 32° C. Cells are selected with G418 (0.5 mg/ml). The selected cells are expanded and maintained.

A mouse stromal cell line produced by this procedure is called 2018 and was deposited on Oct. 30, 1991 in the American Type Culture Collection, 10801 University Blvd., Manassas, Va. 20110-2209 U.S.A. (ATCC); accession number CRL 109071.

Example 2

Cells Containing Human flk-1 and flk-2 Ligands

Human fetal liver (18, 20, and 33 weeks after abortion), spleen (18 weeks after abortion), or thymus (20 weeks after abortion) is removed at the time of abortion and stored on ice in a balanced salt solution. After mincing into 1 mm fragments and forcing through a wire mesh, the tissue is washed one time in Hanks Balanced Salt Solution (HBSS).

The disrupted tissue is centrifuged at 200×g for 15 minutes at room temperature. The resulting pellet is resuspended in 10–20 ml of a tissue culture grade trypsin-EDTA solution (Flow Laboratories). The resuspended tissue is transferred to a sterile flask and stirred with a stirring bar at room temperature for 10 minutes. One ml of heat-inactivated fetal bovine calf serum (Hyclone) is added to a final concentration of 10% in order to inhibit trypsin activity. Collagenase type IV (Sigma) is added from a stock solution (10 mg/ml in HBSS) to a final concentration of 100 ug/ml in order to disrupt the stromal cells. The tissue is stirred at room temperature for an additional 2.5 hours; collected by centrifugation (400×g, 15 minutes); and resuspended in "stromal medium," which contains Iscove's modification of DMEM supplemented with 10% heat-inactivated fetal calf serum, 5% heat-inactivated human serum (Sigma), 4 mM L-glutamine, 1× sodium pyruvate, (stock of 100× Sigma), 1× non-essential amino acids (stock of 100×, Flow), and a mixture of antibiotics kanomycin, neomycin, penicillin, streptomycin. Prior to resuspending the pellet in the stromal medium, the pellet is washed one time with HBSS. It is convenient to suspend the cells in 60 ml of medium. The number of cultures depends on the amount of tissue.

Example 3

Isolating Stromal Cells

Resuspended Cells (example 2) that are incubated at 37° C. with 5% carbon dioxide begin to adhere to the plastic plate within 10–48 hours. Confluent monolayers may be observed within 7–10 days, depending upon the number of cells plated in the initial innoculum. Non-adherent and highly refractile cells adhering to the stromal cell layer as colonies are separately removed by pipetting and frozen. Non-adherent cells are likely sources of populations of self-renewing stem cells containing flk-2. The adherent stromal cell layers are frozen in aliquots for future studies or expanded for growth in culture.

An unexpectedly high level of APtag-flk-2 fusion protein binding to the fetal spleen cells is observed. Two fetal spleen lines are grown in "stromal medium," which is described in example 2.

Non-adherent fetal stem cells attach to the stromal cells and form colonies (colony forming unit—CFU). Stromal cells and CFU are isolated by means of sterile glass cylinders and expanded in culture. A clone, called Fsp 62891, contains the flk-2 ligand. Fsp 62891 was deposited in the American Type Culture Collection, 10801 University Blvd., Manassas, Va. 20110-2209 U.S.A. on Nov. 21, 1991, accession number CRL 10935.

Fetal liver and thymus cells are prepared in a similar way. Both of these cell types produce ligands of flk-1 and, in the case of liver, some flk-2. One such fetal thymus cell line, called F.thy 62891, and one such fetal liver cell line, called FL 62891, were deposited in the American Type Culture Collection, 10801 University Blvd., Manassas, Va., 20110-2209 U.S.A. on Nov. 21, 1991 and Apr. 2, 1992, respectively, accession numbers CRL 10936 and CRL 11005, respectively.

Stable human cell lines are prepared from fetal cells with the same temperature sensitive immortalizing virus used to prepare the murine cell line described in example 1.

Example 4

Isolation of Human Stromal Cell Clone

Highly retractile cells overgrow patches of stromal cells, presumably because the stromal cells produce factors that allow the formation of the CFU. To isolate stromal cell clones, sterile glass cylinders coated with vacuum grease are positioned over the CFU. A trypsin-EDTA solution (100 ml) is added in order to detach the cells. The cells are added to 5 ml of stromal medium and each (clone) plated in a single well of 6-well plate.

Example 5

Plasmid (AP-tag) for Expressing Secretable Alkaline Phosphatase (SEAP)

Plasmids that express secretable alkaline phosphatase are described by Flanagan and Leder in Cell 63, 185–194 (1990). The plasmids contain a promoter, such as the LTR promoter; a polylinker, including HindIII and BglII; DNA encoding SEAP; a poly-A signal; and ampicillin resistance gene; and replication site.

Example 6

Plasmid for Expressing APtag-flk-2 and APtag-flk-1 Fusion Proteins

Plasmids that express fusion proteins of SEAP and the extracellular portion of either flk-1 or flk-2 are prepared in accordance with the protocols of Flanagan and Leder in Cell 63, 185–194 (1990) and Berger et al., Gene 66, 1–10 (1988). Briefly, a HindIII-Bam HI fragment containing the extracellular portion of flk-1 or flk-2 is prepared and inserted into the HindIII-BglII site of the plasmid described in example 5.

Example 7

Production of APtaq-1 or -flk-2 Fusion Protein

The plasmids from Example 6 are transfected into Cos-7 cells by DEAE-dextran (as described in Current Protocols in Molecular Biology, Unit 16.13, "Transient Expression of Proteins Using Cos Cells," 1991); and cotransfected with a selectable marker, such as pSV7neo, into NIH/3T3 cells by calcium precipitation. The NIH/3T3 cells are selected with 600 µg/ml G418 in 100 mm plates. Over 300 clones are screened for secretion of placental alkaline phosphatase activity. The assay is performed by heating a portion of the supernatant at 65° C. for 10 minutes to inactivate background phosphatase activity, and measuring the $OD_{405}$ after incubating with 1M diethanolamine (pH 9.8), 0.5 mM $MgCl_2$, 10 mM L-homoarginine (a phosphatase inhibitor), 0.5 mg/ml BSA, and 12 mM p-nitrophenyl phosphate. Human placental alkaline phosphatase is used to perform a standard curve. The APtaq-flk-1 clones (F-1AP21-4) produce up to 10 µg alkaline phosphatase activity/ml and the APtaq-flk-2 clones (F-2AP26-0) produce up to 0.5 µg alkaline phosphatase activity/ml.

Example 8

Assay for APtaq-flk-1 or APtag-flk-2 Binding to Cells

Figure 4:
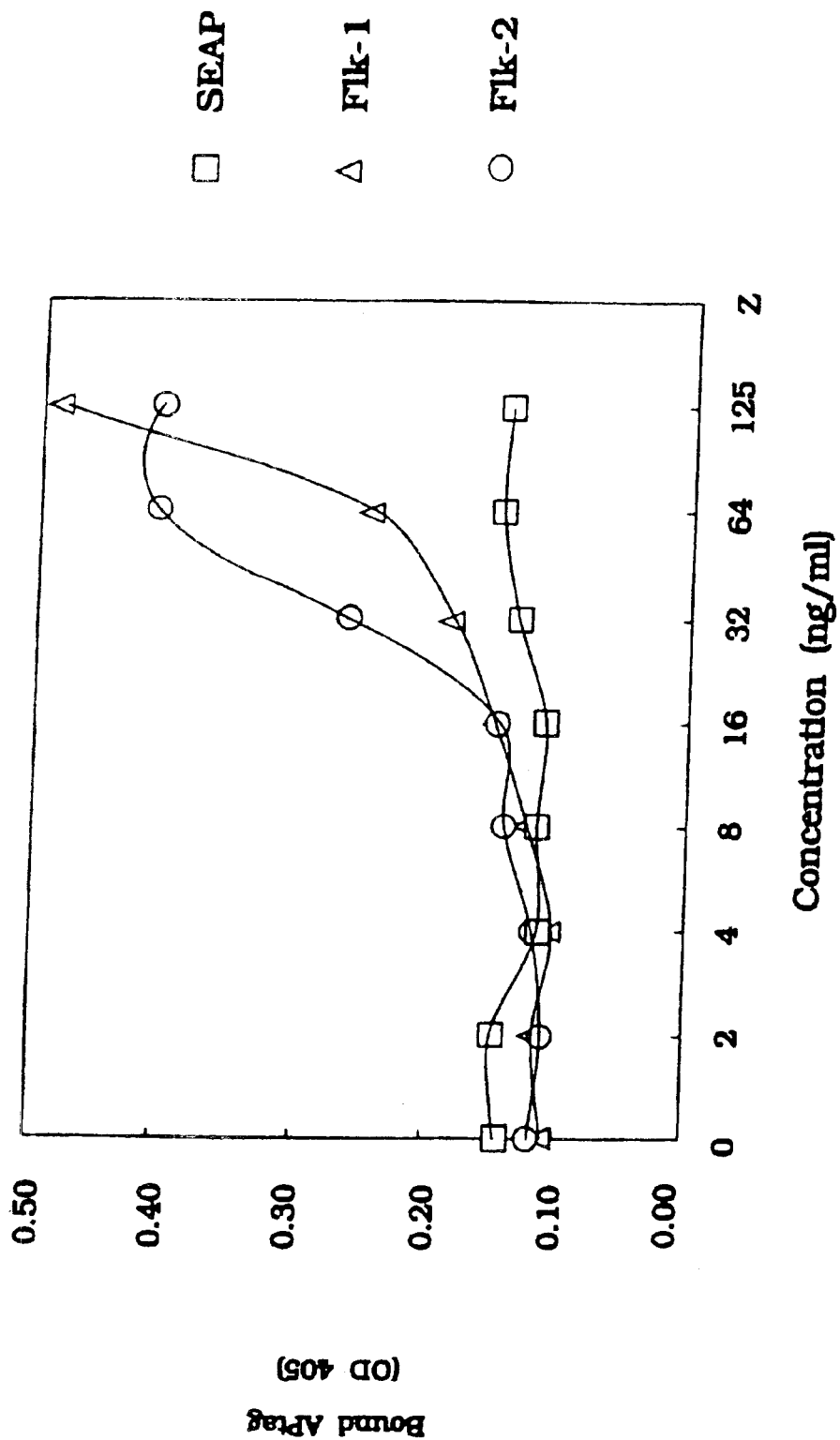
FIG. 4 shows the dose response of binding between stromal cells (2018) and APtag-flk-2 as well as APtag-flk-1. APtag without receptor (SEAP) is used as a control. See Example 8.

The binding of APtaq-flk-1 or APtag-flk-2 to cells containing the appropriate ligand is assayed by standard methods. See, for example, Flanagan and Leder, Cell 63:185–194, 1990). Cells (i.e., mouse stromal cells, human fetal liver, spleen or thymus, or various control cells) are grown to confluency in six-well plates and washed with HBHA (Hank's balanced salt solution with 0.5 mg/ml BSA, 0.02% $NaN_3$, 20 mM HEPES, pH 7.0). Supernatants from transfected COS or NIH/3T3 cells containing either APtaq-flk-1 fusion protein, APtag-flk-2 fusion protein, or APtag without a receptor (as a control) are added to the cell monolayers and incubated for two hours at room temperature on a rotating platform. The concentration of the APtaq-flk-1 fusion protein, APtag-flk-2 fusion protein, or APtag without a receptor is 60 ng/ml of alkaline phosphatase as determined by the standard alkaline phosphatase curve (see above). The cells are then rinsed seven times with HBHA and lysed in 350 µl of 1% Triton X-100, 10 mM Tris-HCl (pH 8.0). The lysates are transferred to a microfuge tube, along with a further 150 µl rinse with the same solution. After vortexing vigorously, the samples are centrifuged for five minutes in a microfuge, heated at 65° C. for 12 minutes to inactivate cellular phosphatases, and assayed for phosphatase activity as described previously. Results of experiments designed to show the time and dose responses of binding between stromal cells containing the ligands to flk-2 and flk-1 (2018) and APtag-flk-2, APtag-flk-1 and APtag without receptor (as a control) are shown in FIGS. 3 and 4, respectively.

Example 8A

Plasmids for Expressing flk1/fms and flk2/fms Fusion Proteins

Plasmids that express fusion proteins of the extracellular portion of either flk-1 or flk-2 and the intracellular portion of c-fms (also known as colony-stimulating factor-1 receptor) are prepared in a manner similar to that described under Example 6 (Plasmid for expressing APtag-flk-2 and APtag-flk-1 fusion proteins). Briefly, a Hind III-Bam HI fragment containing the extracellular portion of flk1 or flk2 is prepared and inserted into the Hind III-Bgl II site of a pLH expression vector containing the intracellular portion of c-fms.

8B

Expression of flk1/fms or flk2/fms in 3T3 Cells

The plasmids from Example 11 are transfected into NIH/3T3 cells by calcium. The intracellular portion of c-fms is detected by Western blotting.

Example 9

Cloning and Expression of cDNA Coding for Mouse Ligand to flk-1 and flk-2 Receptors cDNA expressing mouse ligand for flk-1 and flk-2 is prepared by known methods. See, for example, Seed, B., and Aruffo, A. PNAS 84:3365–3369, 1987; Simmons, D. and Seed, B. J. Immunol. 141:2797–2800; and D'Andrea, A. D., Lodish, H. F. and Wong, G. G. Cell 57:277–285, 1989).

The protocols are listed below in sequence: (a) RNA isolation; (b) poly A RNA preparation; (c) cDNA synthesis; (d) cDNA size fractionation; (e) propagation of plasmids (vector); (f) isolation of plasmid DNA; (g) preparation of vector pSV Sport (BRL Gibco) for cloning; (h) compilation of buffers for the above steps; (i) Transfection of cDNA encoding Ligands in Cos 7 Cells; (j) panning procedure; (k) Expression cloning of flk-1 or flk-2 ligand by establishment of an autocrine loop.

9a Guanidinium Thiocyanate/LiCl Protocol for RNA Isolation

For each ml of mix desired, 0.5 g guanidine thiocyanate (GuSCN) is dissolved in 0.55 ml of 25% LiCl (stock filtered through 0.45 micron filter). 20 $\mu$l of mercaptoethanol is added. (The resulting solution is not good for more than about a week at room temperature.)

The 2018 stromal cells are centrifuged, and 1 ml of the solution described above is added to up to $5\times10^7$ cells. The cells are sheared by means of a polytron until the mixture is non-viscous. For small scale preparations (<$10^8$ cells), the sheared mixture is layered on 1.5 ml of 5.7M CsCl (RNase free; 1.26 g CsCl added to every ml 10 mM EDTA pH8), and overlaid with RNase-free water if needed. The mixture is spun in an SW55 rotor at 50 krpm for 2 hours. For large scale preparations, 25 ml of the mixture is layered on 12 ml CsCl in an SW28 tube, overlaid as above, and spun at 24 krpm for 8 hours. The contents of the tube are aspirated carefully with a sterile pasteur pipet connected to a vacuum flask. Once past the CsCl interface, a band around the tube is scratched with the pipet tip to prevent creeping of the layer on the wall down the tube. The remaining CsCl solution is aspirated. The resulting pellet is taken up in water, but not redissolved. $\frac{1}{10}$ volume of sodium acetate and three volumes of ethanol are added to the mixture, and spun. The pellet is resuspended in water at 70° C., if necessary. The concentration of the RNA is adjusted to 1 mg/ml and frozen.

It should be noted that small RNA molecules (e.g., 5S) do not come down. For small amounts of cells, the volumes are scaled down, and the mixture is overlaid with GuSCN in RNase-free water on a gradient (precipitation is inefficient when RNA is dilute).

9b Poly A⁻ RNA Preparation (All buffers mentioned are compiled separately below)

A disposable polypropylene column is prepared by washing with 5M NaOH and then rinsing with RNase-free water. For each milligram of total RNA, approximately 0.3 ml (final packed bed) of oligo dT cellulose is added. The oligo dT cellulose is prepared by resuspending approximately 0.5 ml of dry powder in 1 ml of 0.1M NaOH and transferring it into the column, or by percolating 0.1M NaOH through a previously used column. The column is washed with several column volumes of RNase-free water until the pH is neutral, and rinsed with 2–3 ml of loading buffer. The column bed is transferred to a sterile 15 ml tube using 4–6 ml of loading buffer.

Total RNA from the 2018 cell line is heated to 70° C. for 2–3 minutes. LiCl from RNase-free stock is added to the mixture to a final concentration of 0.5M. The mixture is combined with oligo dT cellulose in the 15 ml tube, which is vortexed or agitated for 10 minutes. The mixture is poured into the column, and washed with 3 ml loading buffer, and then with 3 ml of middle wash buffer. The mRNA is eluted directly into an SW55 tube with 1.5 ml of 2 mM EDTA and 0.1% SDS, discarding the first two or three drops.

The eluted mRNA is precipitated by adding $\frac{1}{10}$ volume of 3M sodium acetate and filling the tube with ethanol. The contents of the tube are mixed, chilled for 30 minutes at −20° C., and spun at 50 krpm at 5° C. for 30 minutes. After the ethanol is decanted, and the tube air dried, the mRNA pellet is resuspended in 50–100 $\mu$l of RNase-free water. 5 $\mu$l of the resuspended mRNA is heated to 70° C. in MOPS/EDTA/formaldehyde, and examined on an RNase-free 1% agarose gel.

9c. cDNA Synthesis

The protocol used is a variation of the method described by Gubler and Hoffman in Gene 25, 263–270 (1983).

1. First Strand. 4 $\mu$g of mRNA is added to a microfuge tube, heated to approximately 100° C. for 30 seconds, quenched on ice. The volume is adjusted to 70$\mu$l with RNAse-free water. 20 l of RT1 buffer, 2 $\mu$l of RNAse inhibitor (Boehringer 36 u/$\mu$l), 1 $\mu$l of 5 $\mu$g/$\mu$l of oligo dT (Collaborative Research), 2.5 $\mu$l of 20 mM dXTP's (ultrapure—US Biochemicals), 1 $\mu$l of 1M DTT and 4 $\mu$l of RT-XL (Life Sciences, 24 u/$\mu$l) are added. The mixture is incubated at 42° C. for 40 minutes, and inactivated by heating at 70° C. for 10 minutes.

2. Second Strand. 320 $\mu$l of RNAse-free water, 80 $\mu$l of RT2 buffer, 5 $\mu$l of DNA Polymerase I (Boehringer, 5 U/$\mu$l), 2 $\mu$l RNAse H (BRL 2 u/$\mu$l) are added to the solution containing the first strand. The solution is incubated at 15° C. for one hour and at 22° C. for an additional hour. After adding 20 $\mu$l of 0.5M EDTA, pH 8.0, the solution is extracted with phenol and precipitated by adding NaCl to 0.5M linear polyacrylamide (carrier) to 20 $\mu$g/ml, and filling the tube with EtOH. The tube is spun for 2–3 minutes in a microfuge, vortexed to dislodge precipitated material from the wall of the tube, and respun for one minute.

3. Adaptors. Adaptors provide specific restriction sites to facilitate cloning, and are available from BRL Gibco, New England Biolabs, etc. Crude adaptors are resuspended at a concentration of 1 $\mu$g/$\mu$l. MgSO$_4$ is added to a final concentration of 10 mM, followed by five volumes of EtCH. The resulting precipitate is rinsed with 70% EtOH and resuspended in TE at a concentration of 1 $\mu$g/$\mu$l. To kinase, 25 $\mu$l of resuspended adaptors is added to 3 $\mu$l of 10× kinasing buffer and 20 units of kinase. The mixture is incubated at 37° C. overnight. The precipitated cDNA is resuspended in 240 $\mu$l of TE (10/1). After adding 30 $\mu$l of 10× low salt buffer, 30 $\mu$l of 10× ligation buffer with 0.1 mM ATP, 3 $\mu$l (2.4 $\mu$g) of kinased 12-mer adaptor sequence, 2 $\mu$l (1.6 $\mu$g) of kinased 8-mer adaptor sequence, and 1 $\mu$l of T4 DNA ligase (BioLabs, 400 u/$\mu$l, or Boehringer, 1 Weiss unit ml), the mixture is incubated at 15° C. overnight. The cDNA is extracted with phenol and precipitated as above, except that the extra carrier is omitted, and resuspended in 100 $\mu$l of TE.

9d. cDNA Size Fractionation

A 20% KOAc, 2 mM EDTA, 1 $\mu$g/ml ethidium bromide solution and a 5% KOAc, 2 mM EDTA, 1 $\mu$g/ml ethidium bromide solution are prepared. 2.6 ml of the 20% KOAc solution is added to the back chamber of a small gradient maker. Air bubbles are removed from the tube connecting the two chambers by allowing the 20% solution to flow into the front chamber and forcing the solution to return to the back chamber by tilting the gradient maker. The passage between the chambers is closed, and 2.5 ml of 5% solution is added to the front chamber. Any liquid in the tubing from a previous run is removed by allowing the 5% solution to flow to the end of the tubing, and then to return to its chamber. The apparatus is placed on a stirplate, and, with rapid stirring, the topcock connecting the two chambers and the front stopcock are opened. A polyallomer 5W55 tube is filled from the bottom with the KOAc solution. The gradient is overlaid with 100 μl of cDNA solution, and spun for three hours at 50 k rpm at 22° C. To collect fractions from the gradient, the SW55 tube is pierced close to the bottom of the tube with a butterfly infusion set (with the luer hub clipped off). Three 0.5 ml fractions and then six 0.25 ml fractions are collected in microfuge tubes (approximately 22 and 11 drops, respectively). The fractions are precipitated by adding linear polyacrylamide to 20 μg/ml and filling the tube to the top with ethanol. The tubes are cooled, spun in a microfuge tube for three minutes, vortexed, and respun for one minute. The resulting pellets are rinsed with 70% ethanol and respun, taking care not to permit the pellets to dry to completion. Each 0.25 ml fraction is resuspended in 10 μl of TE, and 1 μl is run on a 1% agarose minigel. The first three fractions, and the last six which contain no material smaller than 1 kb are pooled.

9e. Propagation of Plasmids

SupF plasmids are selected in nonsuppressing bacterial hosts containing a second plasmid, p3, which contains amber mutated ampicillin and tetracycline drug resistance elements. See Seed, Nucleic Acids Res., 11, 2427–2445 (1983). The p3 plasmid is derived from RP1, is 57 kb in length, and is a stably maintained, single copy episome. The ampicillin resistance of this plasmid reverts at a high rate so that amp plasmids usually cannot be used in p3-containing strains. Selection for tetracycline resistance alone is almost as good as selection for ampicillin-tetracycline resistance. However, spontaneous appearance of chromosomal suppressor tRNA mutations presents an unavoidable background (frequency about $10^{-9}$) in this system. Colonies arising from spontaneous suppressor mutations are usually larger than colonies arising from plasmid transformation. Suppressor plasmids are selected in Luria broth (LB) medium containing ampicillin at 12.5 μg/ml and tetracycline at 7.5 μg/ml. For scaled-up plasmid preparations, M9 Casamino acids medium containing glycerol (0.8%) is employed as a carbon source. The bacteria are grown to saturation.

Alternatively, pSV Sport (BRL, Gaithersberg, Md.) may be employed to provide SV40 derived sequences for replication, transcription initiation and termination in COS 7 cells, as well as those sequences necessary for replication and ampicillin resistance in *E. coli*.

9f. Isolation of Vector DNA/Plasmid

One liter of saturated bacterial cells are spun down in J6 bottles at 4.2 k rpm for 25 minutes. The cells are resuspended in 40 ml 10 mM EDTA, pH 8. 80 ml 0.2M NaOH and 1% SDS are added, and the mixture is swirled until it is clear and viscous. 40 ml 5M KOAc, pH 4.7 (2.5M KOAc, 2.5M HOAc) is added, and the mixture is shaken semi-vigorously until the lumps are approximately 2–3 mm in size. The bottle is spun at 4.2 k rpm for 5 minutes. The supernatant is poured through cheesecloth into a 250 ml bottle, which is then filled with isopropyl alcohol and centrifuged at 4.2 k rpm for 5 minutes. The bottle is gently drained and rinsed with 70% ethanol, taking care not to fragment the pellet. After inverting the bottle and removing traces of ethanol, the mixture is resuspended in 3.5 ml Tris base/EDTA (20 mM/10 mM). 3.75 ml of resuspended pellet and 0.75 ml 10 mg/ml ethidium bromide are added to 4.5 g CsCl. VTi80 tubes are filled with solution, and centrifuged for at least 2.5 hours at 80 k rpm. Bands are extracted by visible light with 1 ml syringe and 20 gauge or lower needle. The top of the tube is cut off with scissors, and the needle is inserted upwards into the tube at an angle of about 30 degrees with respect to the tube at a position about 3 mm beneath the band, with the bevel of the needle up. After the band is removed, the contents of the tube are poured into bleach. The extracted band is deposited in a 13 ml Sarstedt tube, which is then filled to the top with n-butanol saturated with 1M NaCl extract. If the amount of DNA is large, the extraction procedure may be repeated. After aspirating the butanol into a trap containing 5M NaOH to destroy ethidium, an approximately equal volume of 1M ammonium acetate and approximately two volumes of 95% ethanol are added to the DNA, which is then spun at 10 k rpm for 5 minutes. The pellet is rinsed carefully with 70% ethanol, and dried with a swab or lyophilizer.

9a. Preparation of Vector for Cloning

20 μg of vector is cut in a 200 μl reaction with 100 units of BstXI (New York Biolabs) at 50° C. overnight in a well thermostated, circulating water bath. Potassium acetate solutions (5 and 20%) are prepared in 5W55 tubes as described above. 100 μl of the digested vector is added to each tube and spun for three hours, 50 k rpm at 22° C. Under 300 m UV light, the desired band is observed to migrate ⅔ of the length of the tube. Forward trailing of the band indicates that the gradient is overloaded. The band is removed with a 1 ml syringe fitted with a 20 gauge needle. After adding linear polyacrylamide and precipitating the plasmid by adding three volumes of ethanol, the plasmid is resuspended in 50 μl of TE. Trial ligations are carried out with a constant amount of vector and increasing amounts of cDNA. Large scale ligation are carried out on the basis of these trial ligations. Usually the entire cDNA prep requires 1–2 μg of cut vector.

9h. Buffers

Loading Buffer: 0.5M LiCl, 10 mM Tris pH 7.5, 1 mM EDTA 0.1% SDS.
Middle Wash Buffer: 0.15M LiCl, 10 mM Tris pH 7.5, 1 mM EDTA 0.1% SDS.
RT1 Buffer: 0.25M Tris pH 8.8 (8.2 at 42⁻), 0.25M KCl, 30 mM $MgCl_2$.
RT2 Buffer: 0.1M Tris pH 7.5, 25 mM MgCl2, 0.5M KCl, 0.25 mg/ml BSA, 50 mM dithiothreitol (DTT).
10× Low Salt: 60 mM Tris pH 7.5, 60 mM $MgCl_2$, 50 mM NaCl, 2.5 mg/ml BSA 70 mM DME
10× Ligation Additions: 1 mM ATP, 20 mM DTT, 1 mg/ml BSA 10 mM spermidine.
10× Kinasing Buffer: 0.5M Tris pH 7.5, 10 mM ATP, 20 mM DTT, 10 mM spermidine, 1 mg/ml BSA 100 mM MgCl2

9i. Transfection of cDNA Encoding Ligands in Cos 7 Cells

Cos 7 cells are split 1:5 into 100 mm plates in Dulbecco's modified Eagles medium (DME)/10% fetal calf serum (FCS), and allowed to grow overnight. 3 ml Tris/DME (0.039M Tris, pH 7.4 in DME) containing 400 μg/ml DEAE-dextran (Sigma, D-9885) is prepared for each 100 mm plate of Cos 7 cells to be transfected. 10 μg of plasmid DNA preparation per plate is added. The medium is removed from the Cos-7 cells and the DNA/DEAE-dextran mixture is added. The cells are incubated for 4.5 hours. The medium is removed from the cells, and replaced with 3 ml of DME containing 2% fetal calf serum (FCS) and 0.1 mM chloroquine. The cells are incubated for one hour. After removing the chloroquine and replacing with 1.5 ml 20% glycerol in PBS, the cells are allowed to stand at room temperature for one minute. 3 ml Tris/DME is added, and the mixture is aspirated and washed two times with Tris/DME. 10 ml DME/10% FCS is added and the mixture is incubated overnight. The transfected Cos 7 cells are split 1:2 into fresh 100 mm plates with (DME)/10% FCS and allowed to grow.

9i. Panning Procedure for Cos 7 Cells Expressing Ligand

1) Antibody-coated Plates

Bacteriological 100 mm plates are coated for 1.5 hours with rabbit anti-human placental alkaline phosphatase (Dako, Calif.) diluted 1:500 in 10 ml of 50 mM Tris.HCl, pH 9.5. The plates are washed three times with 0.15M NaCl, and incubated with 3 mg BSA/ml PBS overnight. The blocking solution is aspirated, and the plates are utilized immediately or frozen for later use.

2) Panning Cells

The medium from transfected Cos 7 cells is aspirated, and 3 ml PBS/0.5 mM EDTA/0.02% sodium azide is added. The plates are incubated at 37° C. for thirty minutes in order to detach the cells. The cells are triturated vigorously with a pasteur pipet and collected in a 15 ml centrifuge tube. The plate is washed with a further 2 ml PBS/EDTA/azide solution, which is then added to the centrifuge tube. After centrifuging at 200×g for five minutes, the cells are resuspended in 3 ml of APtaq-flk-1 (F-1AP21-4) or flk-2 (F-2AP26-0) supernatant from transfected NIH/3T3 cells (see Example 7.), and incubated for 1.5 hours on ice. The cells are centrifuged again at 200×g for five minutes. The supernatant is aspirated, and the cells are resuspended in 3 ml PBS/EDTA/azide solution. The cell suspension is layered carefully on 3 ml PBS/EDTA/azide/2% Ficoll, and centrifuged at 200×g for four minutes. The supernatant is aspirated, and the cells are resuspended in 0.5 ml PBS/EDTA/azide solution. The cells are added to the antibody-coated plates containing 4 ml PBS/EDTA/azide/5% FBS, and allowed to stand at room temperature one to three hours. Non-adhering cells are removed by washing gently two or three times with 3 ml PBS/5% FBS.

3) Hirt Supernatant 0.4 ml 0.6% SDS and 10 mM EDTA are added to the panned plates, which are allowed to stand 20 minutes. The viscous mixture is added by means of a pipet into a microfuge tube. 0.1 ml 5M NaCl is added to the tube, mixed, and chilled on ice for at least five hours. The tube is spun for four minutes, and the supernatant is removed carefully. The contents of the tube are extracted with phenol once, or, if the first interface is not clean, twice. Ten micrograms of linear polyacrylamide (or other carrier) is added, and the tube is filled to the top with ethanol. The resulting precipitate is resuspended in 0.1 ml water or TE. After adding 3 volumes of EtOH/NaOAc, the cells are reprecipitated and resuspended in 0.1 ml water or TE. The cDNA obtained is transfected into any suitable $E. coli$ host by electroporation. Suitable hosts are described in various catalogs, and include MC1061/p3 or Electromax DH10B Cells of BRL Gibco. The cDNA is extracted by conventional methods.

The above panning procedure is repeated until a pure $E. coli$ clone bearing the cDNA as a unique plasmid recombinant capable of transfecting mammalian cells and yielding a positive panning assay is isolated. Normally, three repetitions are sufficient.

9k. Expression Cloning of flk1 or flk2 Ligand by Establishment of an Autocrine Loop Cells expressing flk1/fms or flk2/fms (Example 10) are transfected with 20–30 µg of a cDNA library from either flk1 ligand or flk2 ligand expressing stromal cells, respectively. The cDNA library is prepared as described above (a–h). The cells are co-transfected with 1 µg pLTR neo cDNA. Following transfection the cells are passaged 1:2 and cultured in 800 µg/ml of G418 in Dulbecco's medium (DME) supplemented with 10% CS. Approximately 12 days later the colonies of cells are passaged and plated onto dishes coated with poly-D-lysine (1 mg/ml) and human fibronectin (15 µg/ml). The culture medium is defined serum-free medium which is a mixture (3:1) of DME and Ham's F12 medium. The medium supplements are 8 mM $NaHCO_3$, 15 mM HEPES pH 7.4, 3 mM histidine, 4 µM $MnCl_2$, 10 µM ethanolamine, 0.1 µM selenous acid, 2 µM hydrocortisone, 5 µg/ml transferrin, 500 µg/ml bovine serum albumin/linoleic acid complex, and 20 µg/ml insulin (Ref. Zhan, X, et al. Oncogene 1: 369–376,1987). The cultures are refed the next day and every 3 days until the only cells capable of growing under the defined medium condition remain. The remaining colonies of cells are expanded and tested for the presence of the ligand by assaying for binding of APtag-flk1 or APtag-flk2 to the cells (as described in Example 8). The DNA would be rescued from cells demonstrating the presence of the flk1 or flk2 ligand and the sequence.

Example 10

Expression of Ligand cDNA

The cDNA is sequenced, and expressed in a suitable host cell, such as a mammalian cell, preferably COS, CHO or NIH/3T3 cells. The presence of the ligand is confirmed by demonstrating binding of the ligand to APtag-flk2 fusion protein (see above).

Example 11

Chemical Cross Linking of Receptor and Ligand

Cross linking experiments are performed on intact cells using a modification of the procedure described by Blume-Jensen et al et al., EMBO J., 10, 4121–4128 (1991). Cells are cultured in 100 mm tissue culture plates to subconfluence and washed once with PBS-0.1% BSA.

To examine chemical cross linking of soluble receptor to membrane-bound ligand, stromal cells from the 2018 stromal cell line are incubated with conditioned media (CM) from transfected 3T3 cells expressing the soluble receptor Flk2-APtag. Cross linking studies of soluble ligand to membrane bound receptor are performed by incubating conditioned media from 2018 cells with transfected 3T3 cells expressing a Flk2-fms fusion construct.

Binding is carried out for 2 hours either at room temperature with CM containing 0.02% sodium azide to prevent receptor internalization or at 4° C. with CM (and buffers) supplemented with sodium vanadate to prevent receptor dephosphorylation. Cells are washed twice with PBS-0.1% BSA and four times with PBS.

Cross linking is performed in PBS containing 250 mM disuccinimidyl suberate (DSS; Pierce) for 30 minutes at room temperature. The reaction is quenched with Tris-HCL pH7.4 to a final concentration of 50 mM.

Cells are solubilized in solubilization buffer: 0.5% Triton-X100, 0.5% deoxycholic acid, 20 mM Tris pH 7.4, 150 mM NaCl, 10 mM EDTA, 1 mM PMFS, 50 mg/ml aprotinin, 2 mg/ml bestatin, 2 mg/ml pepstatin and 10mg/ml leupeptin. Lysed cells are immediately transferred to 1.5 ml Nalgene tubes and solubilized by rolling end to end for 45 minutes at 4° C. Lysates are then centrifuged in a microfuge at 14,000 g for 10 minutes. Solubilized cross linked receptor complexes are then retrieved from lysates by incubating supernatants with 10% (v/v) wheat germ lectin-Sepharose 6MB beads (Pharmacia) at 4° C. for 2 hours or overnight.

Beads are washed once with Tris-buffered saline (TBS) and resuspended in 2×SDS-polyacrylamide nonreducing sample buffer. Bound complexes are eluted from the beads by heating at 95° C. for 5 minutes. Samples are analyzed on 4–12% gradient gels (NOVEX) under nonreducing and reducing conditions (0.35 M 2-mercaptoethanol) and then transferred to PVDF membranes for 2 hours using a Novex blotting apparatus. Blots are blocked in TBS-3% BSA for 1 hour at room temperature followed by incubation with appropriate antibody.

Cross linked Flk2-APtag and Flk2-fms receptors are detected using rabbit polyclonal antibodies raised against human alkaline phosphatase and fms protein, respectively. The remainder of the procedure is carried out according to the instructions provided in the ABC Kit (Pierce). The kit is based on the use of a biotinylated secondary antibody and avidin-biotinylated horseradish peroxidase complex for detection.

Example 12

Expression and Purification of Flag-Flk-2

1. Design of the Flag-Flk2 expression plasmids

A synthetic DNA fragment (Fragment 1) is synthesized using complementary oligonucleotides BP1 and BP2 (see below and SEQ. ID. NOS. 7 and 8). The fragment encoded the following features in the 5' to 3' order: Sal I restriction site, 22 base pair (bp) 5' untranslated region containing an eukaryotic ribosome binding site, an ATG initiation codon, preprotrypsinogen signal sequence, coding region for the FLAG peptide (DYKDDDDKI) (SEQ ID NO:11) and Bgl II restriction site.

A cDNA fragment (Fragment 2) encoding Asn 27 to Ser 544 of murine Flk2 is obtained by polymerase chain reaction (PCR) using primers designed to introduce an in frame Bgl II site at the 5' end (oligonucleotide BP5, see below and SEQ. ID. NO. 9) and a termination codon followed by a Not I site at the 3' end (oligonucleotide BP10, see below and SEQ. ID. NO. 10). The template for the PCR reaction is full length Flk2 cDNA (Matthews et al., Cell 65:1143 (1991)). Fragment 2 is extensively digested with Bgl II and Not I restriction enzymes prior to ligation. To assemble the complete Flag-Flk2 gene, Fragments 1 and 2 are ligated in a tripartate ligation into Sal I and Not I digested plasmid pSPORT (Gibco/BRL, Grand Island, N.Y.) to give the plasmid pFlag-Flk2.

Preferably, the Flag-Flk2 protein is attached at either end to the Fc portion of an immunoglobulin (Ig). The Ig is preferably attached to the Flk2 portion of the Flag-Flk2 protein. To assemble the construct pFlag-FLK2-Ig, the sequences coding for the $CH^1$ domain of human immunoglobulin G ($IgG^1$) are placed downstream of the Flk2 coding region in the plasmid pFlag-Flk2 as per the method described by Zettlemeissl et al., DNA and Cell Biology 9: 347–352 (1990).

The sequences of oligonucleotides used to construct the Flag-Flk2 gene are given below:

Oligonucleotide BP1 (SEQ ID NO:7):
5'-AATTCGTCGACTTTCTGTCACCATGAGTGCACT TCTGATCCTAGCCCTTGTG GGAGCTGCTGTTGCT- GACTACAAAGATGATGA TGACAAGATCTA-3'
Oligonucleotide BP2 (SEQ ID NO:8):
5'-AGCTTAGATCTTGTCATCATCATCTTTGTAGTCA GCAACAGCAGCTCCCACA AGGGCTAGGATCA- GAAGTGCACTCATGGTGAC AGAAAGTCGACG-3'
Oligonucleotide BP5 (SEQ ID NO:9):
5'-TGAGAAGATCTCAAACCAAGACCTGCCTGT-3'
Oligonucleotide BP10 (SEQ ID NO:10):
5'-CCAATGGCGGCCGCTCAGGAGATGTTGTCTTG GA-3'

2. Expression of the Flag-Flk2 Construct

For transient expression of the Flag-Flk2 construct, the Sal1 to Not I fragment from pFlag-Flk2 is subcloned into the plasmid pSVSPORT (Gibco/BRL) to give the plasmid pSVFlag-Flk2. For expression of the Flag-Flk2 protein pSVFlag-Flk2 is transfected into COS monkey cells using the DEAE-dextran method.

For stable expression in eukaryotic cells, the Sal I-Not I fragment of pFlag-Flk2 is cloned into the EcoRV and Not I sites of the plasmid pcDNA I/Neo (Invitrogen Co., San Diego, Calif.). The Sal I 3' recessed terminus of pFlag-Flk2 is filled with the Klenow fragment of DNA polymerase I and a mixture of deoxyribonucleotides to make the site compatible with the EcoRV site of the vector. The resulting construct is introduced into cultured mammalian cells using either the Lipofectin (Gibco/BRL) or the calcium phosphate methods.

For expression in insect cells, the Sal I to Hind III (from pSPORT polylinker) fragment of pFlag-Flk2 is subcloned into the BamH1-Hind III sites of the baculovirus transfer vector pBlueBac III (Invitrogen). The vector Bam HI site and the insert Sal I site are blunted with Klenow (see above). Production of the recombinant virus and infection of the Sf9 insect cells is performed as per manufacturers directions (Invitrogen).

Expression of the Flag-Flk2 protein is detected by Western blotting of SDS-PAGE separated conditioned media (mamalian cells) or cell lysates (insect cells) with the anti-Flag monoclonal antibody (mAb) M1 (International Biotechnology, Inc. [IBI], New Haven, Conn.).

3. Affinity purification of the Flag-Flk2 protein from conditioned media or insect cell lysates is performed using immobilized mAb M1 (IBI) as per manufacturers specifications.

3.1 Affinity purification of the Flag-Flk2-$Ig^1$ protein from conditioned media is performed using immobilized Protein A (Pharmacia LKB, Piscataway, N.J.) as per the manufacturers instructions.

II. Use of the Flag-Flk2 protein to search for the Flk2 ligand
1. Binding and cross-linking studies to detect membrane-bound ligand
A. Binding studies Murine stromal lines (eg. 2018 cells ATCC CRL 10907 (see below), see example 1, supra) considered to be candidates for expression of the Flk2 ligand were deposited at the American Type Culture Collection, ATCC CRL 10907 (see below) and cultured in Dulbecco's modified Eagles medium (DMEM; Gibco/BRL) supplemented with 10% fetal calf serum. The cells are grown to confluency in 10 cm plates and washed once with PBS. Conditioned media containing Flag-Flk2 is incubated with the cells at 4° C. for 2 hrs. The cell monolayers are rinsed extensively to remove the non-bound protein, solubilized and centrifuged to remove insoluble cellular material. Glycoproteins in the lysates are partially purified with wheat germ agglutinin-Sepharose (Pharmacia LKB, Piscataway, N.J.), boiled in an SDS sample buffer, separated on SDS-PAGE gels and transferred to nitrocellulose membranes. The membranes are probed with the M1 antibody to detect the presence of cell-associated Flag-Flk2 protein.

B. In a cross-linking study, the above protocol is followed except that prior to solubilization the monolayer are treated with the crosslinker disuccinimidyl suberate (DSS; Pierce, Rockford, Ill.). The presence of a putative ligand is detected by an upward shift in the apparent molecular weight of the Flag-Flk2 band on Western blots.

C. Purified Flag-Flk2 protein labelled with Na125 via the Chloramine T method is used to assess the ability of the soluble extracellular domain of the Flk-2 receptor to bind transmembrane form of the Flk2 ligand in cultured stromal lines. The labelled protein is added to monolayers of stromal cells on ice for 2 hr in the presence or absence of excess unlabelled protein. Specific binding is calculated by subtracting counts bound in the presence of excess unlabelled protein from the total counts bound.

2. Use of the Flag-Flk2 protein to search for secreted form of the ligand

A. The Flag-Flk2 protein is used in attempts to identify the Flk2 ligand in conditioned media from stromal cell cultures via modification of the direct N-terminal sequencing method of Pan et al., Bioch. Biophys. Res. Comm. 166:201 (1990). Briefly, the Flag-Flk2 protein N-terminally sequenced by automatic Edman degradation chemistry an an ABI 477A sequencer with on line PTH amino acid analysis. Approximately 15 amino acids are determined. The protein is then immobilized on Nugel PAF silica beads via free NH4+ groups. The immobilized Flag-Flk2 is incubated with conditioned media from putative ligand-producing cells for 30 min at 4° C. and washed free off non-bound proteins with phosphate buffered saline adjusted to 2M NaCl. The resulting protein complex is resequenced. For each sequencing cycle, any amino acid not expected at this position in the FLAG-Flk2 protein is considered as possibly originating from a protein complexed to the Flk2 receptor.

B. For conventional affinity chromatography, the Flag-Flk2 protein is immobilized on a stable support such as Sepharose. 35S-methionine labelled-conditioned media from stromal cell lines are passed over the affinity matrix and bound material is analyzed by SDS-PAGE gel electrophoresis and autoradiography.

3. Use of the Flag-Flk2 protein in expression cloning experiments

A method of expression cloning of integral membrane proteins in COS cells has been described (Aruffo and Seed, Proc. Natl. Acad. Sci. 84:8573 (1987)). A cDNA library is prepared from an appropriate stromal cell line such as 2018 and is transfected into COS cells. Cells transiently expressing the Flk2 ligand are affinity adsorbed onto plastic plates coated with the Flag-Flk2 protein. The cells are lysed, the plasmid DNA is recovered and amplified in a bacterial host. The cycle of transfection into Cos cells is repeated until a single cDNA clone encoding the ligand molecule is isolated.

In a modification of the above technique, pools of transfected COS cells are screened for binding of 125I-Flag-Flk2. Positive cells pools are selected and plasmid DNA is recovered and amplified in *E. coli*. The resulting DNA preparation is used in subsequent rounds of transfection and transient expression until all cells are positive for binding of 125I-Flag-Flk2. The cDNA in the final plasmid preparation is then sequenced to determine the sequence of the putative Flk-2 ligand.

Supplemental Enablement

The invention as claimed is enabled in accordance with the above specification and readily available references and starting materials. Nevertheless, Applicants have deposited with the American Type Culture Collection, 10801 University Blvd., Manassas, Va. 20110-2209 U.S.A. (ATCC) the cell lines listed below:

2018, ATCC accession no. CRL 10907, deposited Oct. 30, 1991.

Fsp 62891, ATCC accession no. CRL 10935, deposited Nov. 21, 1991.

F.thy 62891, ATCC accession no. CRL 10936, deposited Nov. 21, 1991.

FL 62891, ATCC accession no. CRL 11005, deposited Apr. 2, 1992.

These deposits were made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

What is claimed is:

1. A method for isolating cells that express FLK-2 on their surface, the method comprising binding the cells to a polyclonal or monoclonal antibody specific for the extracellular domain of a protein kinase that is FLK-2, said FLK-2 is defined by SEQ ID NO: 2 or by SEQ ID NO: 4, and isolating the cells that are bound to the antibody from cells that are unbound to the antibody.

* * * * *

UNITED STATES PATENT AND TRADEMARK OFFICE
CERTIFICATE OF CORRECTION

PATENT NO.    : 6,960,446 B2
DATED         : November 1, 2005
INVENTOR(S)   : Lemischka It is certified that error appears in the above-identified patent and that said Letters Patent is hereby corrected as shown below:

Column 1,
Line 5, change "1998 now abandoned" to -- 1998, now abandoned, --;
Line 57, change "ecsinophils" to -- eosinophils --;

Column 14,
Line 8, change "109071." to -- 10907. --;

Column 20,
Line 23, change "9a" to -- 9g --;

Column 21,
Line 14, change "9i" to -- 9j --.

Signed and Sealed this

Twenty-first Day of March, 2006

JON W. DUDAS
*Director of the United States Patent and Trademark Office*